(12) United States Patent
Lee et al.

(10) Patent No.: US 8,395,144 B2
(45) Date of Patent: Mar. 12, 2013

(54) ANTHRACENE DERIVATIVES AND ORGANIC ELECTROLUMINESCENT DEVICE USING SAME

(75) Inventors: Eunjung Lee, Seoul (KR); Jung-Sub Lee, Gunpo-si (KR); Tae-Hyung Kim, Yongin-si (KR); Kyoung-Soo Kim, Daejeon (KR)

(73) Assignee: Doosan Corporation, Seoul (KR)

( * ) Notice: Subject to any disclaimer, the term of this patent is extended or adjusted under 35 U.S.C. 154(b) by 223 days.

(21) Appl. No.: 12/945,486

(22) Filed: Nov. 12, 2010

(65) Prior Publication Data

US 2011/0057182 A1   Mar. 10, 2011

Related U.S. Application Data

(63) Continuation-in-part of application No. PCT/KR2009/002551, filed on May 14, 2009.

(30) Foreign Application Priority Data

May 14, 2008   (KR) ........................ 10-2008-0044275

(51) Int. Cl.
  *H01L 35/24* (2006.01)
  *H01L 51/00* (2006.01)
(52) U.S. Cl. ....... 257/40; 257/88; 257/78; 257/E21.053; 257/E21.126; 257/E21.127; 257/E21.262; 257/E21.264; 257/E21.352

(58) Field of Classification Search .................. 257/40, 257/78, 79, 88, 199, E21.053, E21.126, E21.127, 257/E21.262, E21.264, E21.352
See application file for complete search history.

(56) References Cited

U.S. PATENT DOCUMENTS

| | | | |
|---|---|---|---|
| 7,348,072 B2 | 3/2008 | Park et al. | |
| 2006/0192198 A1 | 8/2006 | Uckert | |
| 2007/0087223 A1 | 4/2007 | Sakamoto et al. | |
| 2008/0164811 A1 | 7/2008 | Kuma | |
| 2009/0085468 A1* | 4/2009 | Funahashi et al. | 313/504 |

FOREIGN PATENT DOCUMENTS

| | | |
|---|---|---|
| JP | 2002-326965 A | 11/2002 |
| JP | 2007-112729 A | 5/2007 |
| JP | 2007-137824 A | 6/2007 |
| KR | 10-2005-0056001 A | 6/2005 |
| KR | 10-2006-0069089 A | 6/2006 |
| KR | 10-2006-0080282 A | 7/2006 |
| WO | 2004/095892 A1 | 11/2004 |
| WO | 2005/042176 A1 | 5/2005 |

* cited by examiner

*Primary Examiner* — David Nhu
(74) *Attorney, Agent, or Firm* — Sughrue Mion, PLLC

(57) ABSTRACT

Provided are a novel anthracene derivative and an organic light-emitting device using the same, and more particularly, an anthracene derivative having a core (e.g., an indenoanthracene core) where an anthracene moiety with excellent device characteristics is fused with a fluorene moiety or the like with excellent fluorescent properties, wherein an aryl group is introduced at the core, and an organic light-emitting device using the anthracene derivative, which is enhanced in efficiency, operating voltage, lifetime, etc.

11 Claims, No Drawings

ANTHRACENE DERIVATIVES AND ORGANIC ELECTROLUMINESCENT DEVICE USING SAME

CROSS REFERENCE TO RELATED APPLICATIONS

This application is a Continuation-in-part of PCT/KR2009/002551, filed on May 14, 2009, which claims priority from Korean Patent Application No. 10-2008-0044275, filed on May 14, 2008, the contents of all of which are incorporated herein by reference in their entirety. The Application also incorporates by reference the contents of Korean Patent Application No. 10-2009-0109717 filed on Nov. 13, 2009.

1. FIELD OF THE INVENTION

The present invention relates to a novel anthracene derivative and an organic light-emitting device using the same. More particularly, the present invention relates to an anthracene derivative having a core (e.g., an indenoanthracene core) where an anthracene moiety with excellent device characteristics is fused with a fluorene moiety or the like with excellent fluorescent properties, wherein an aryl group is introduced at the core, and an organic light-emitting device using the anthracene derivative, which is enhanced in efficiency, operating voltage, lifetime, etc.

2. DESCRIPTION OF THE RELATED ART

Organic electronic devices are electronic devices using an organic semiconductor material and involve a hole and/or electron exchange between an electrode and an organic semiconductor material. Organic electronic devices can be largely classified according to an operating principle into two types. One type is that when photons derived from an external optical source enter into devices, exitons are generated from an organic material layer and dissociate into electrons and holes, and the resulting electrons and holes migrate to their respective corresponding electrodes so as to be used as current sources (voltage sources). The other type is that when a voltage or current is applied to two or more electrodes, holes and/or electrons are injected into organic semiconductor material layers interfacing with the electrodes to thereby operate devices.

Examples of organic electronic devices include organic light-emitting devices, organic photovoltaic/solar cells, organic photoconductor (OPC) drums, organic transistors, etc., and such organic electronic devices require an electron/hole injection material, an electron/hole extraction material, an electron/hole transport material or a light-emitting material so as to be operated. Organic light-emitting devices will be mainly described in detail hereinafter. However, organic electronic devices are operated on a similar principle in terms of an electron/hole injection material, an electron/hole extraction material, an electron/hole transport material and a light-emitting material.

Generally, an organic light-emitting phenomenon refers to the conversion of an electrical energy to light energy using an organic material. An organic light-emitting device using an organic light-emitting phenomenon generally includes an anode, a cathode, and an organic material layer between the anode and the cathode. In many cases, the organic material layer is structured such that a plurality of different layers formed of different materials are stacked to increase the efficiency and stability of organic light-emitting devices. For example, the organic material layer may include a hole injection layer, a hole transport layer, a light-emitting layer, an electron transport layer, an electron injection layer, etc.

In such an organic light-emitting device, when a voltage is applied between an anode and a cathode, holes from the anode and electrons from the cathodes are injected into an organic material layer. Thereafter, the holes and the electrons recombine at the organic material layer to generate excitons. When the excitons are converted from an excited state to a ground state, light emission occurs.

A material used in an organic material layer of an organic light-emitting device can be classified into a light-emitting material, a charge transport material, a hole injection material, a hole transport material, an electron transport material, an electron injection material, etc. according to the action (function) of the material.

A light-emitting material may include a blue light-emitting material, a green light-emitting material, a red light-emitting material, and for embodying better natural color, a yellow light-emitting material and an orange light-emitting material, based on emitting color. In order to increase color purity and emission efficiency through energy transition, a host/dopant based emitting material can be used. That is, when a dopant with a smaller energy bandgap than a host mainly constituting a light-emitting layer is contained in a trace amount in the light-emitting layer, exitons generated from the host are transferred to the dopant, thereby achieving highly efficient emission. At this time, the wavelength of the host is shifted to the wavelength range of the dopant. Thus, dopants may be chosen to provide emission in a desired wavelength range.

In order for the above-described organic light-emitting devices to satisfy desired characteristics, it is required that materials forming organic material layers of the devices, i.e., a hole injection material, a hole transport material, a light-emitting material, an electron transport material, an electron injection material, etc. should be stable and efficient materials. However, a material forming an organic material layer for an organic light-emitting device is still insufficient in terms of stability and efficiency. Thus, there is still need to develop such a stable and efficient organic material.

SUMMARY OF THE INVENTION

In view of the above problems, the present invention provides a novel light-emitting material capable of enhancing emission efficiency, brightness, energy efficiency, thermal stability and device lifetime, and an organic light-emitting device using the same.

According to an aspect of the present invention, there is provided a compound represented by Formula 1 below:

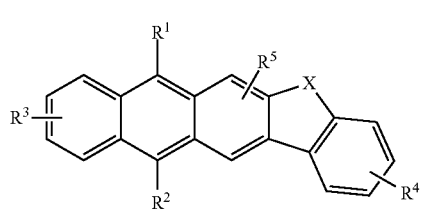

<Formula 1> wherein X is selected from the group consisting of $CR^6R^7$, $NR^6$, O, S, S($=$O), S($=$O)$_2$ and $SiR^6R^7$;

$R^1$ through $R^7$ are the same or different and each independently selected from the group consisting of hydrogen (H), deuterium (D), an alkyl group of $C_1$~$C_{40}$, an alkenyl group of $C_2$~$C_{40}$, an alkynyl group of $C_2$~$C_{40}$, an aryl group of $C_5\sim C_{40}$, a heteroaryl group of $C_5\sim C_{40}$, an aryloxy group of $C_5\sim C_{40}$, an alkyloxy group of $C_1\sim C_{40}$, an arylamino group of $C_5\sim C_{40}$, a diarylamino group of $C_5\sim C_{40}$, an arylalkyl group of $C_6\sim C_{40}$, a cycloalkyl group of $C_3\sim C_{40}$ and a heterocycloalkyl group of $C_3\sim C_{40}$, or a group binding with an adjacent group to form a fused aliphatic ring, a fused aromatic ring, a fused heteroaliphatic ring or a fused heteroaromatic ring;

in $R^1$ through $R^7$, the alkyl group of $C_1\sim C_{40}$, the alkenyl group of $C_2\sim C_{40}$, the alkynyl group of $C_2\sim C_{40}$, the aryl group of $C_5\sim C_{40}$, the heteroaryl group of $C_5\sim C_{40}$, the aryloxy group of $C_5\sim C_{40}$, the alkyloxy group of $C_1\sim C_{40}$, the arylamino group of $C_5\sim C_{40}$, the diarylamino group of $C_5\sim C_{40}$, the arylalkyl group of $C_6\sim C_{40}$, the cycloalkyl group of $C_3\sim C_{40}$ and the heterocycloalkyl group of $C_3\sim C_{40}$ are each independently unsubstituted or substituted by at least one selected from the group consisting of deuterium, halogen, nitrile, nitro, an alkyl group of $C_1\sim C_{40}$, an alkenyl group of $C_2\sim C_{40}$, an alkoxy group of $C_1\sim C_{40}$, an amino group of $C_1\sim C_{40}$, a cycloalkyl group of $C_3\sim C_{40}$, a heterocycloalkyl group of $C_3\sim C_{40}$, an aryl group of $C_6\sim C_{40}$ and a heteroaryl group of $C_5\sim C_{40}$; and two or more of $R^1$ through $R^4$ are each independently an aryl group of $C_5\sim C_{40}$.

According to another aspect of the present invention, there is provided an organic light-emitting device including (i) an anode, (ii) a cathode, and (iii) one or more organic material layers interposed between the anode and the cathode, wherein at least one of the organic material layers is an organic material layer including a compound represented by Formula 1.

In the organic light-emitting device, the organic material layer including the compound of Formula 1 may be a light-emitting layer.

When using the inventive compound of Formula 1 as a light-emitting material of an organic light-emitting device, it is possible to significantly increase color purity and efficiency as compared to a conventional light-emitting material. Therefore, the inventive organic light-emitting device can exhibit excellent performances in terms of emission efficiency, brightness, power efficiency, operating voltage and lifetime, thus enabling significant improvements in performances and lifetime of full-color organic electroluminescent (EL) panels.

DETAILED DESCRIPTION OF THE INVENTION

The inventive compound of Formula 1 is an anthracene derivative having a core (e.g., an indenoanthracene core) where an anthracene moiety with excellent device characteristics is fused with a fluorene moiety or the like with excellent fluorescent properties, wherein an aryl group is introduced at the core.

In the compound of Formula 1, $R^1$ through $R^7$ are the same or different and each independently selected from the group consisting of hydrogen (H), deuterium (D), an alkyl group of $C_1\sim C_{40}$, an alkenyl group of $C_2\sim C_{40}$, an alkynyl group of $C_2\sim C_{40}$, an aryl group of $C_5\sim C_{40}$, a heteroaryl group of $C_5\sim C_{40}$, an aryloxy group of $C_5\sim C_{40}$, an alkyloxy group of $C_1\sim C_{40}$, an arylamino group of $C_5\sim C_{40}$, a diarylamino group of $C_5\sim C_{40}$, an arylalkyl group of $C_5\sim C_{40}$, a cycloalkyl group of $C_3\sim C_{40}$ and a heterocycloalkyl group of $C_3\sim C_{40}$, or a group binding with an adjacent group to form a fused aliphatic ring, a fused aromatic ring, a fused heteroaliphatic ring or a fused heteroaromatic ring.

In $R^1$ through $R^7$, the alkyl group of $C_1\sim C_{40}$, the alkenyl group of $C_2\sim C_{40}$, the alkynyl group of $C_2\sim C_{40}$, the aryl group of $C_5\sim C_{40}$, the heteroaryl group of $C_5\sim C_{40}$, the aryloxy group of $C_5\sim C_{40}$, the alkyloxy group of $C_1\sim C_{40}$, the arylamino group of $C_5\sim C_{40}$, the diarylamino group of $C_5\sim C_{40}$, the arylalkyl group of $C_6\sim C_{40}$, the cycloalkyl group of $C_3\sim C_{40}$ and the heterocycloalkyl group of $C_3$-$C_{40}$ are each independently unsubstituted or substituted by at least one selected from the group consisting of deuterium, halogen, nitrile, nitro, an alkyl group of $C_1\sim C_{40}$, an alkenyl group of $C_2\sim C_{40}$, an alkoxy group of $C_1\sim C_{40}$, an amino group of $C_1\sim C_{40}$, a cycloalkyl group of $C_3\sim C_{40}$, a heterocycloalkyl group of $C_3\sim C_{40}$, an aryl group of $C_6\sim C_{40}$ and a heteroaryl group of $C_5\sim C_{40}$.

Among the substituents that can be introduced at the alkyl group of $C_1\sim C_{40}$, the alkenyl group of $C_2\sim C_{40}$, the alkynyl group of $C_2\sim C_{40}$, the aryl group of $C_5\sim C_{40}$, the heteroaryl group of $C_5\sim C_{40}$, the aryloxy group of $C_5\sim C_{40}$, the alkyloxy group of $C_1\sim C_{40}$, the arylamino group of $C_5\sim C_{40}$, the diarylamino group of $C_5\sim C_{40}$, the arylalkyl group of $C_6\sim C_{40}$, the cycloalkyl group of $C_3\sim C_{40}$ and the heterocycloalkyl group of $C_3\sim C_{40}$ of $R^1$ through $R^7$, the alkyl group of $C_1\sim C_{40}$, the alkenyl group of $C_2\sim C_{40}$, the alkoxy group of $C_1\sim C_{40}$, the amino group of $C_1\sim C_{40}$, the cycloalkyl group of $C_3\sim C_{40}$, the heterocycloalkyl group of $C_3\sim C_{40}$, the aryl group of $C_6\sim C_{40}$ and the heteroaryl group of $C_5\sim C_{40}$ may be each independently further substituted by at least one selected from the group consisting of deuterium, halogen, nitrile, nitro, an alkyl group of $C_1\sim C_{40}$, an alkenyl group of $C_2\sim C_{40}$, an alkoxy group of $C_1\sim C_{40}$, an amino group of $C_1\sim C_{40}$, a cycloalkyl group of $C_3\sim C_{40}$, a heterocycloalkyl group of $C_3\sim C_{40}$, an aryl group of $C_6\sim C_{40}$ and a heteroaryl group of $C_5\sim C_{40}$; or may bind with an adjacent group to form a fused aliphatic ring, a fused aromatic ring, a fused heteroaliphatic ring, a fused heteroaromatic ring, or a spiro bond.

In the compound of Formula 1, two or more of $R^1$ through $R^4$ are each independently an aryl group of $C_5\sim C_{40}$. Preferably, two or more of $R^1$ through $R^4$ are each independently an aryl group of $C_5\sim C_{40}$ selected from the group consisting of chemical structures represented in Formula 2 below. As a non-limiting example, among $R^1$ through $R^4$, $R^1$ and $R^2$; or $R^3$ and $R^4$; or $R^1$, $R^2$ and $R^3$; or $R^1$, $R^2$ and $R^4$; or $R^1$, $R^2$, $R^3$ and $R^4$ may be each independently an aryl group of $C_5\sim C_{40}$ selected from the group consisting of the chemical structures represented in Formula 2 below.

<Formula 2>

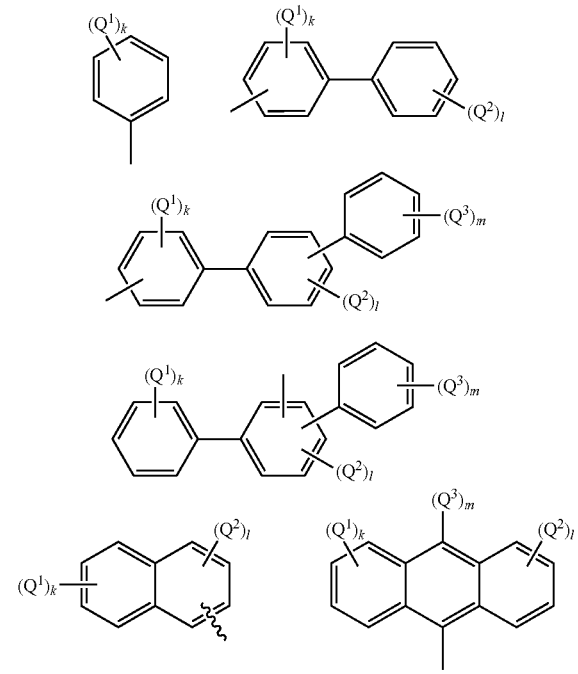

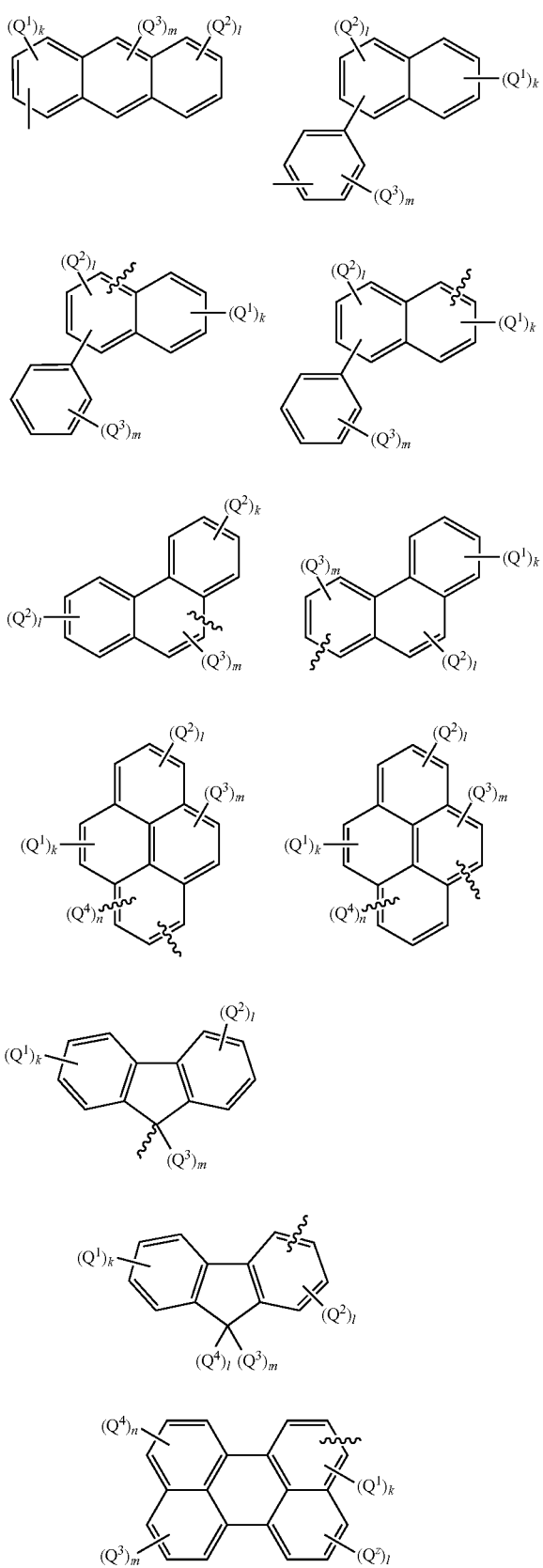
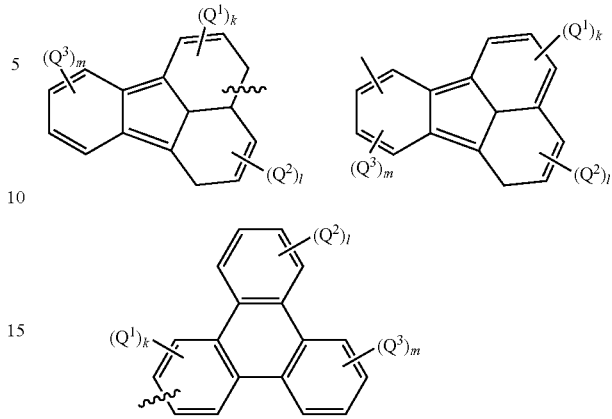

wherein k, l, m and n are each independently an integer ranging from 1 to 5;

$Q^1$s are the same or different, $Q^2$s are the same or different, $Q^3$s are the same or different and $Q^4$s are the same or different;

$Q^1$ through $Q^4$ are the same or different and each independently selected from the group consisting of hydrogen, deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$ and a heteroaryl group of $C_5$~$C_{40}$; or a group binding with an adjacent group to form a fused aliphatic ring, a fused aromatic ring, a fused heteroaliphatic ring or a fused heteroaromatic ring.

In $Q^1$ through $Q^4$, the alkyl group of $C_1$~$C_{40}$, the alkenyl group of $C_2$~$C_{40}$, the alkoxy group of $C_1$~$C_{40}$, the amino group of $C_1$~$C_{40}$, the cycloalkyl group of $C_3$~$C_{40}$, the heterocycloalkyl group of $C_3$~$C_{40}$, the aryl group of $C_6$~$C_{40}$ and a heteroaryl group of $C_5$~$C_{40}$ may be each independently unsubstituted or substituted by at least one selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$ and a heteroaryl group of $C_5$~$C_{40}$.

Non-limiting examples of the aryl group of $C_5$~$C_{40}$ selected from the group consisting of the chemical structures of Formula 2 include phenyl, biphenyl, terphenyl, naphthyl, anthracenyl, phenanthryl, pyrenyl, fluorenyl, fluoranthenyl and perylenyl. These aryl groups may be each independently substituted by at least one selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$ and a heteroaryl group of $C_5$~$C_{40}$; or may bind with an adjacent group to form a fused aliphatic ring, a fused aromatic ring, a fused heteroaliphatic ring, a fused heteroaromatic ring, or a Spiro bond.

Representative examples of the compound of Formula 1 include the following compounds, but the present invention is not limited thereto.

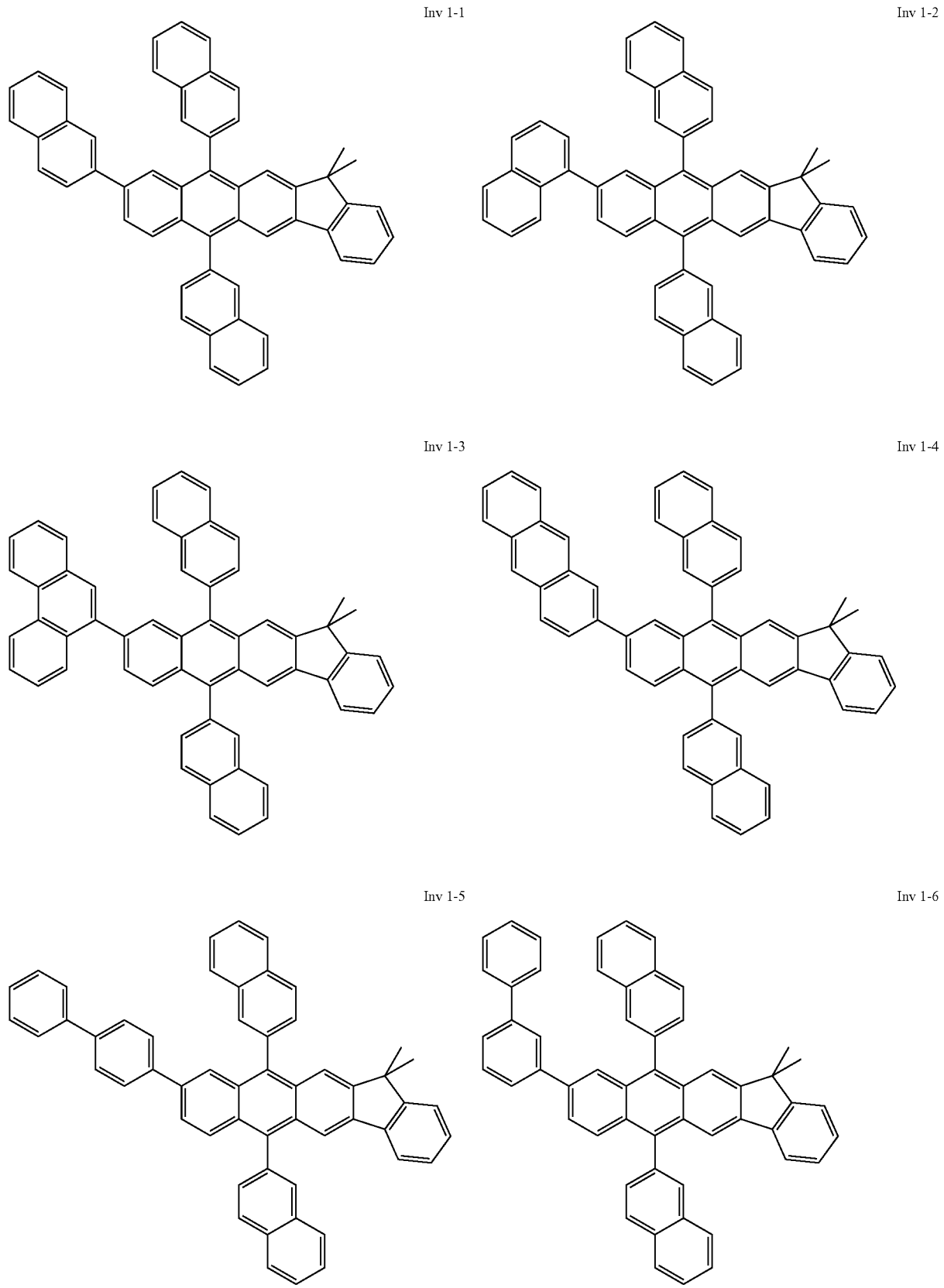

Inv 1-7
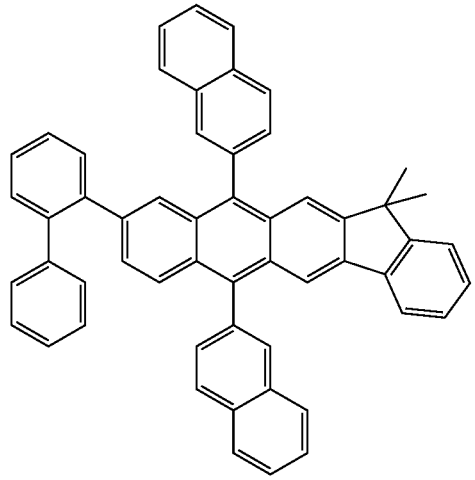
Inv 1-8
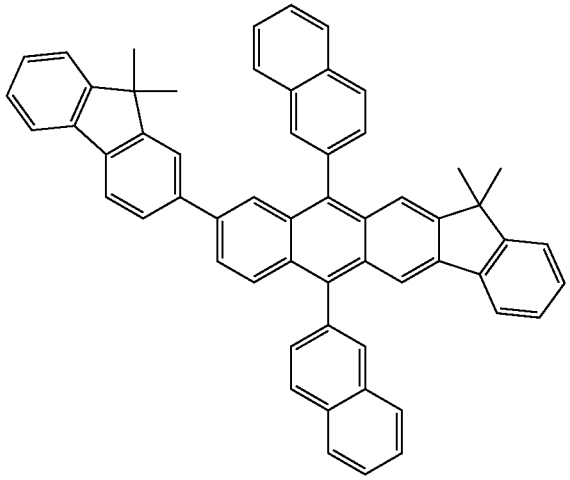
Inv 1-9
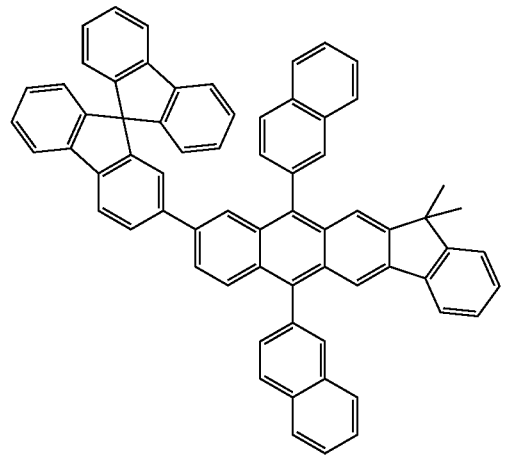
Inv 1-10
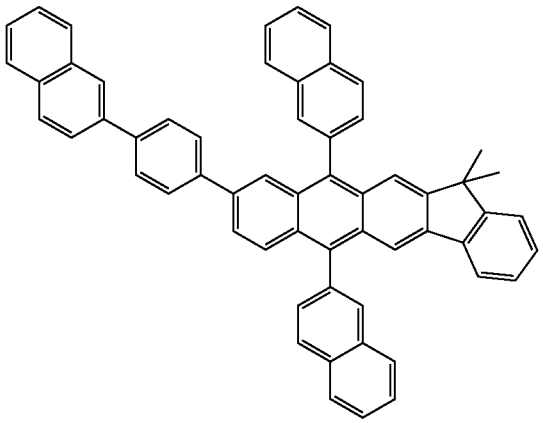
Inv 1-11
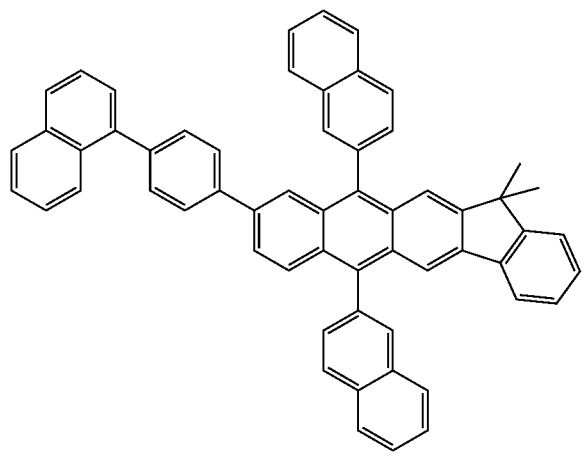
Inv 1-12
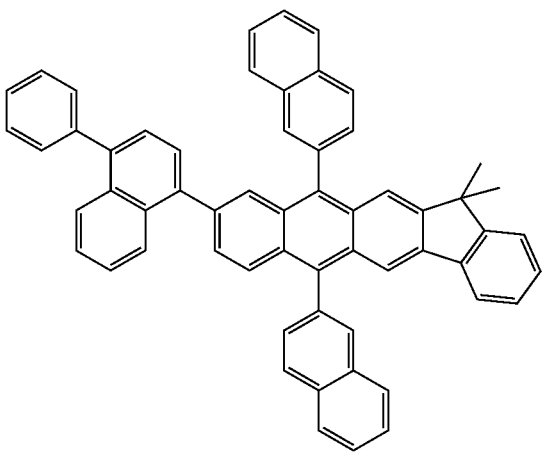

-continued
Inv 1-13
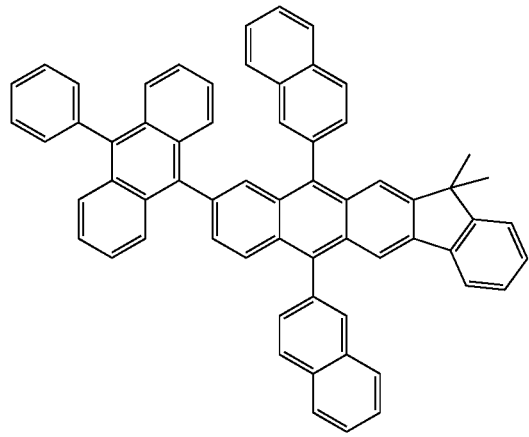
Inv 1-14
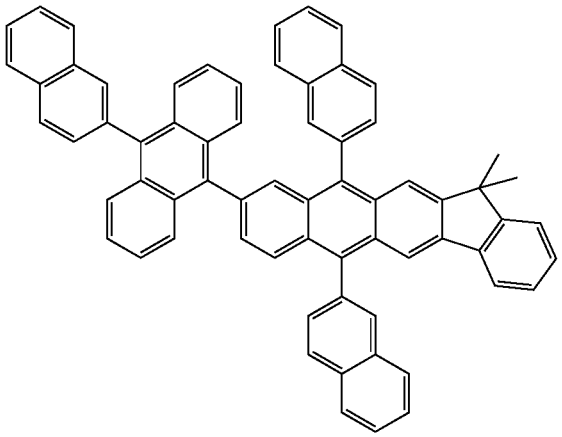
Inv 1-15
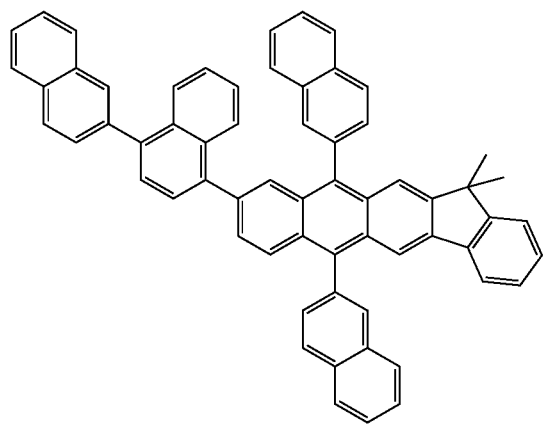
Inv 1-16
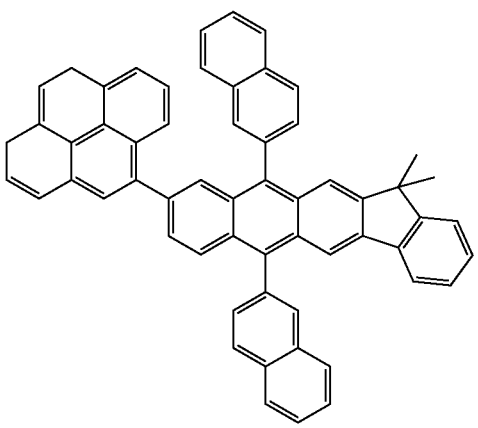
Inv 1-17
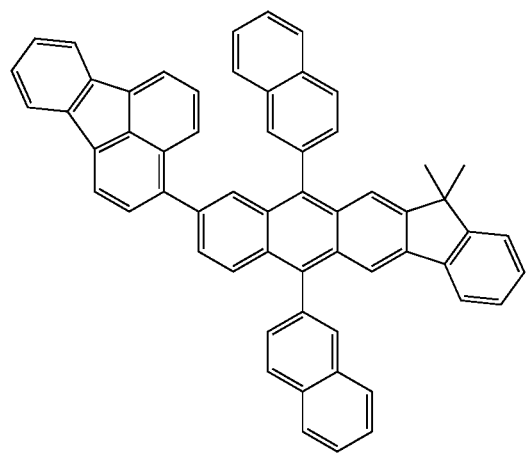
Inv 1-18
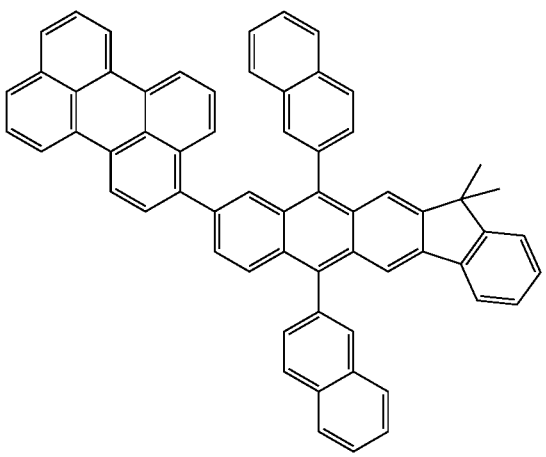

-continued
Inv 1-19
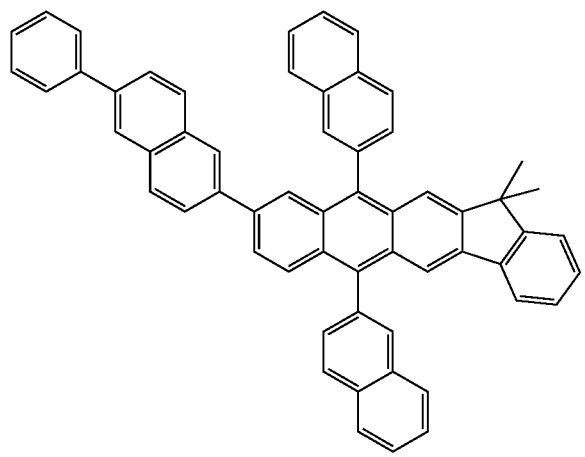
Inv 1-20
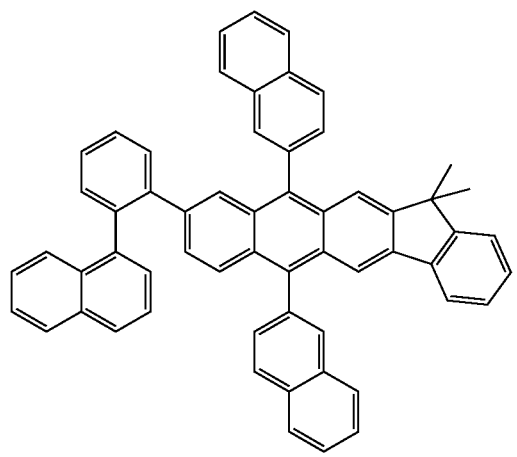
Inv 1-21
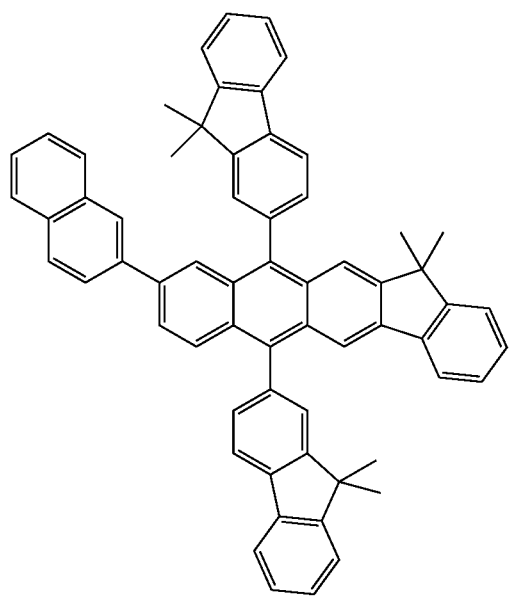
Inv 1-22
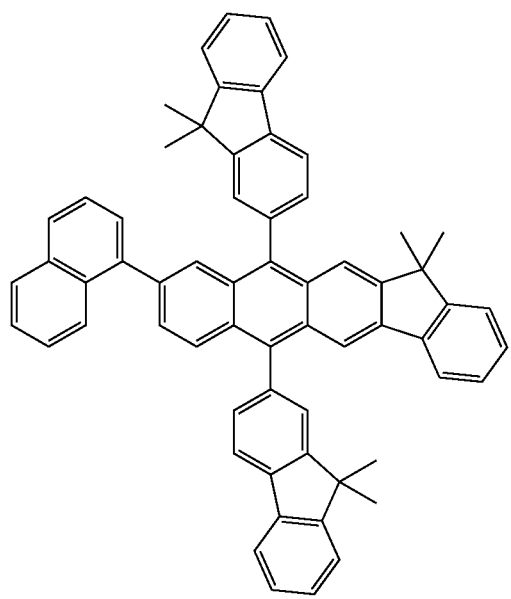
Inv 1-23
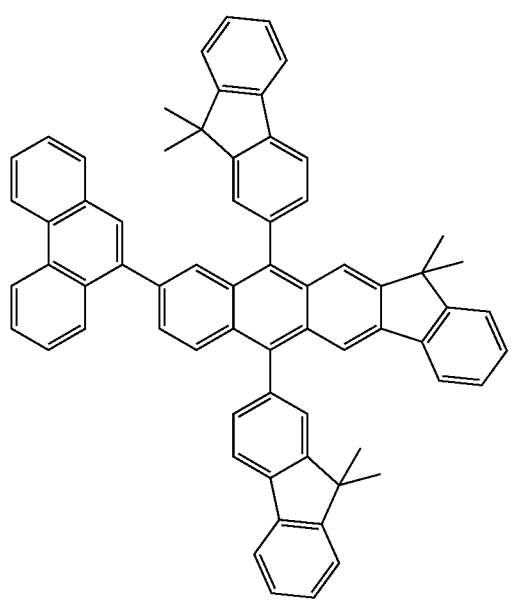
Inv 1-24
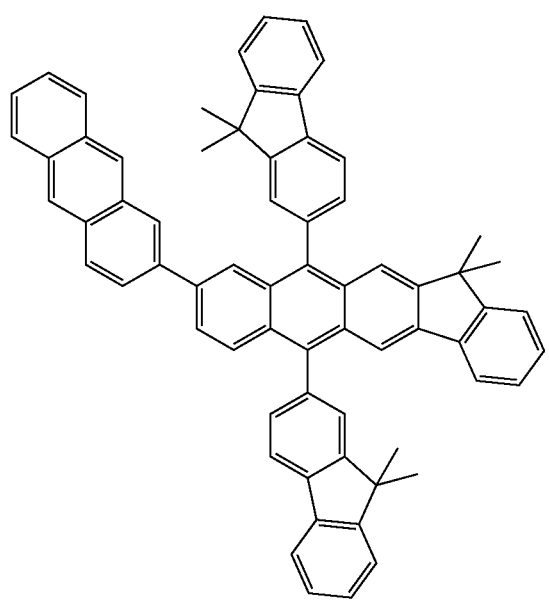

Inv 1-25
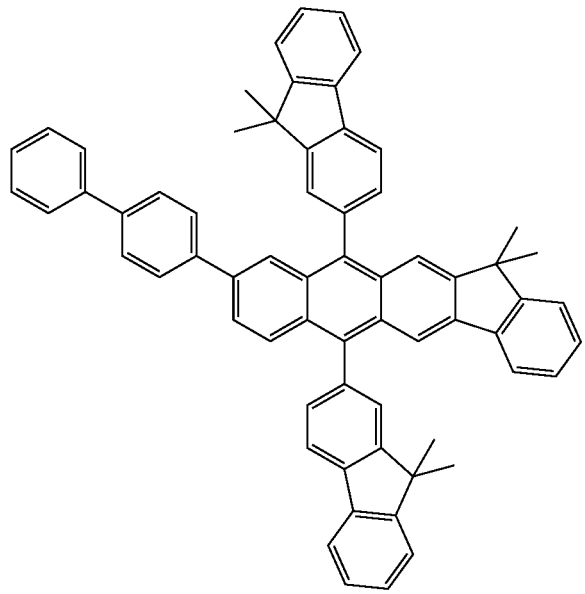
Inv 1-26
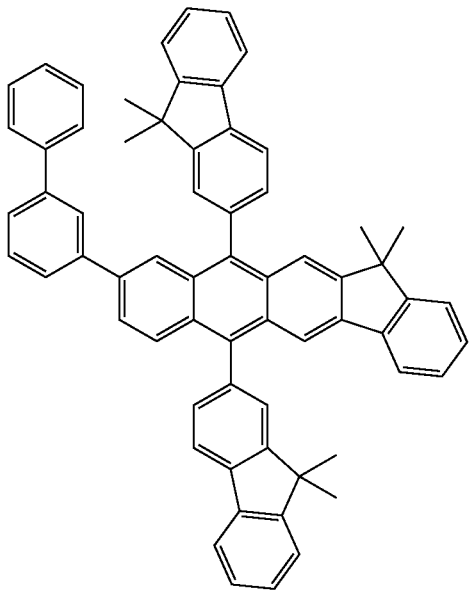
Inv 1-27
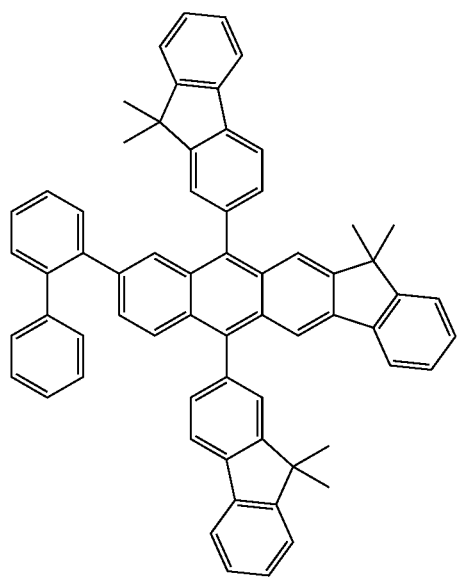
Inv 1-28
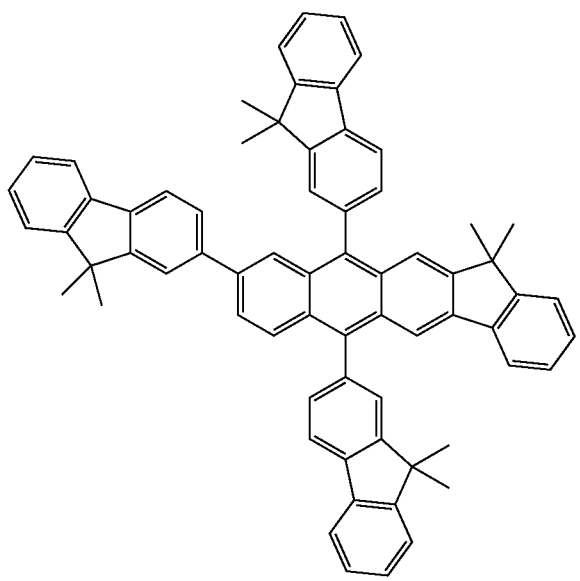

-continued
Inv 1-29
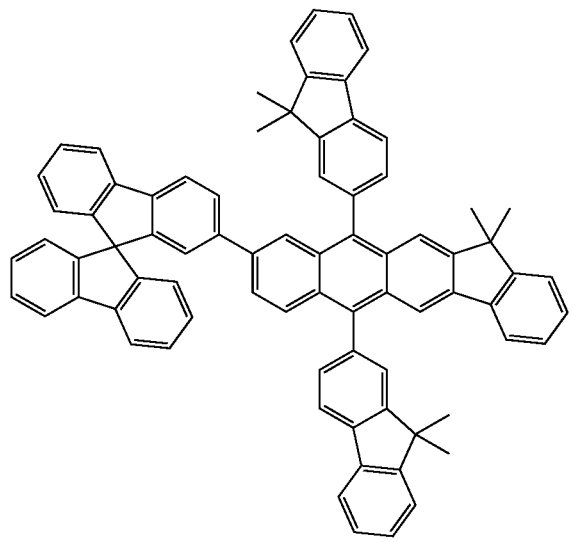
Inv 1-30
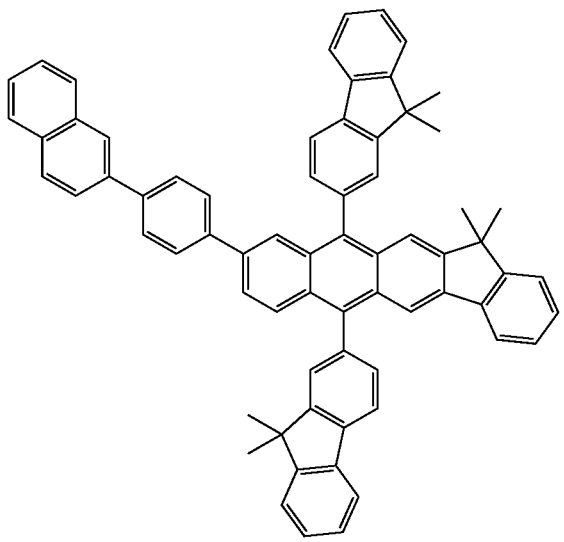
Inv 1-31
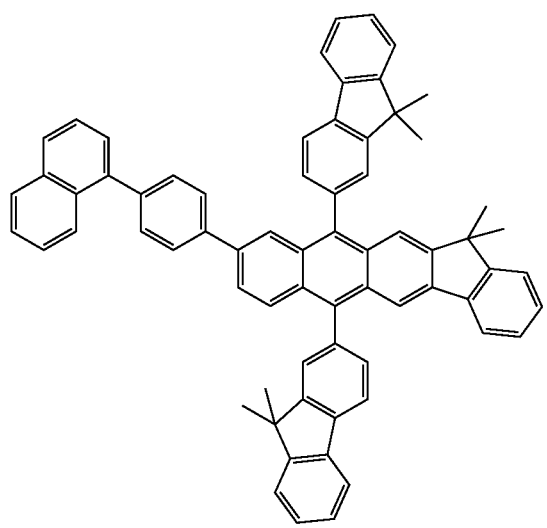
Inv 1-32
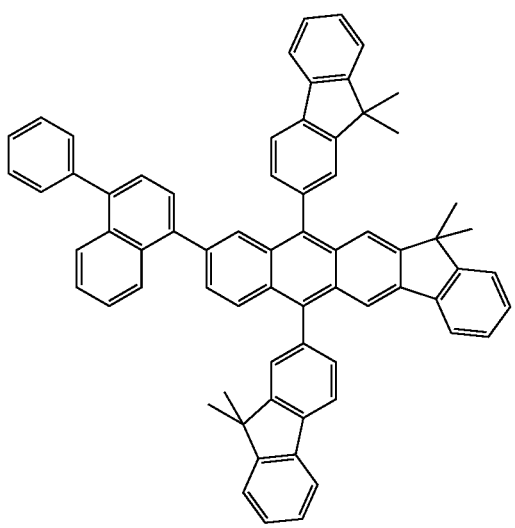
Inv 1-33
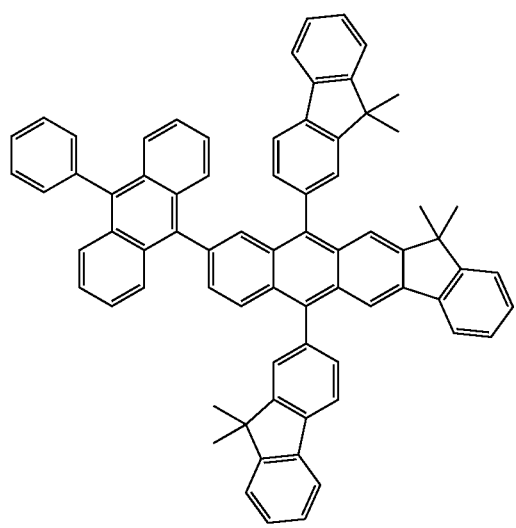
Inv 1-34
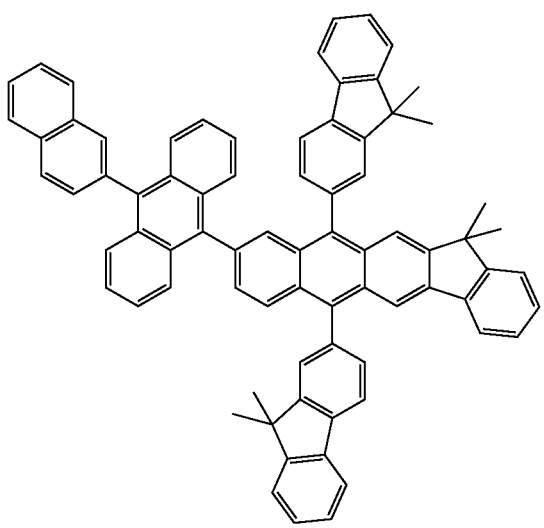

-continued
Inv 1-35
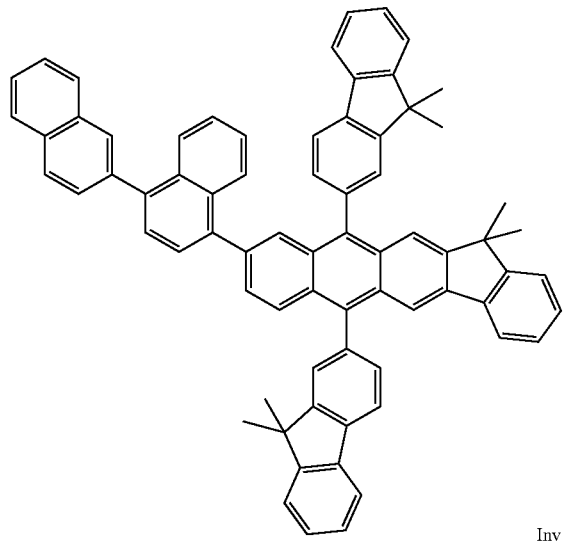
Inv 1-36
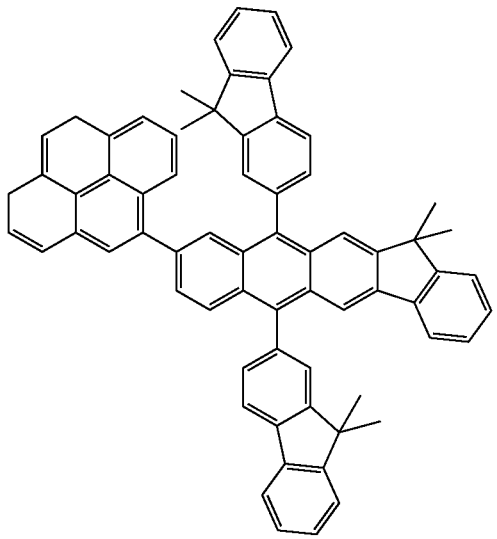
Inv 1-37
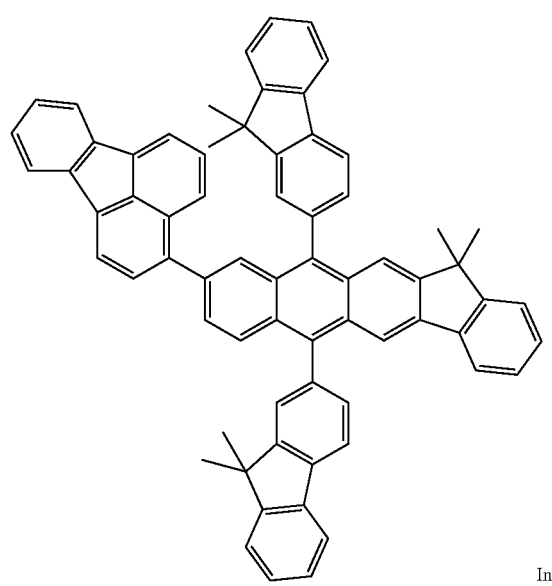
Inv 1-38
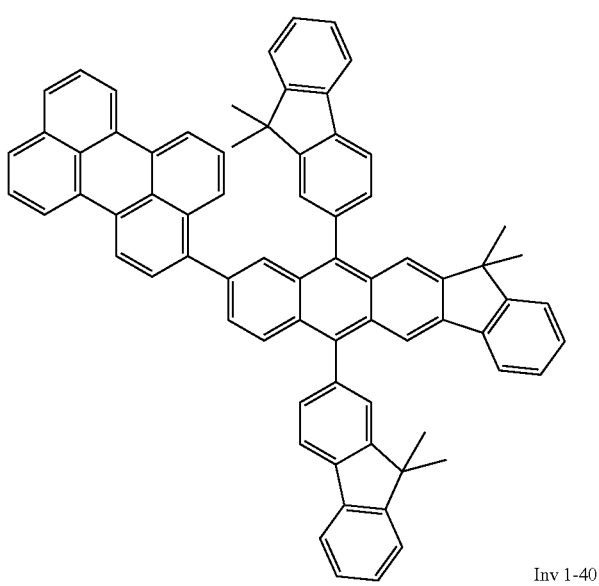
Inv 1-39
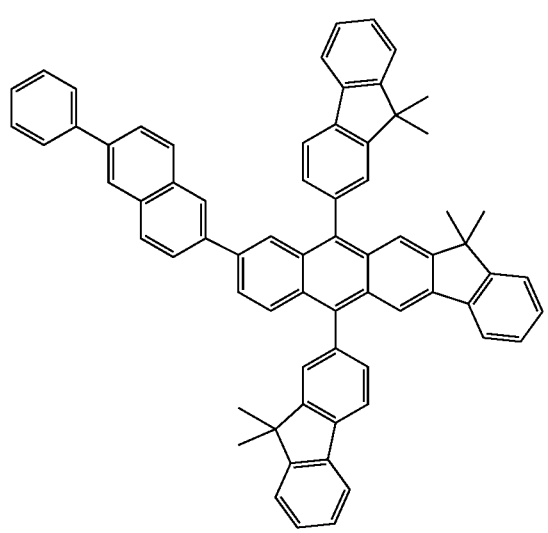
Inv 1-40
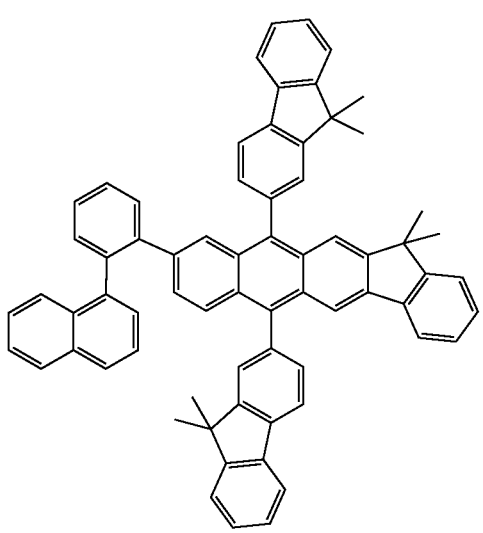

Inv 1-41
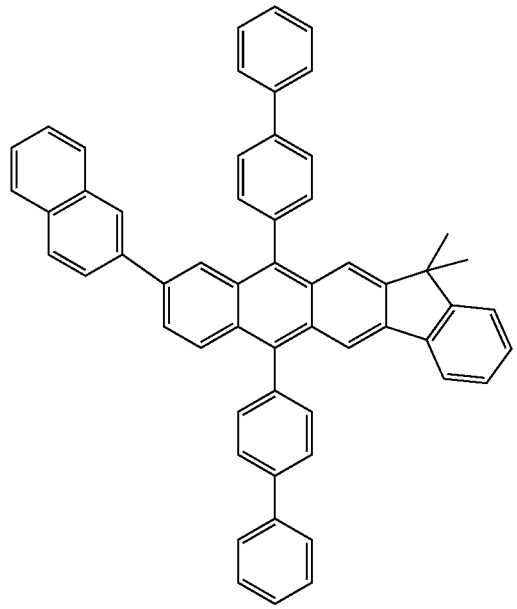
Inv 1-42
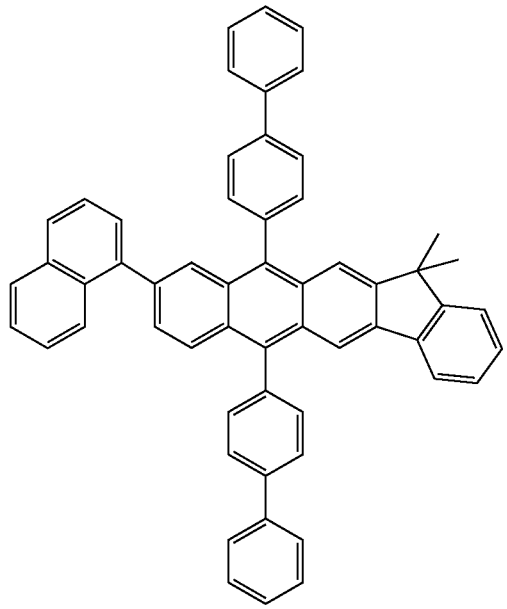
Inv 1-43
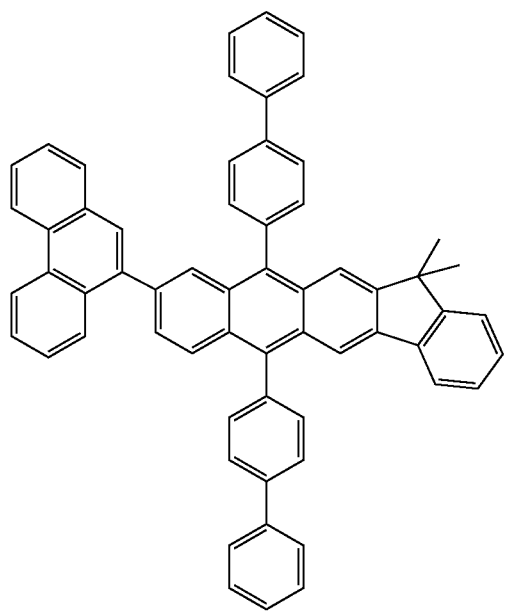
Inv 1-44
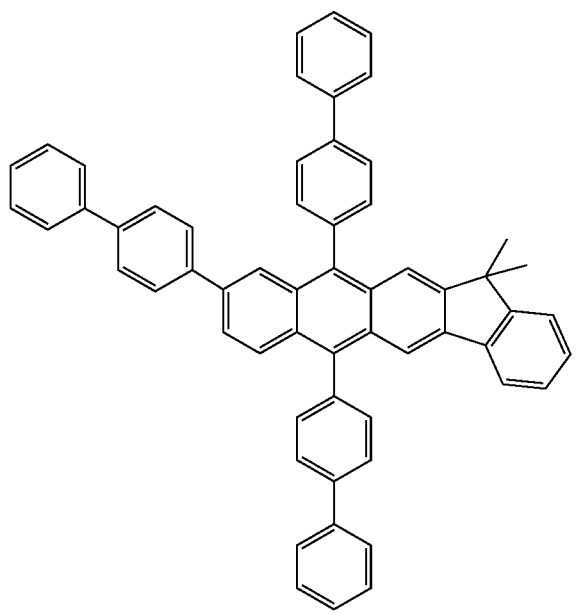

Inv 1-45
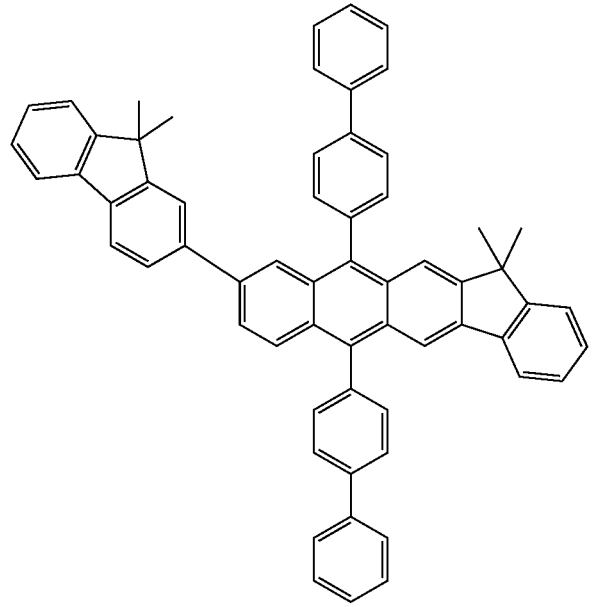
Inv 1-46
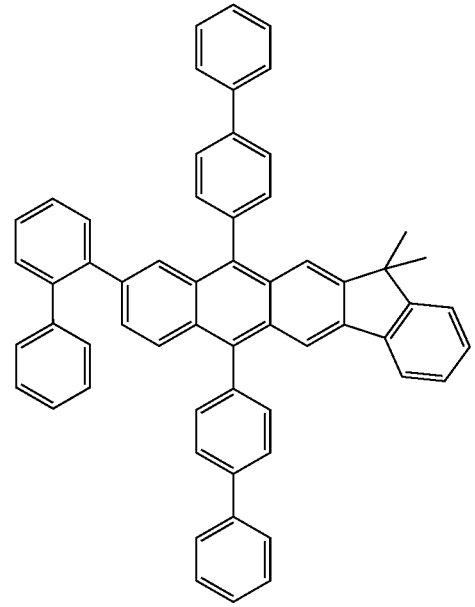
Inv 1-47
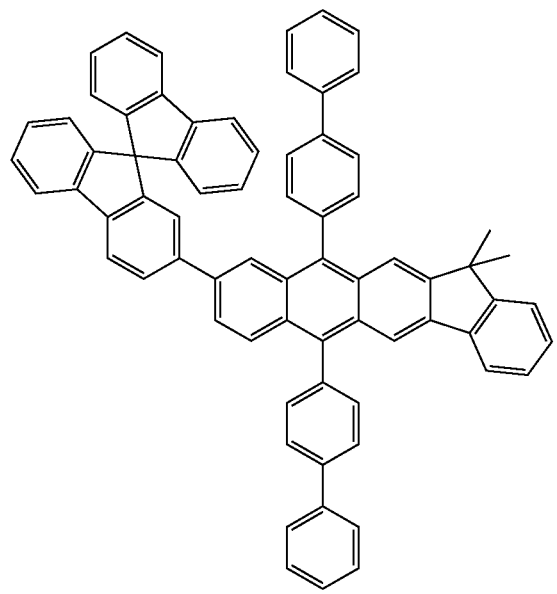
Inv 1-48
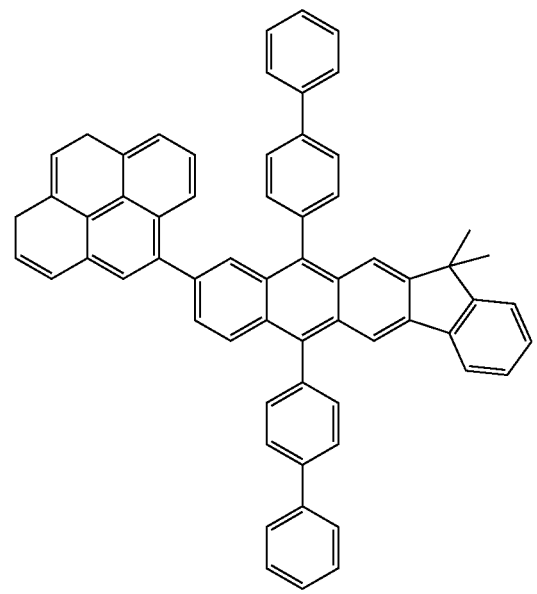

Inv 1-49
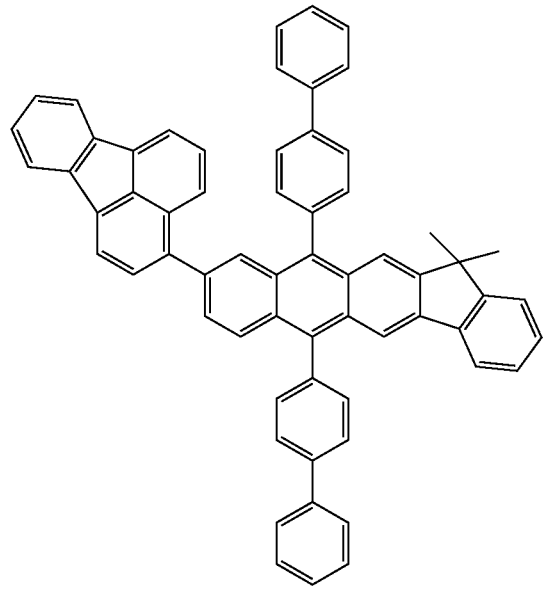
Inv 1-50
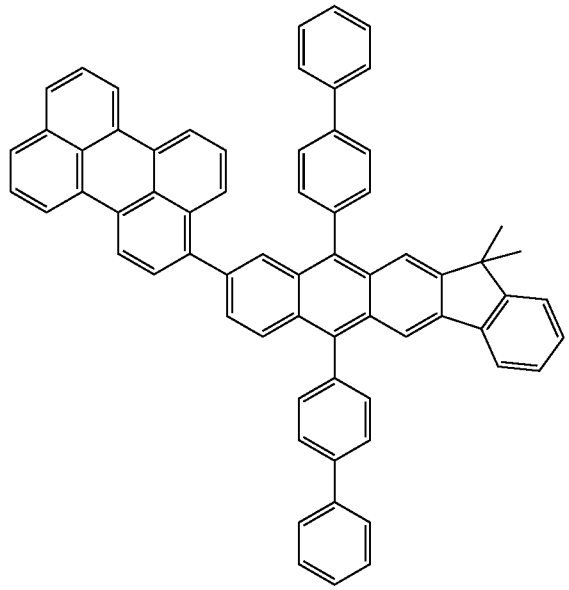
Inv 1-51
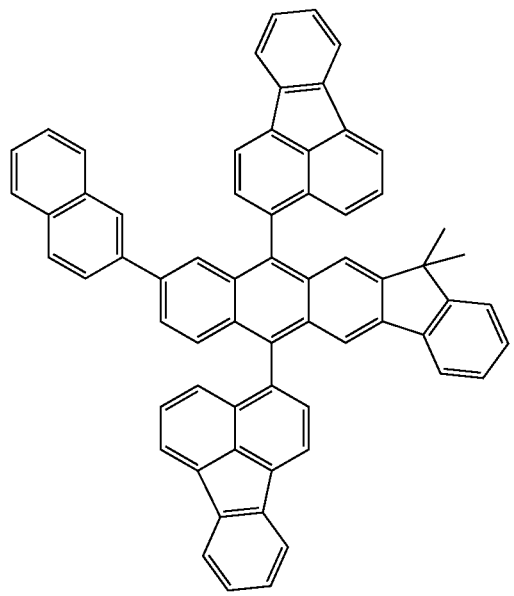
Inv 1-52
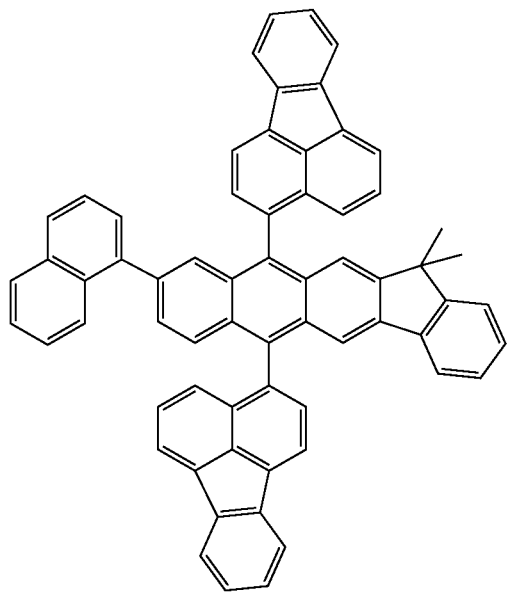

Inv 1-53
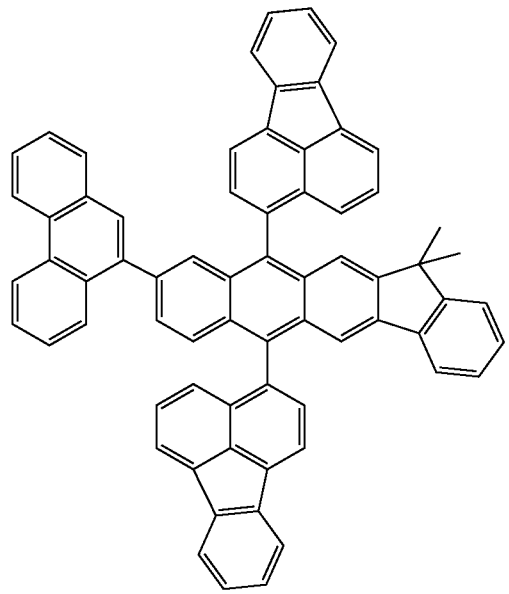
Inv 1-54
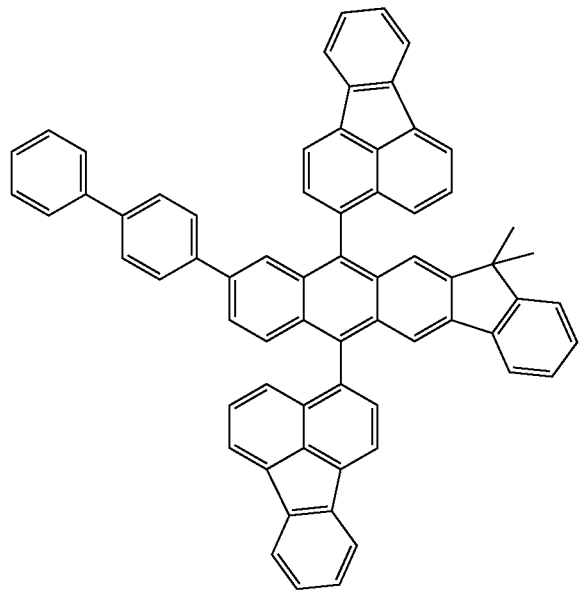
Inv 1-55
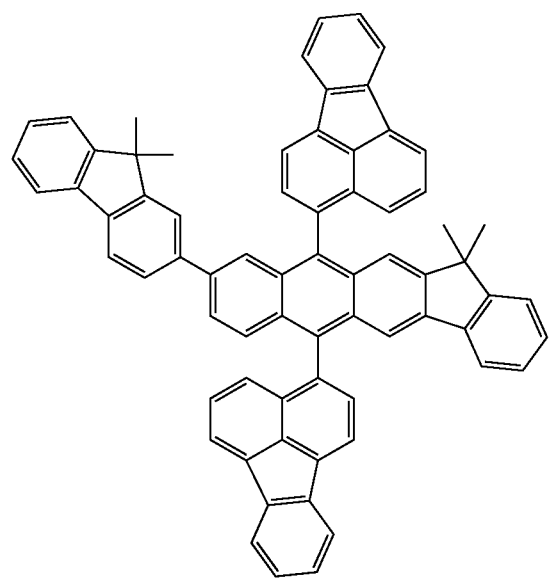
Inv 1-56
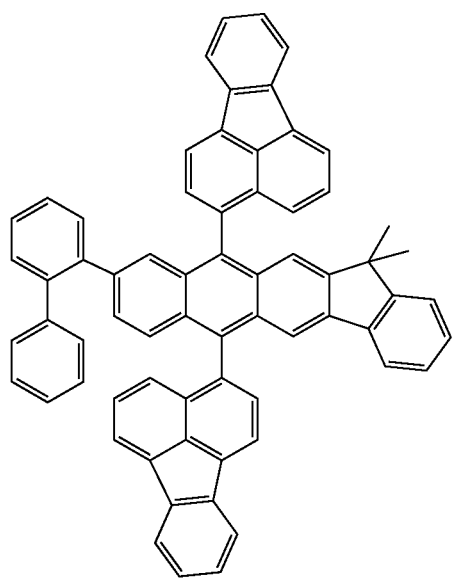

-continued
Inv 1-57
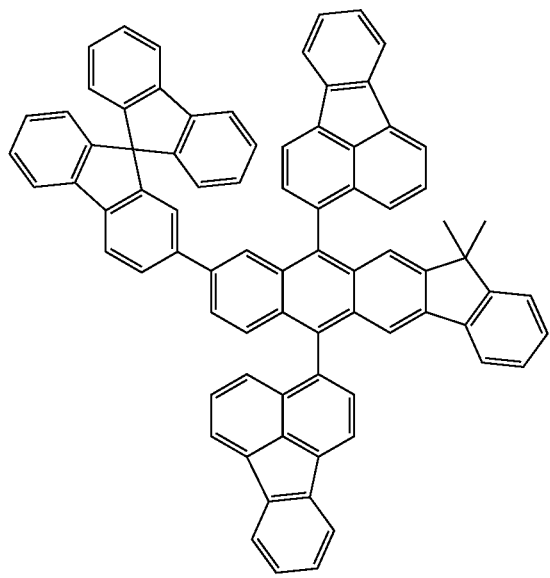
Inv 1-58
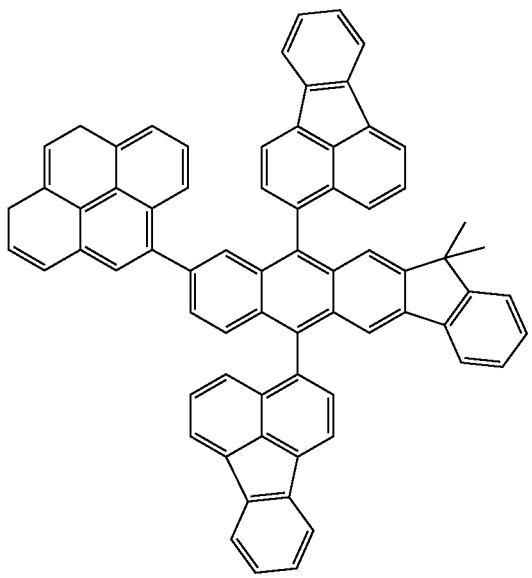
Inv 1-59
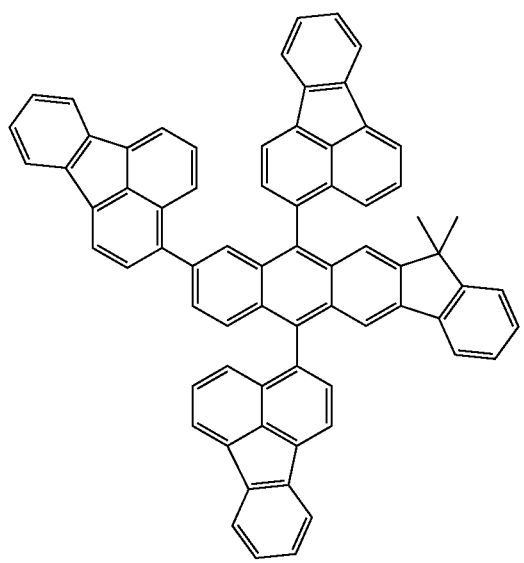
Inv 1-60
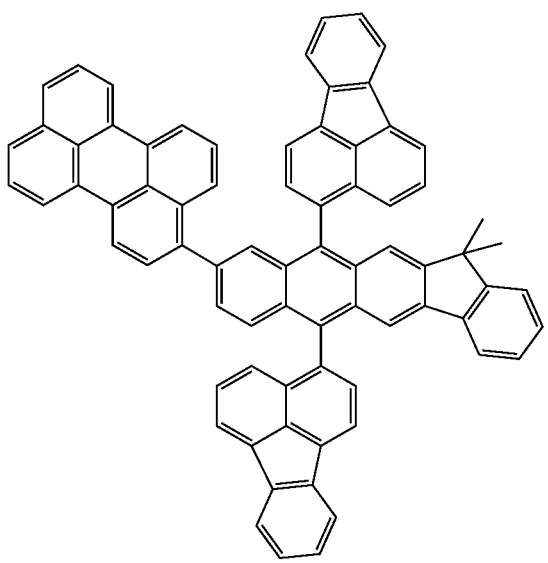
Inv 2-1
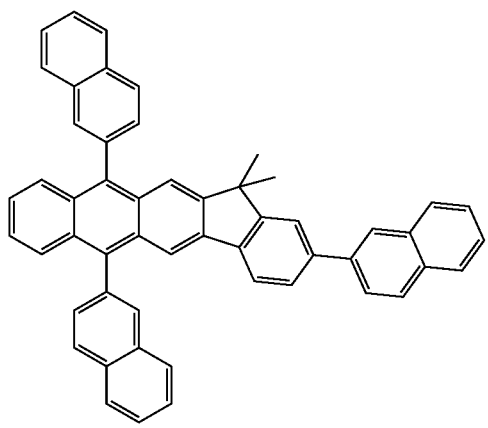
Inv 2-2
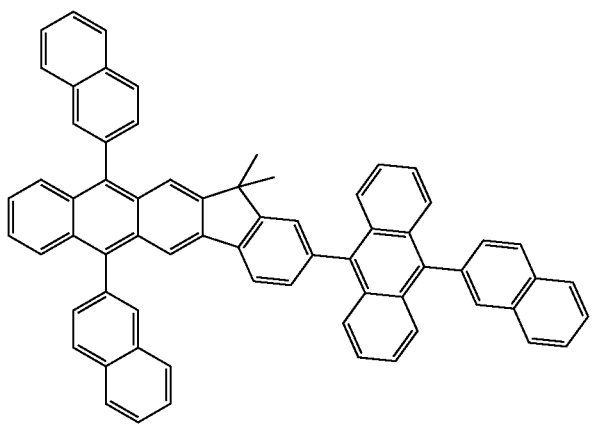

-continued
Inv 2-3
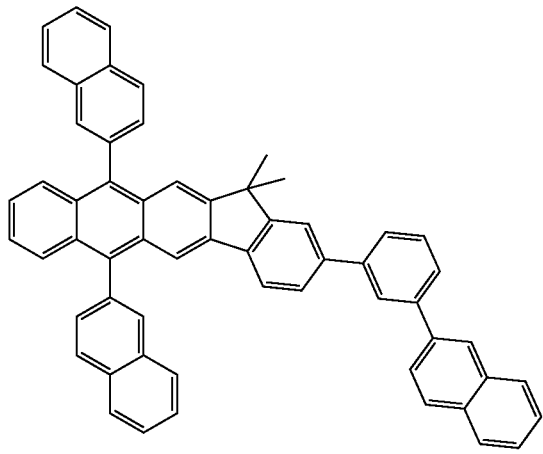
Inv 2-4
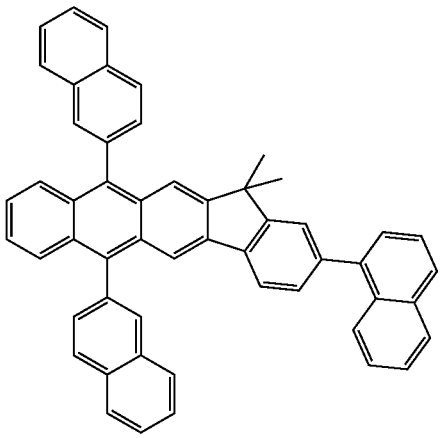
Inv 2-5
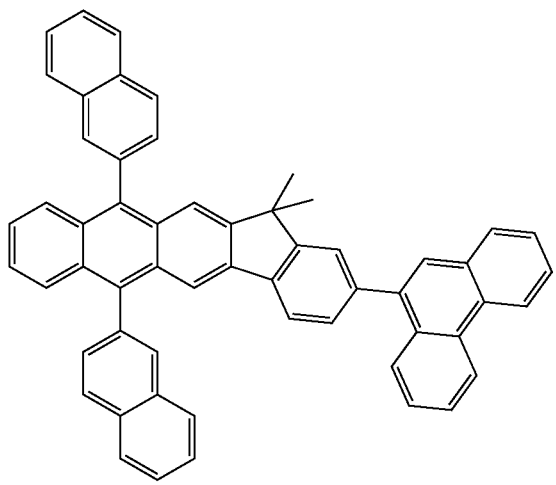
Inv 2-6
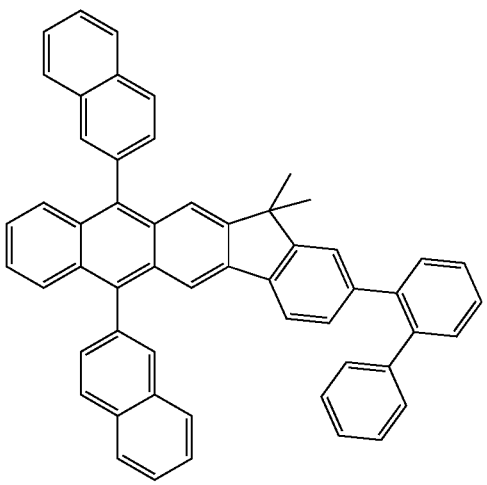
Inv 2-7
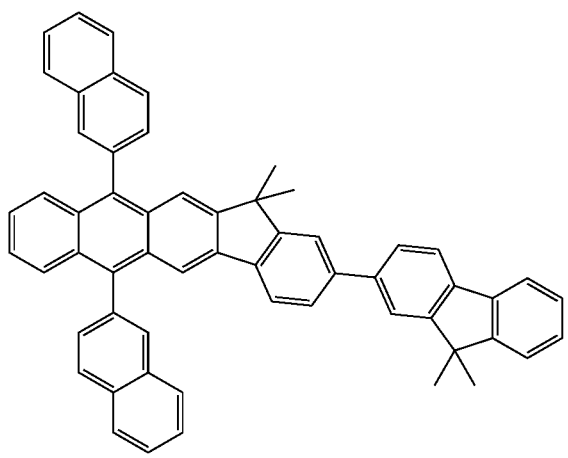
Inv 2-8
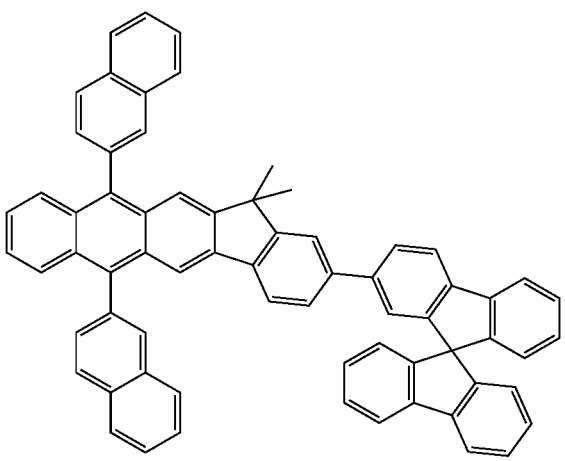

-continued
Inv 2-9
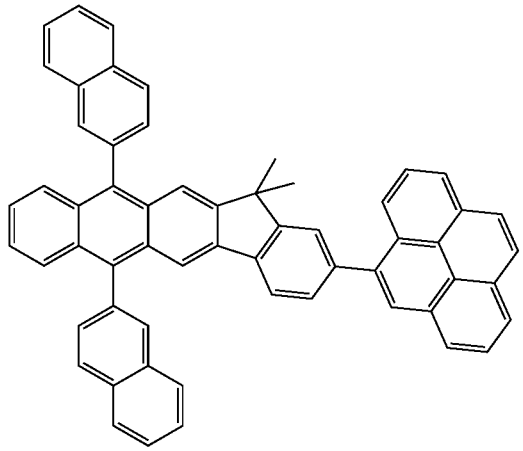
Inv 2-10
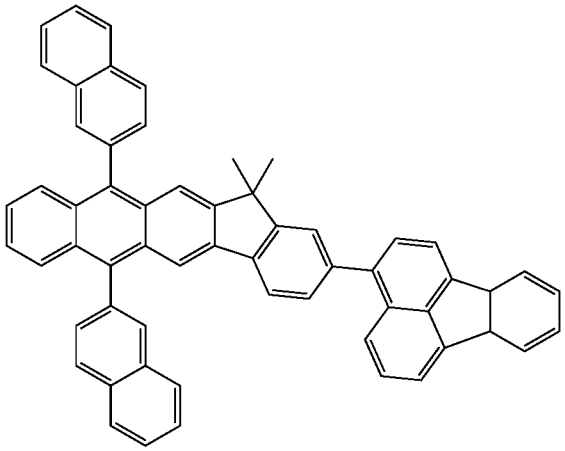
Inv 2-11
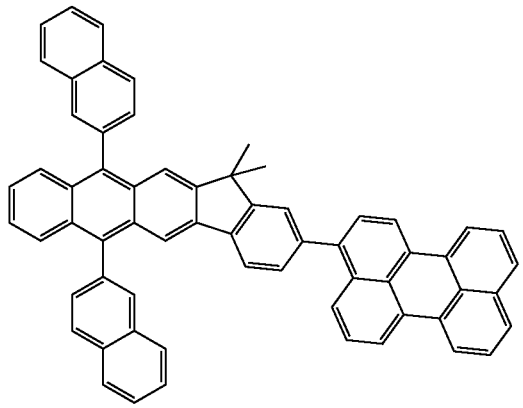
Inv 2-12
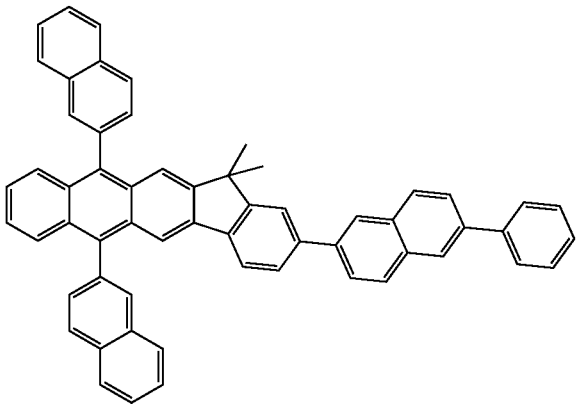
Inv 2-13
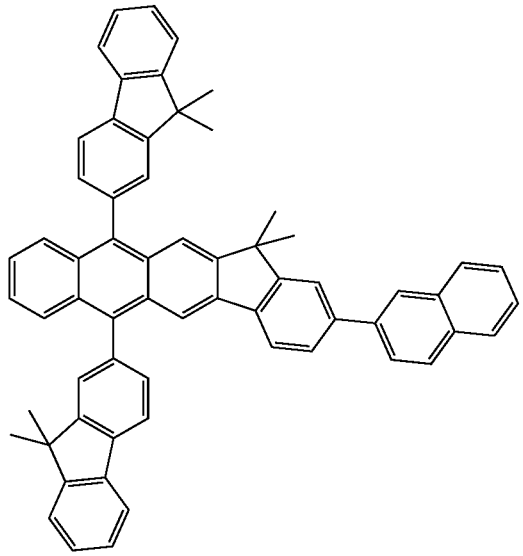
Inv 2-14
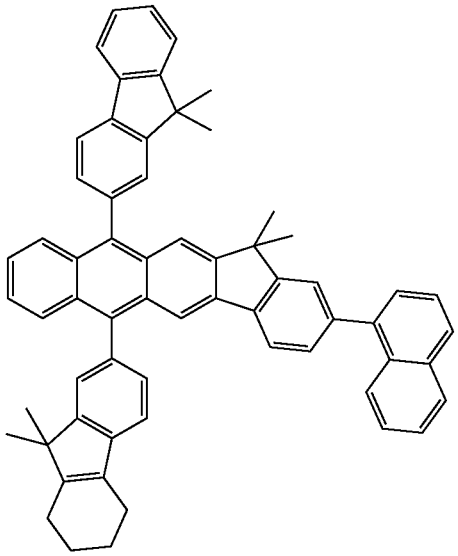

-continued
Inv 2-15
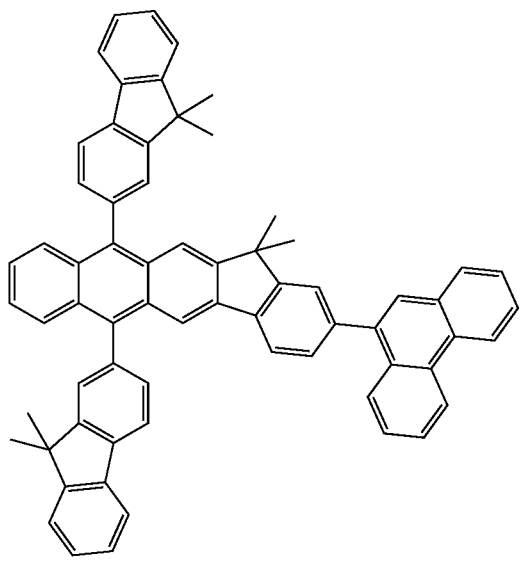
Inv 2-16
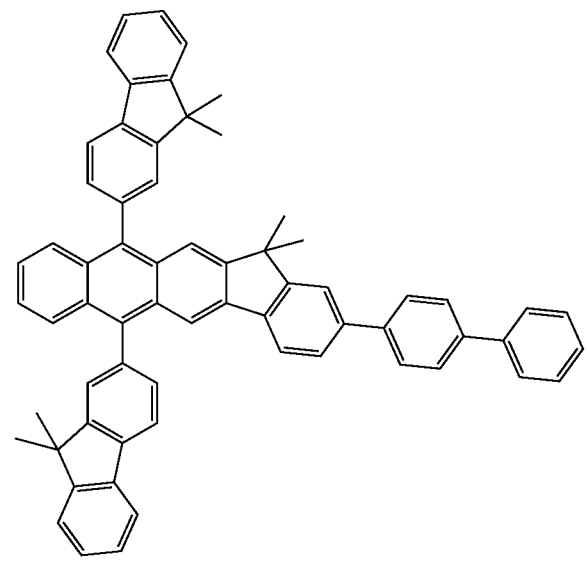
Inv 2-17
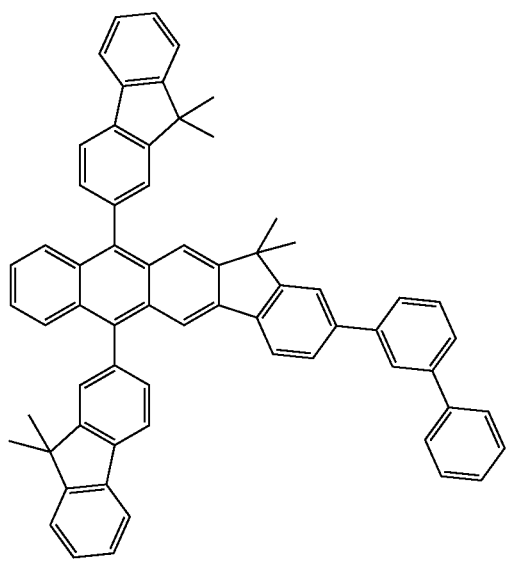
Inv 2-18
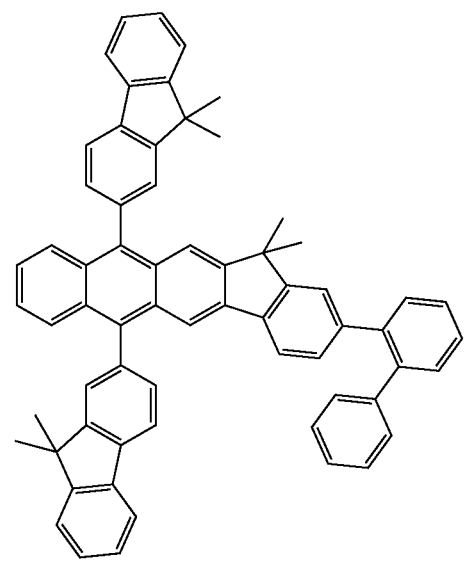
Inv 2-19
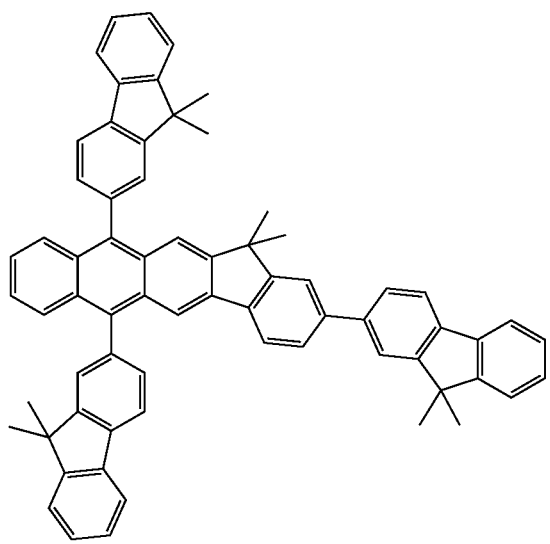
Inv 2-20
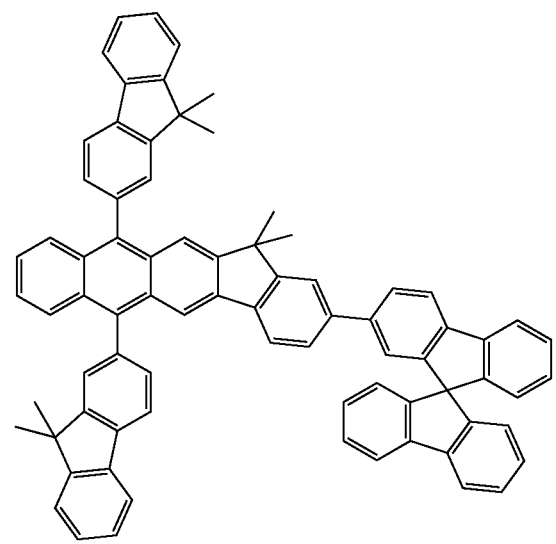

-continued
Inv 2-21
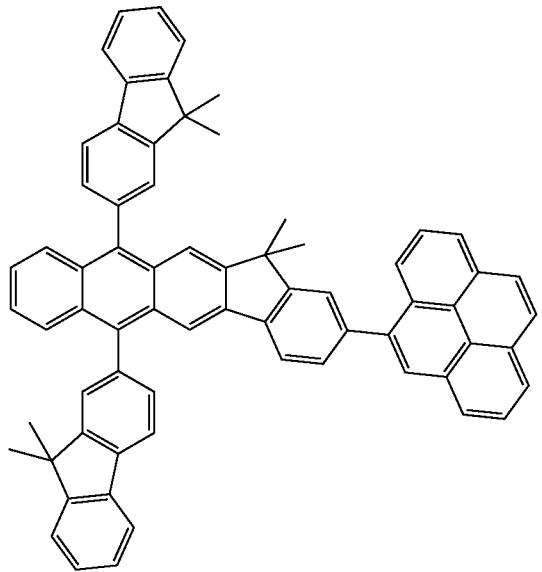
Inv 2-22
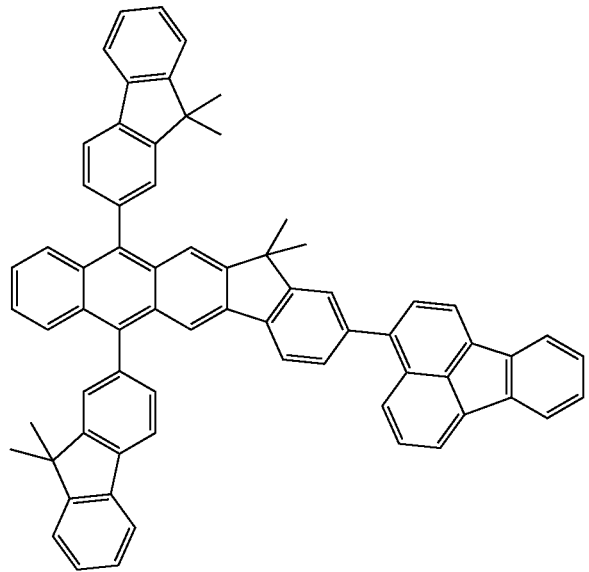
Inv 2-23
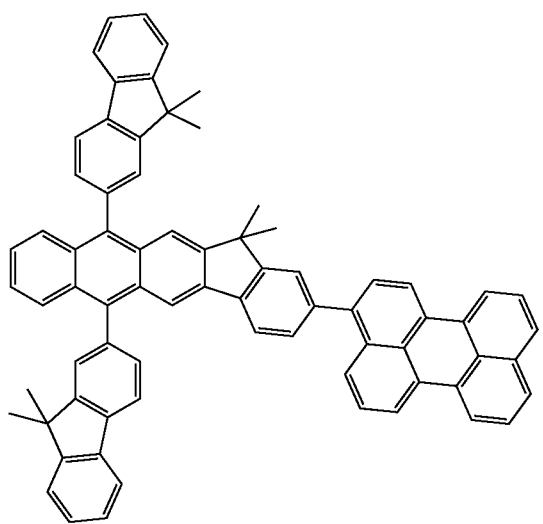
Inv 2-24
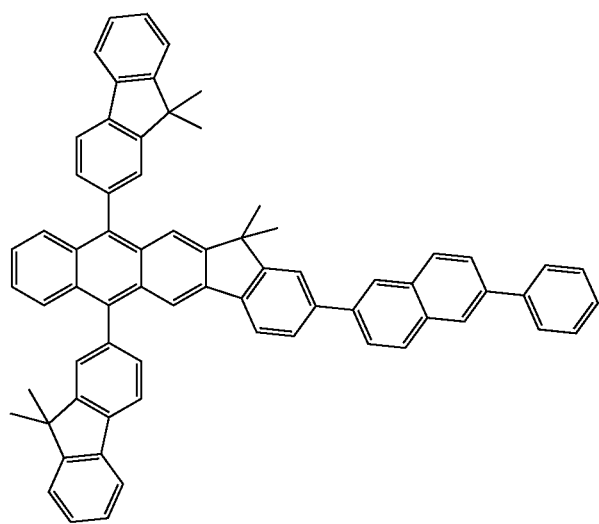

Inv 2-25
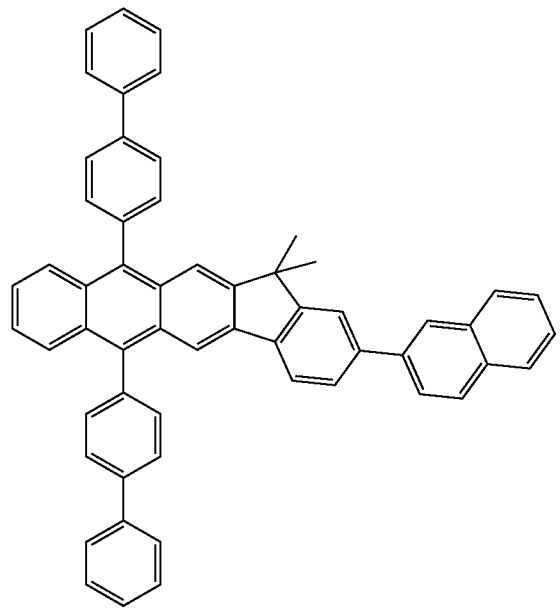
Inv 2-26
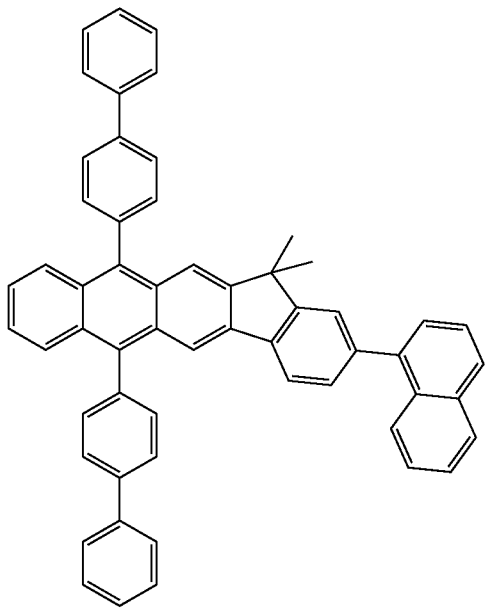
Inv 2-27
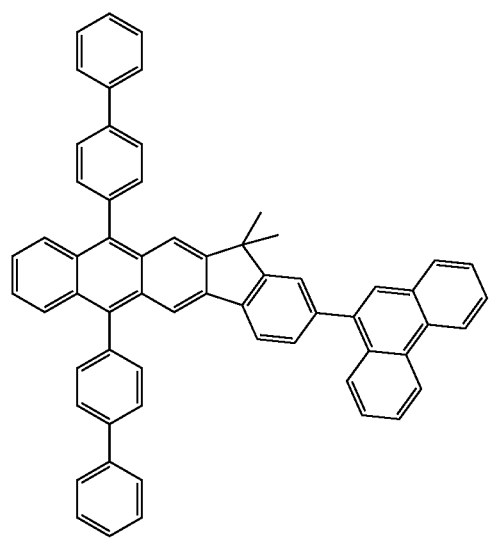
Inv 2-28
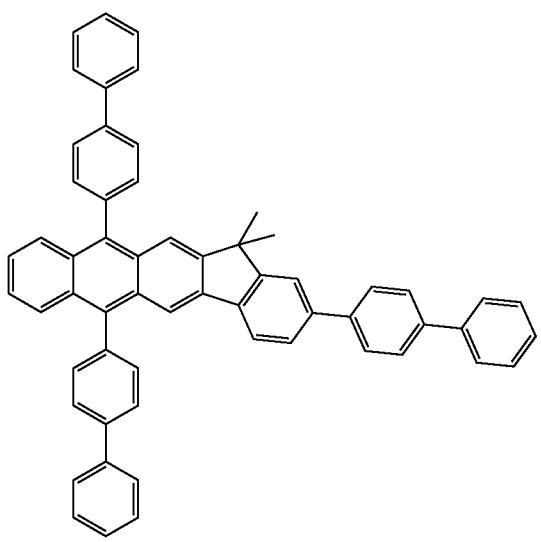

Inv 2-29
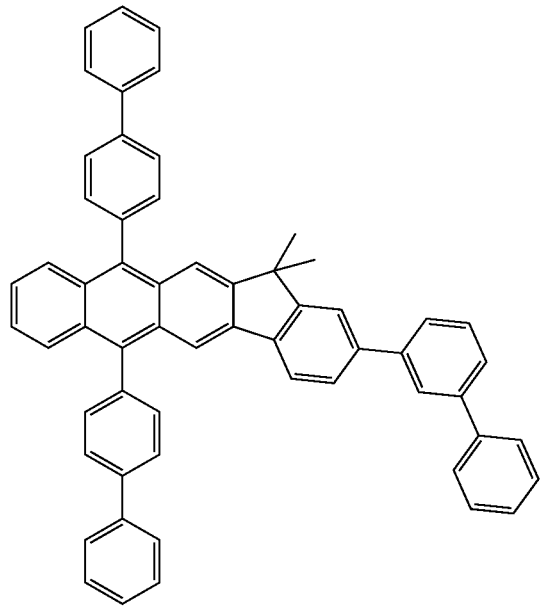
Inv 2-30
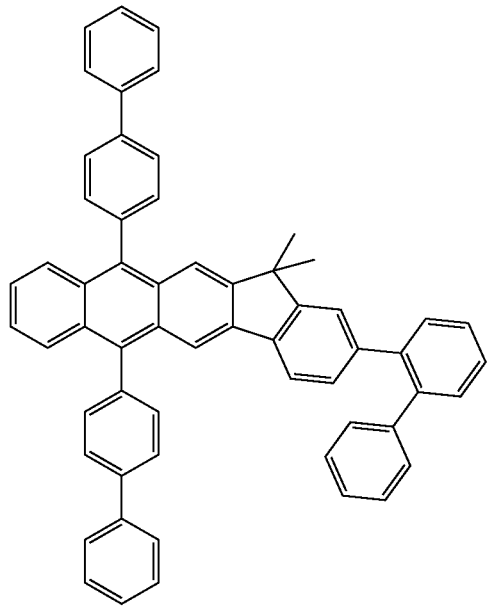
Inv 2-31
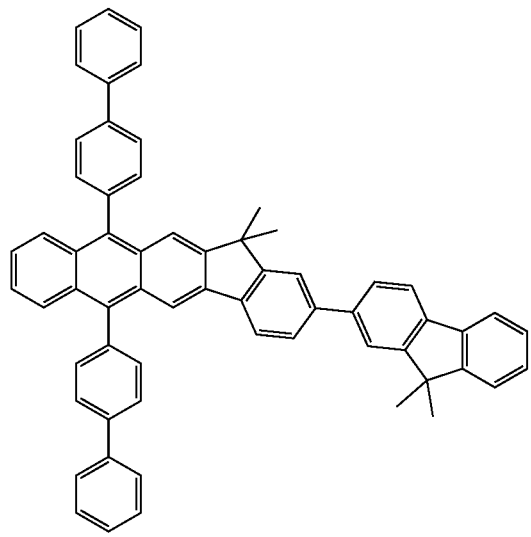
Inv 2-32
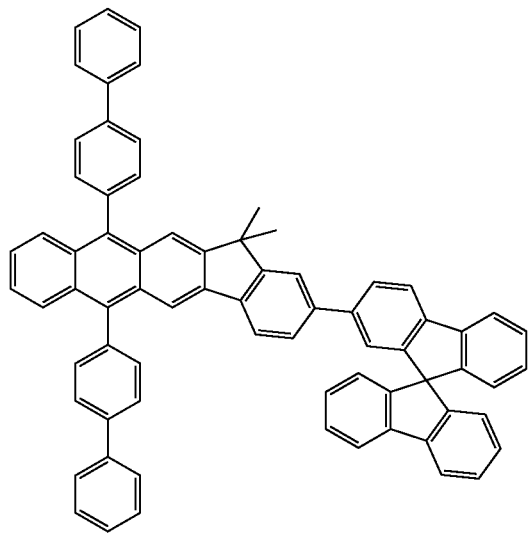

Inv 2-33
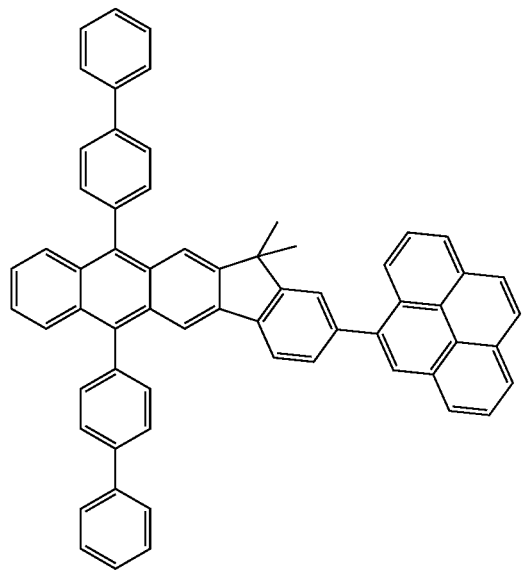
Inv 2-34
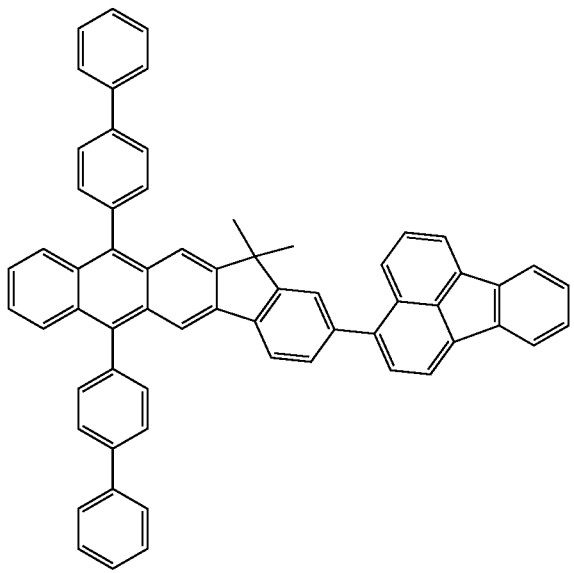
Inv 2-35
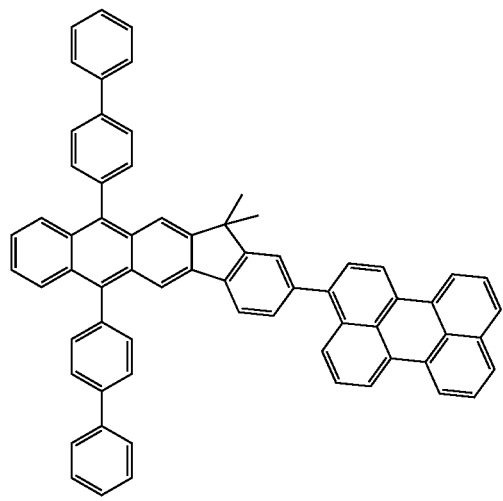
Inv 2-36
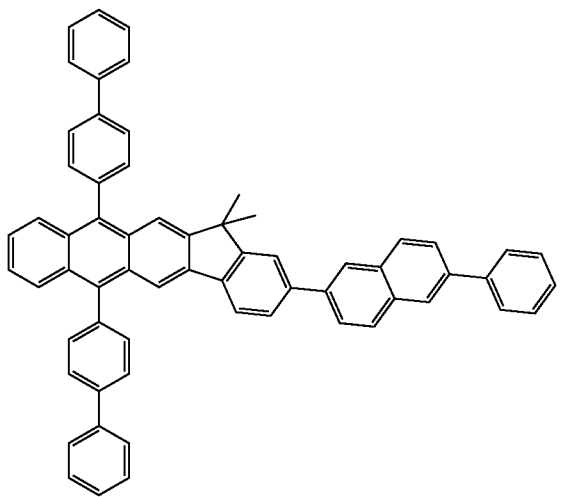
Inv 2-37
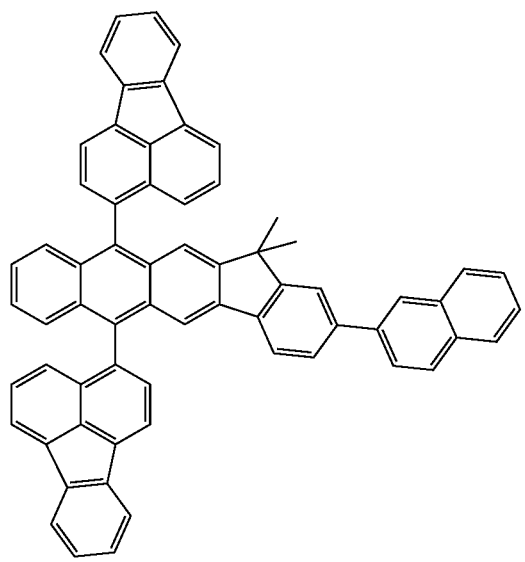
Inv 2-38
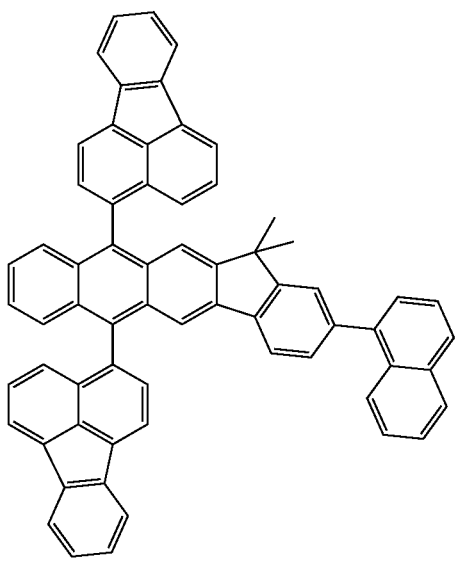

-continued
Inv 2-39
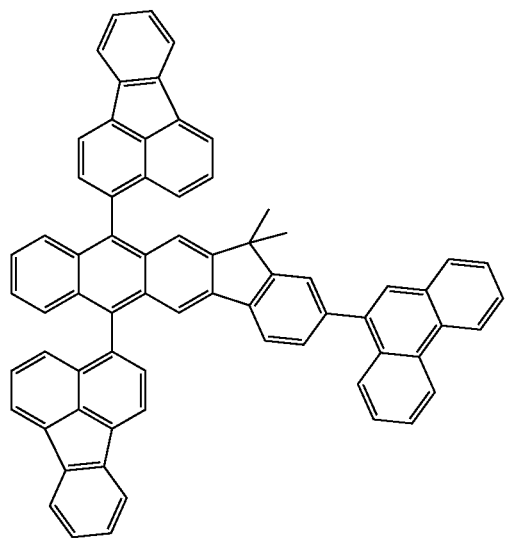
Inv 2-40
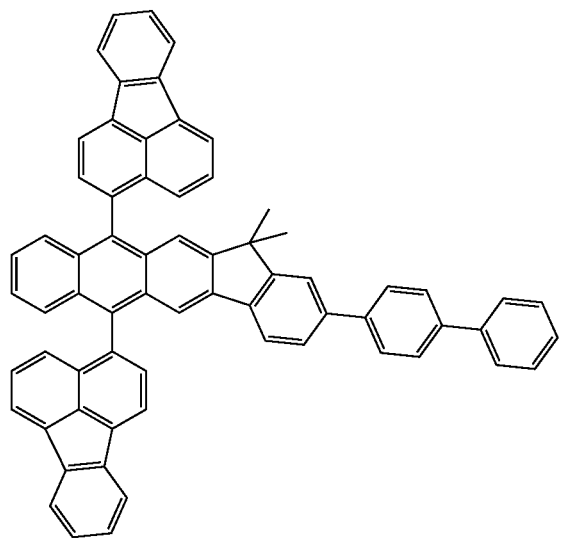
Inv 2-41
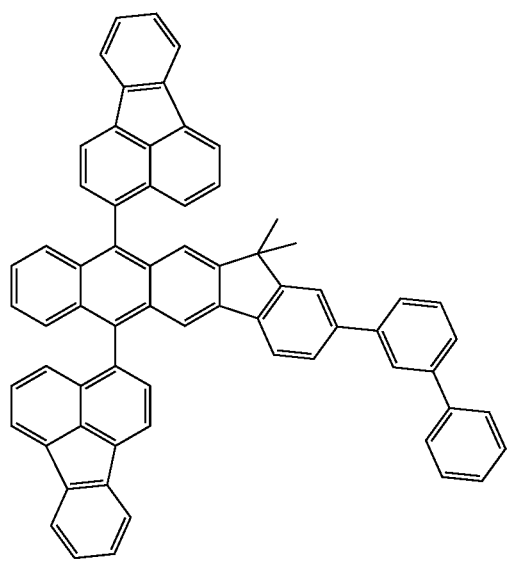
Inv 2-42
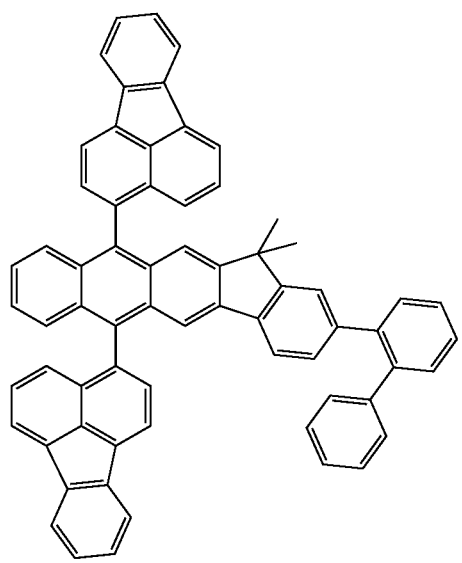
Inv 2-43
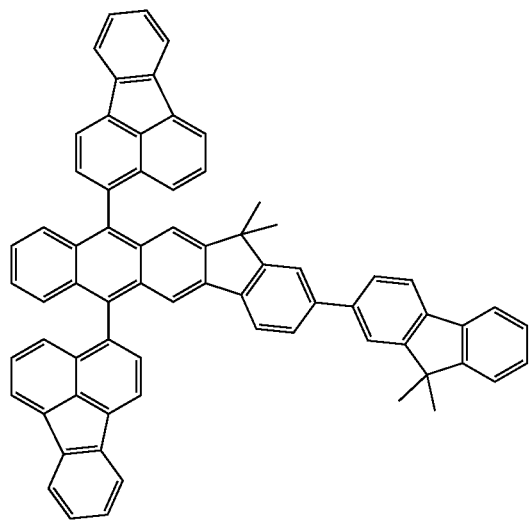
Inv 2-44
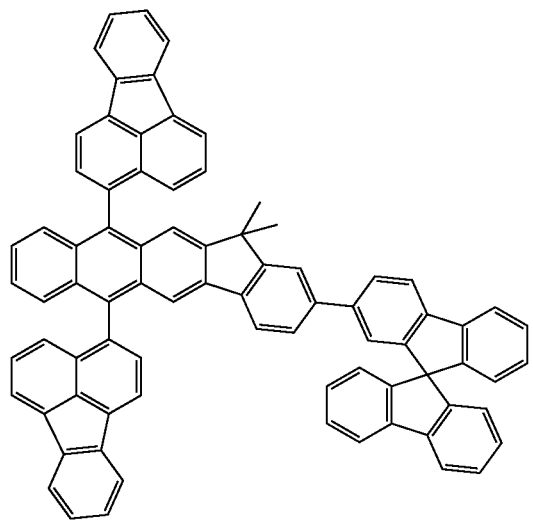

-continued
Inv 2-45
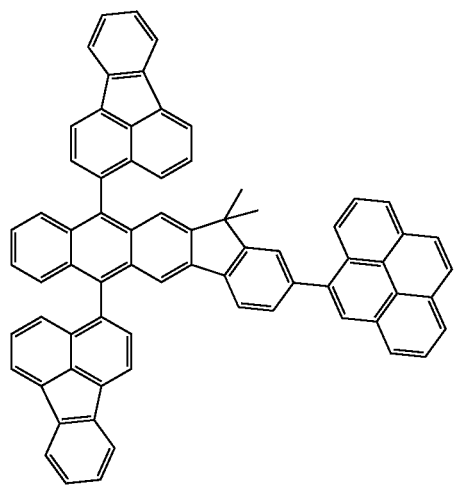
Inv 2-46
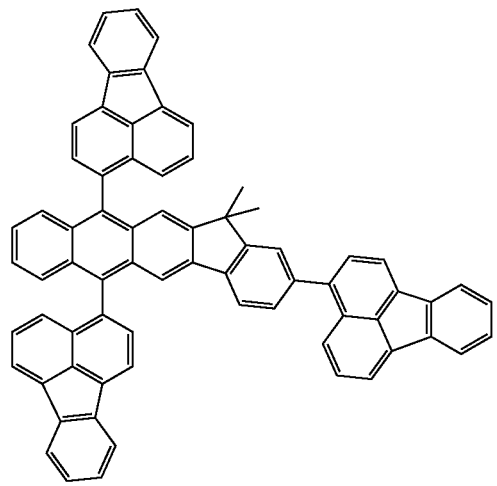
Inv 2-47
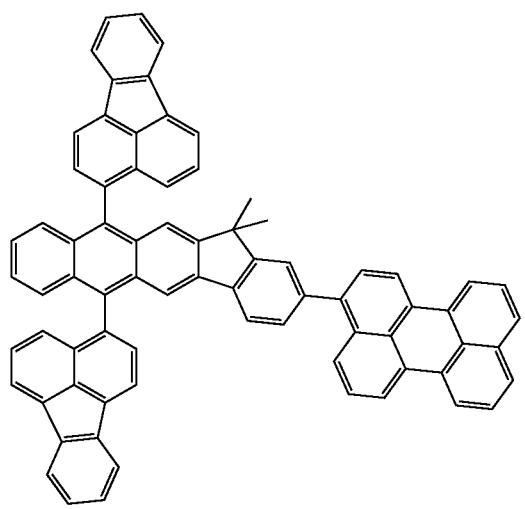
Inv 2-48
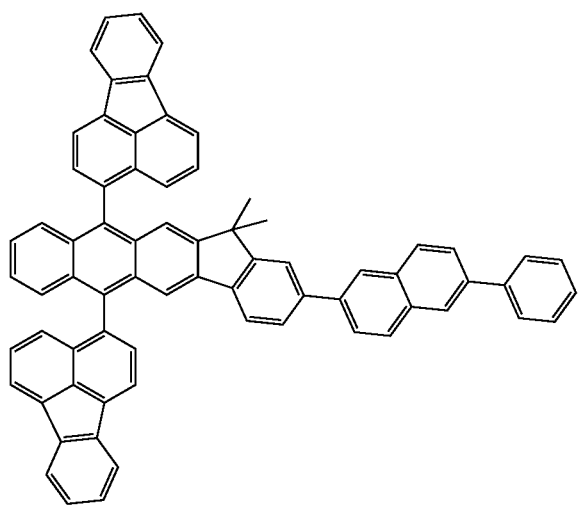
Inv-3-1
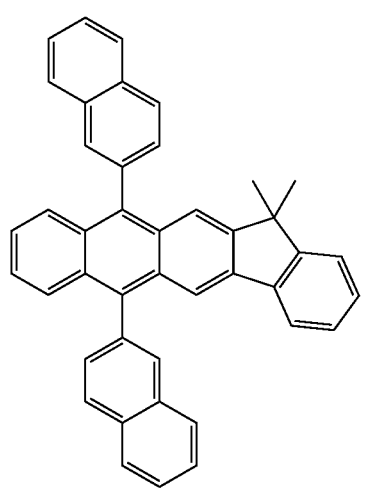
Inv-3-2
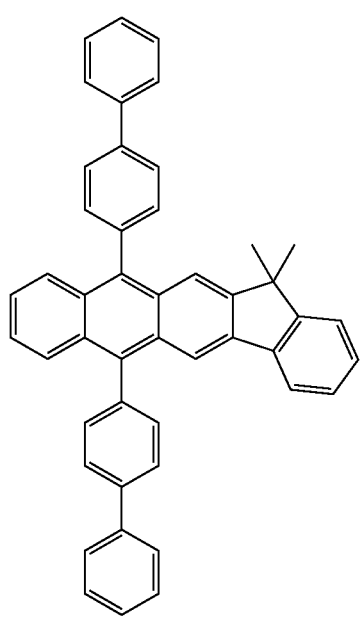

-continued
Inv-3-3
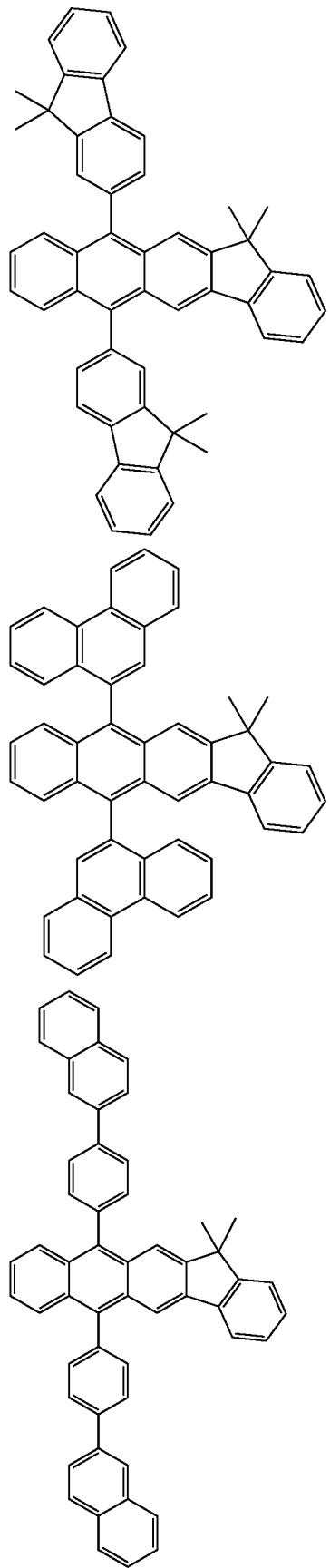
Inv-3-4
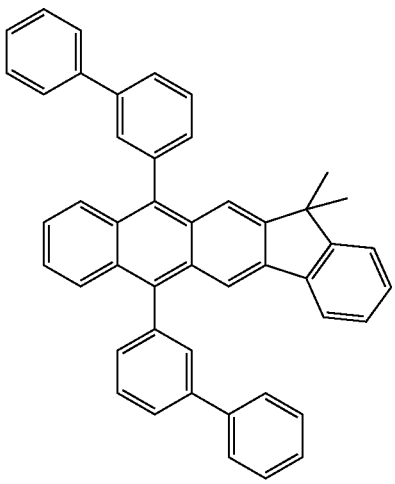
Inv-3-5
Inv-3-6
Inv-3-7
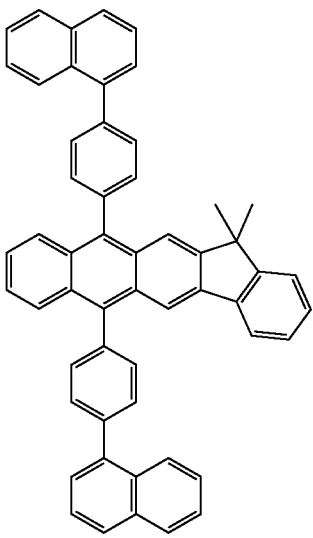

-continued
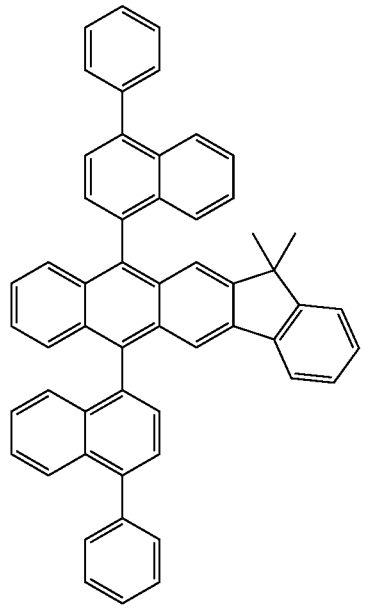
Inv-3-8
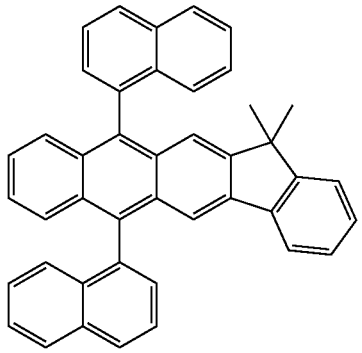
Inv-3-9
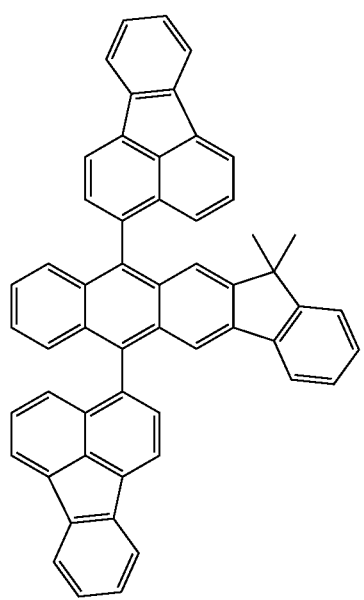
Inv-3-10
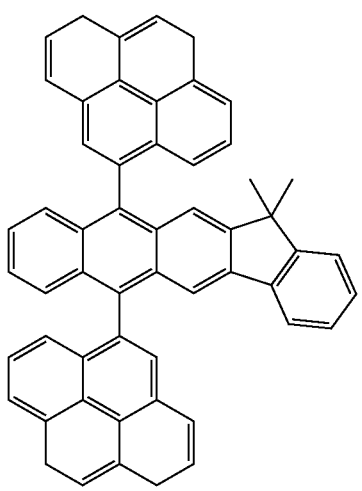
Inv-3-11

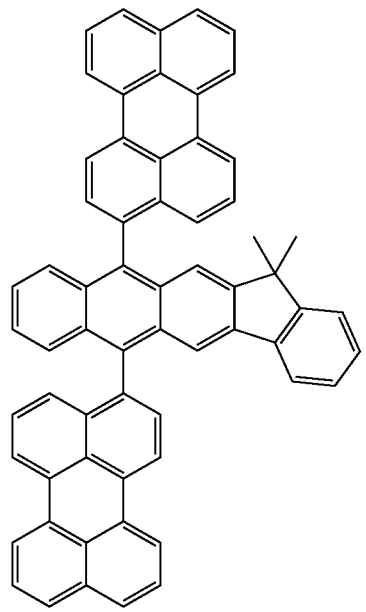
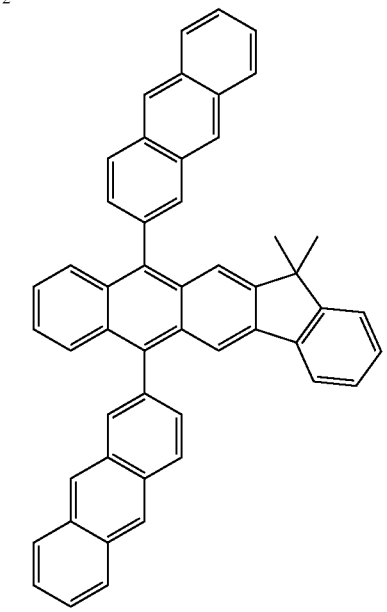
Inv-3-12
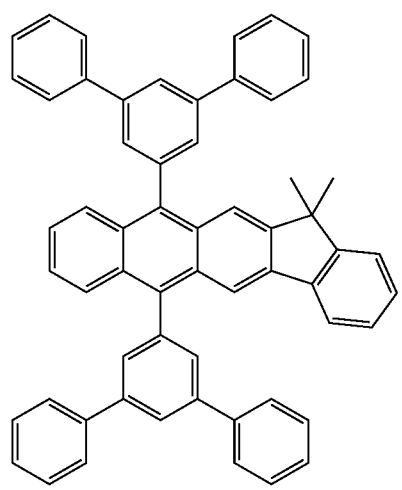
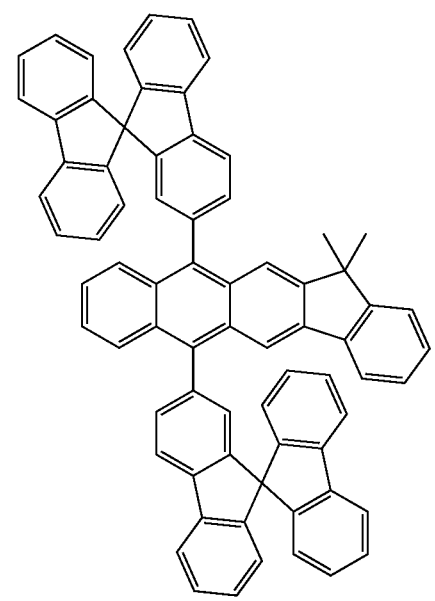
Inv-3-13
Inv-3-14
Inv-3-14-1

-continued
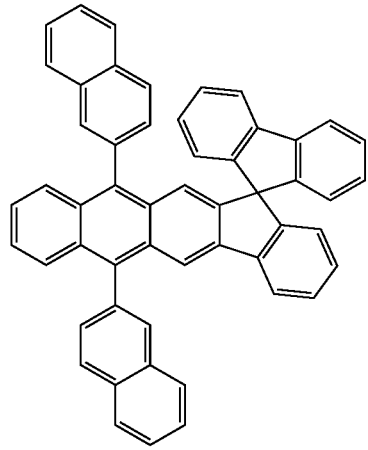
Inv-3-15
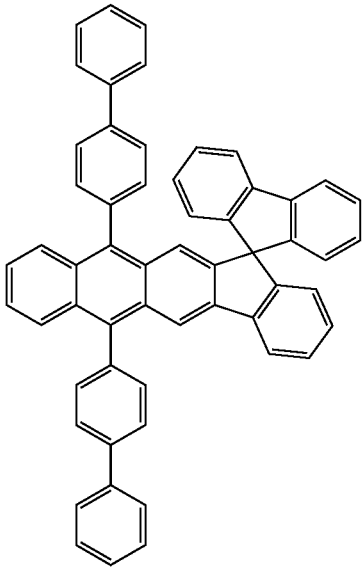
Inv-3-16
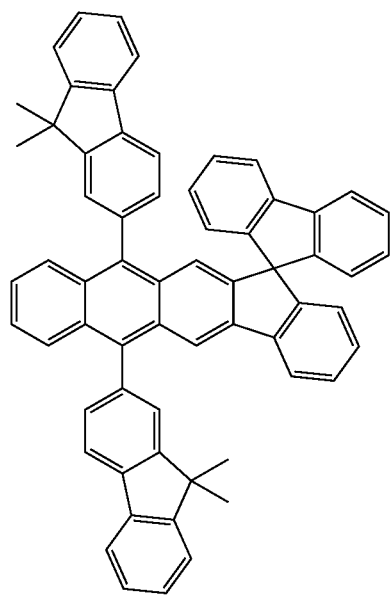
Inv-3-17
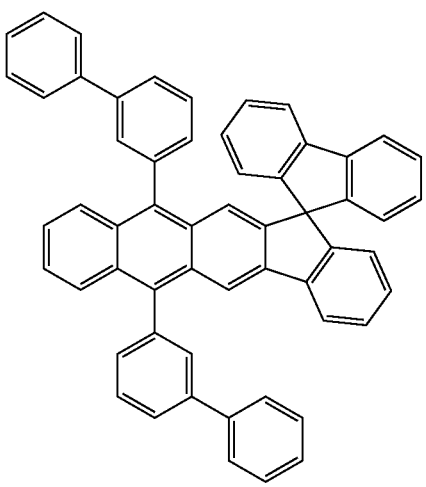
Inv-3-18

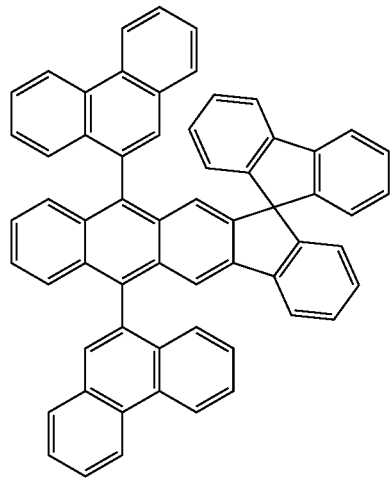
Inv-3-19
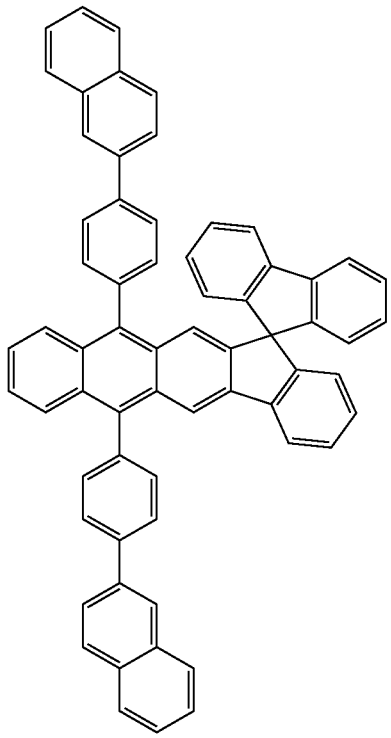
Inv-3-20
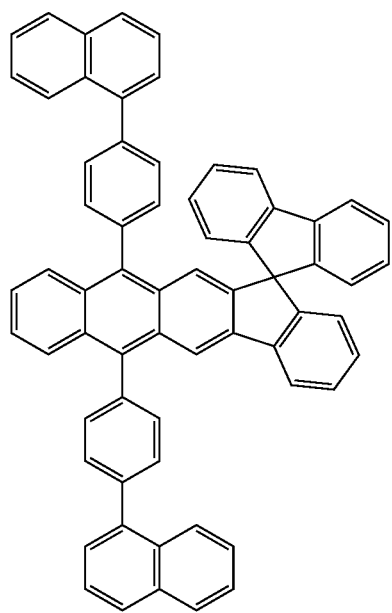
Inv-3-21
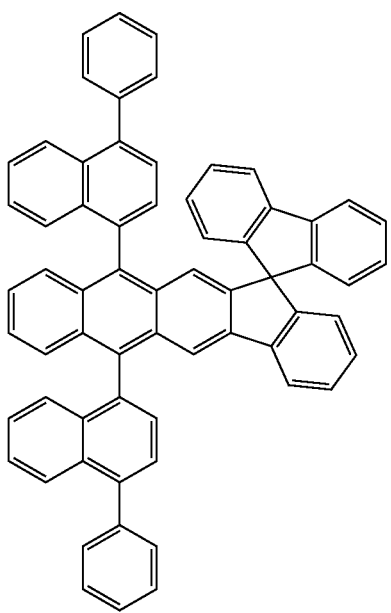
Inv-3-22

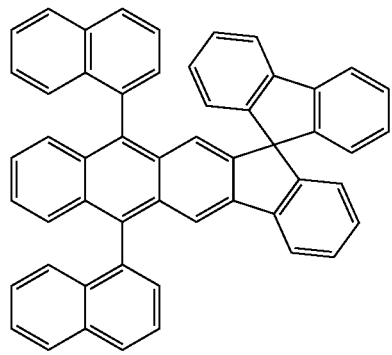
Inv-3-23
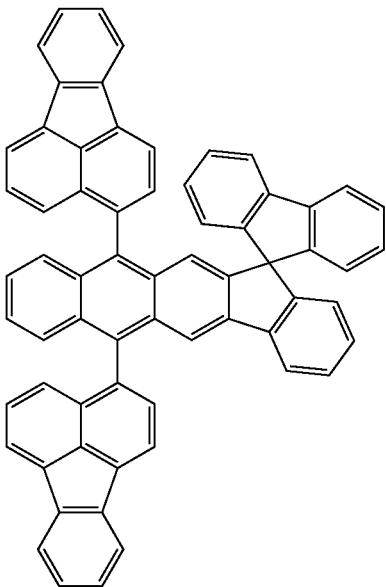
Inv-3-24
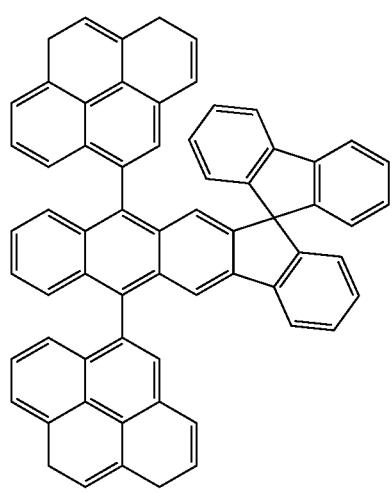
Inv-3-25
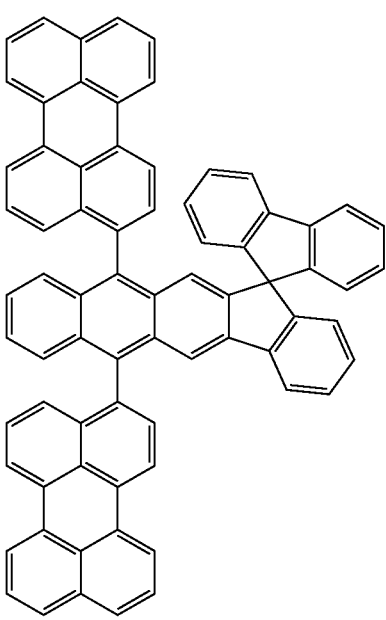
Inv-3-26

Inv-3-27
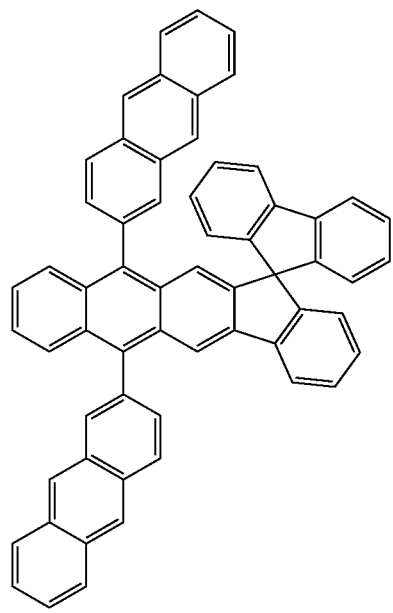
Inv-3-28
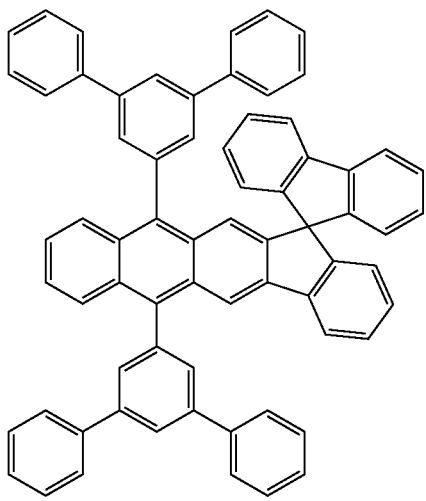
Inv-3-29
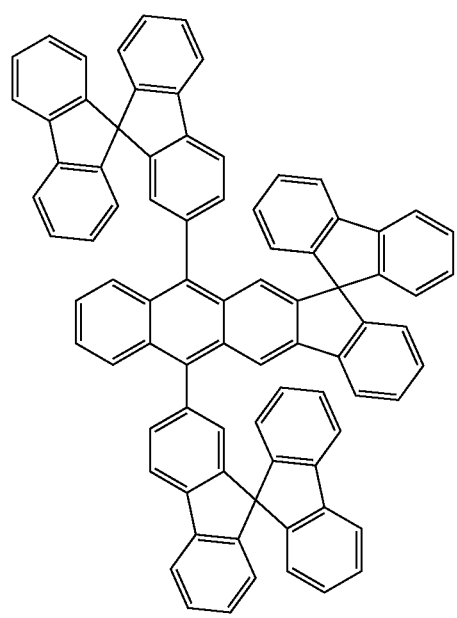
Inv-4-1
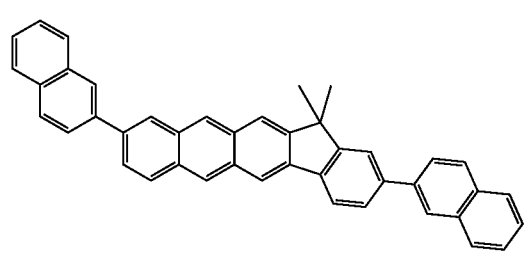
Inv-4-2
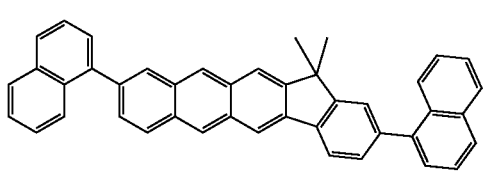

-continued
Inv-4-3
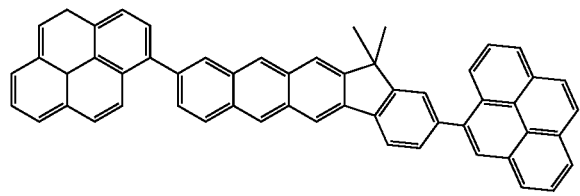
Inv-4-4
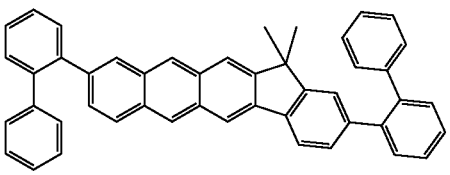
Inv-4-5
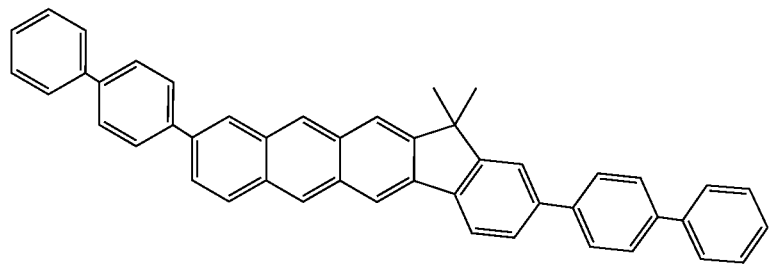
Inv-4-6
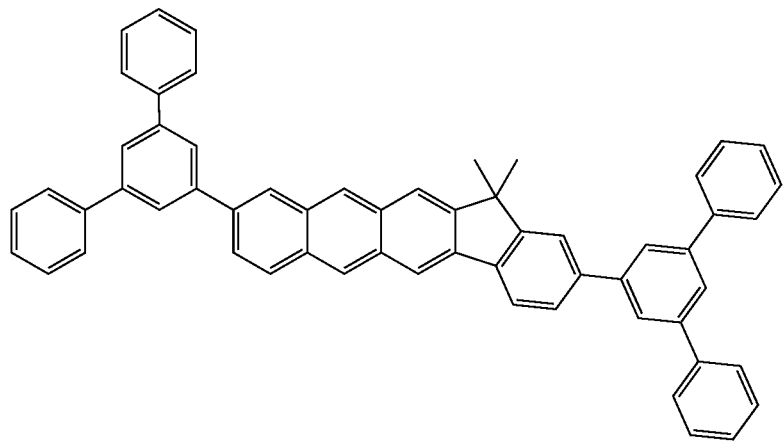
Inv-4-7
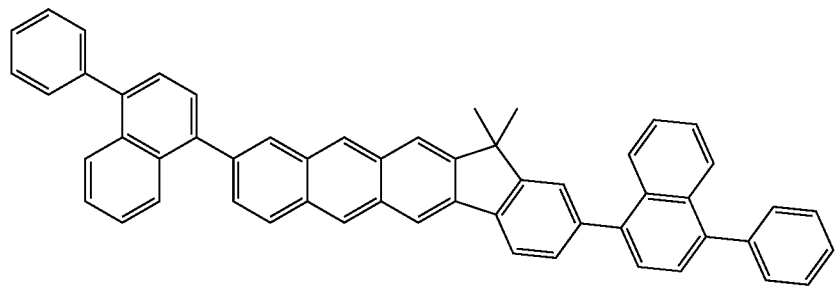
Inv-4-8
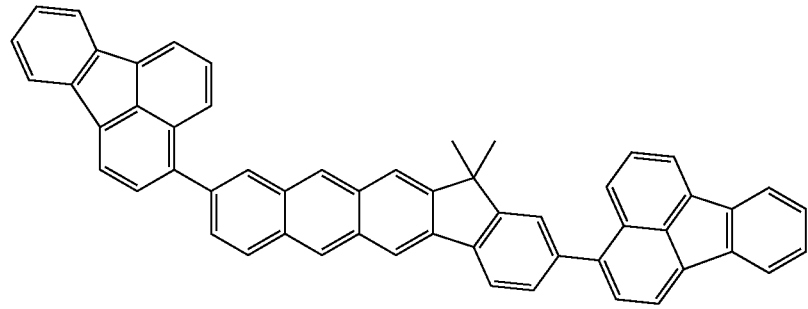

-continued
Inv-4-9
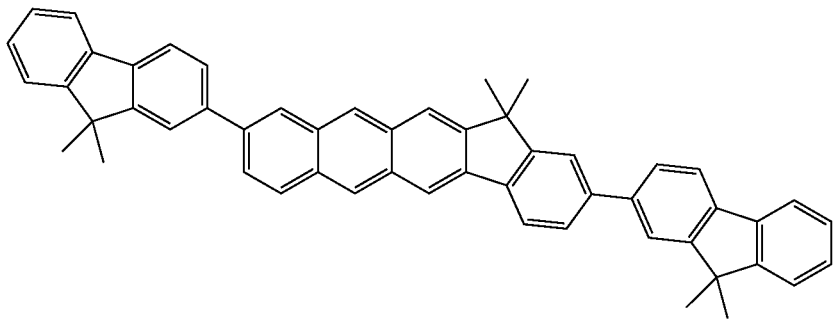
Inv-4-10
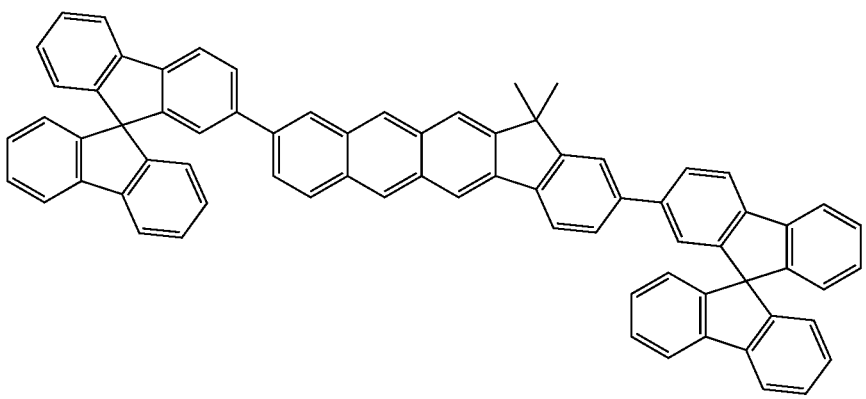
Inv-4-11
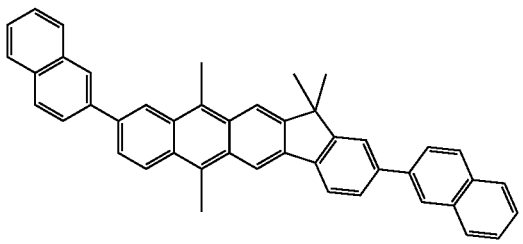
Inv-4-12
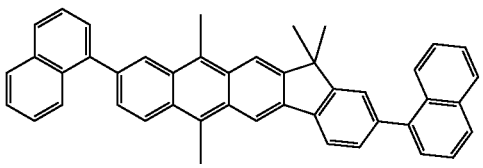
Inv-4-13
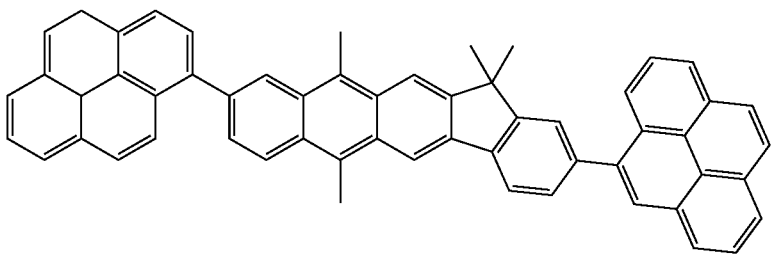
Inv-4-14
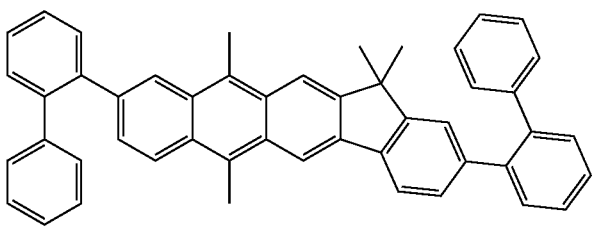

Inv-4-15
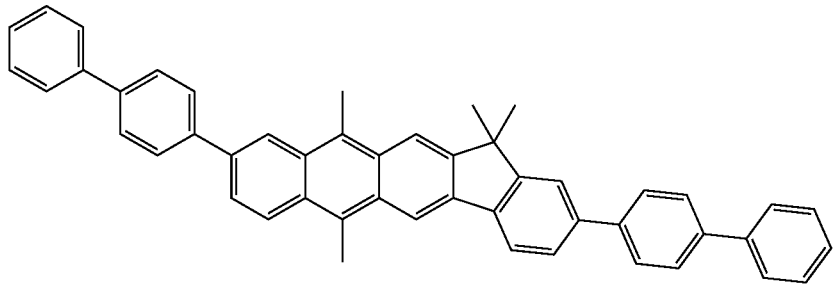
Inv-4-16
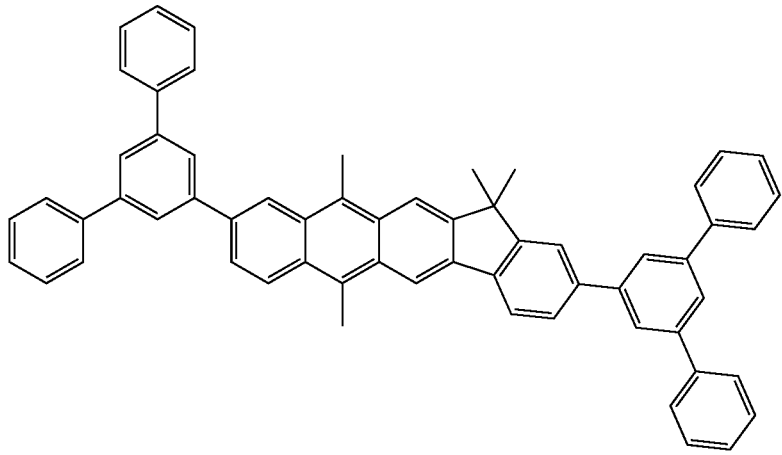
Inv-4-17
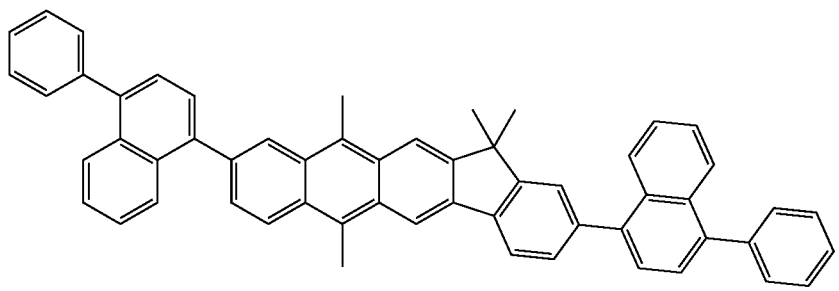
Inv-4-18
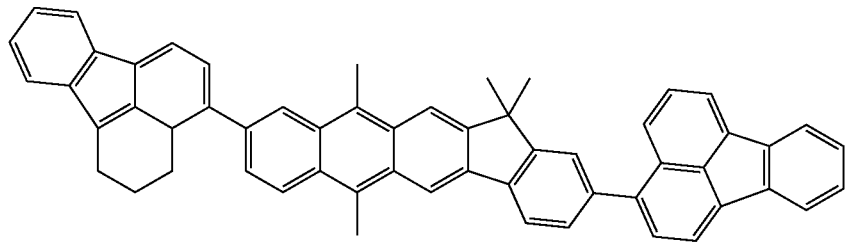
Inv-4-19
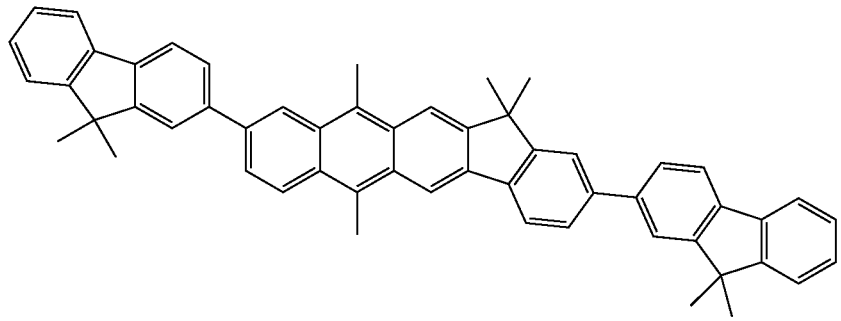

Inv-4-20
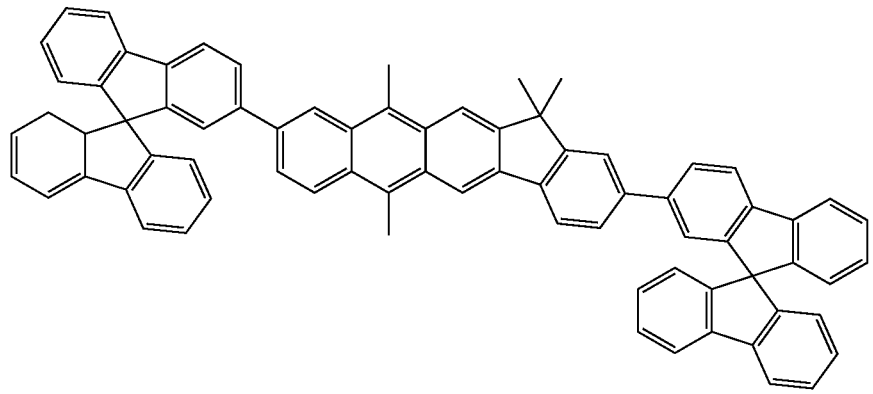
Inv-4-21
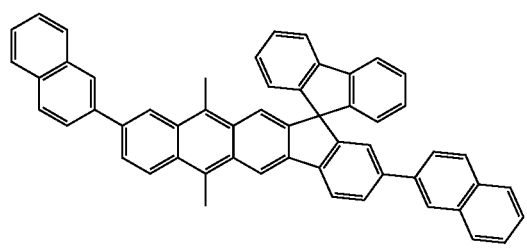
Inv-4-22
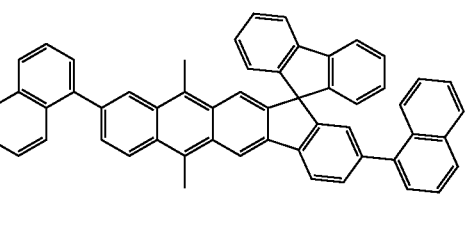
Inv-4-23
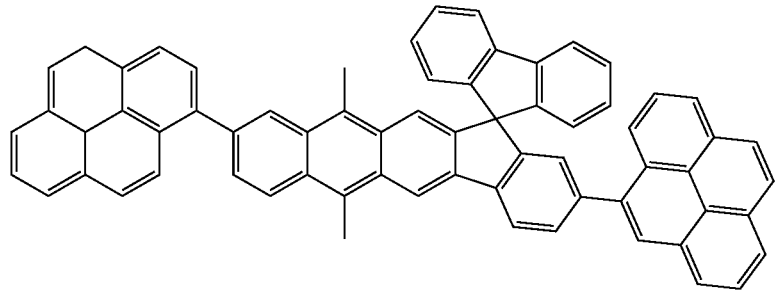
Inv-4-24
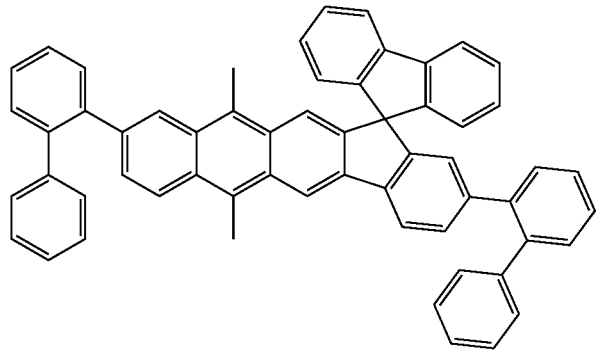
Inv-4-25
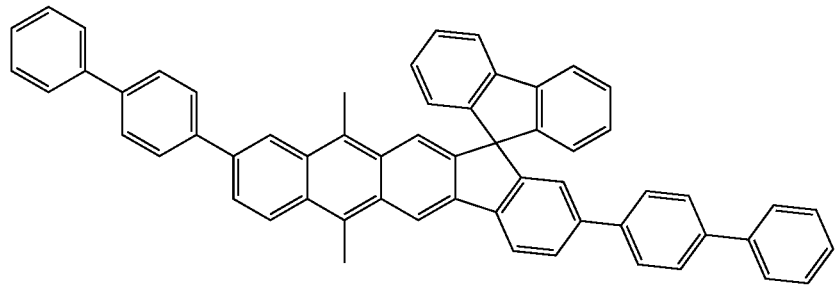

Inv-4-26
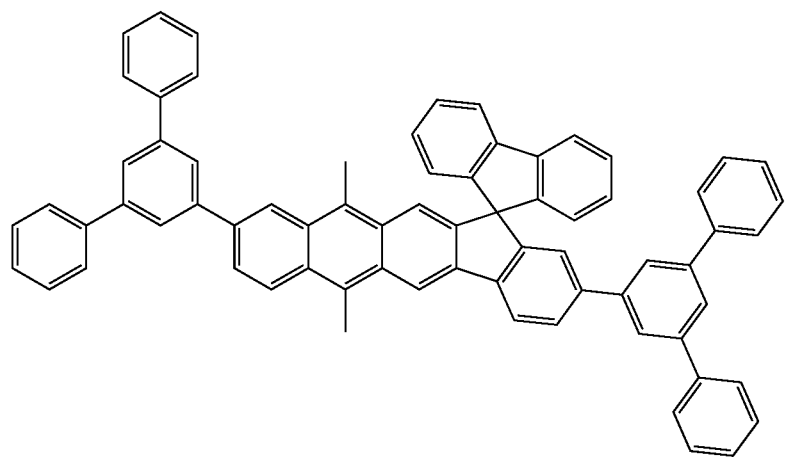
Inv-4-27
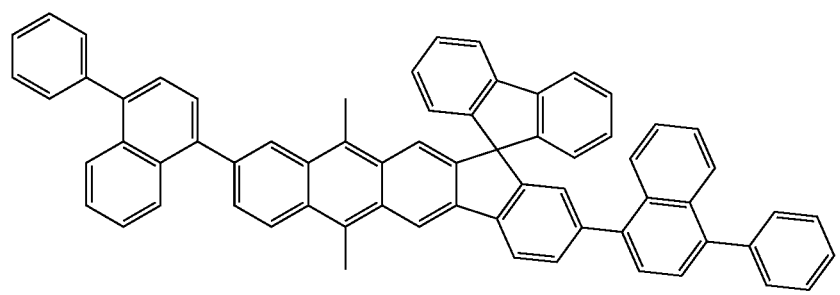
Inv-4-28
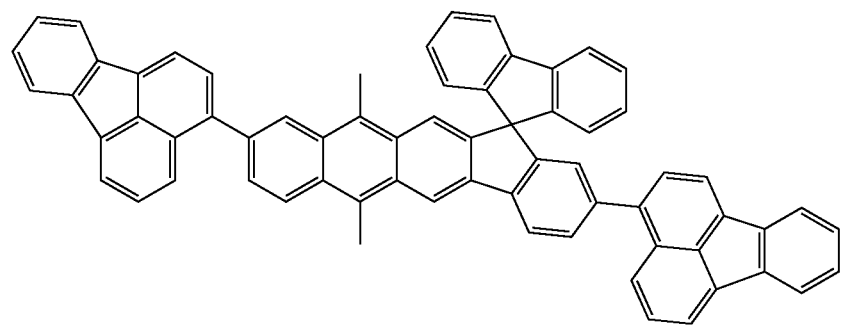
Inv-4-29
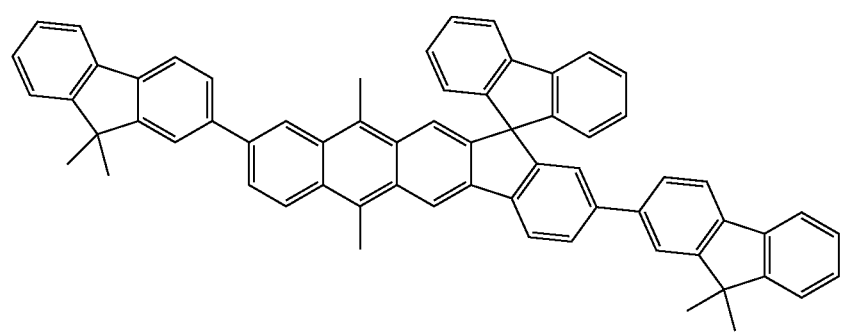

Inv-4-30
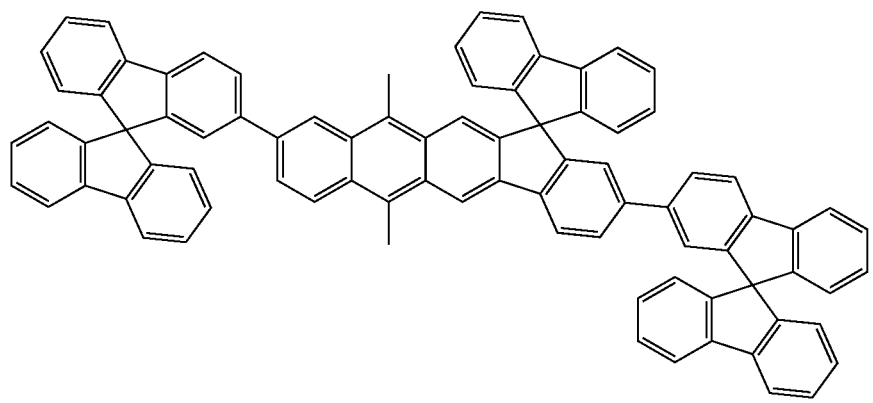
Inv 5-1 Inv 5-2
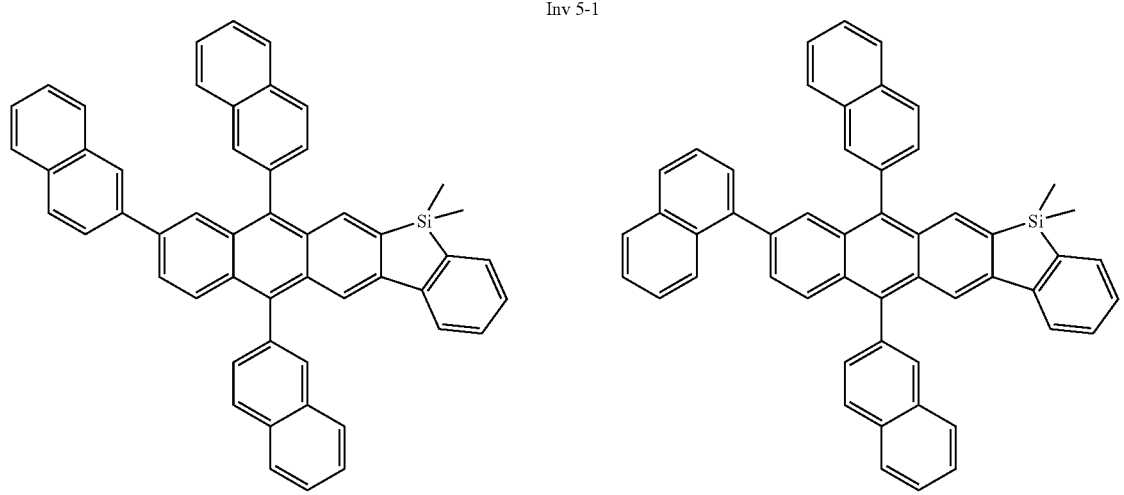
Inv 5-3 Inv 5-4
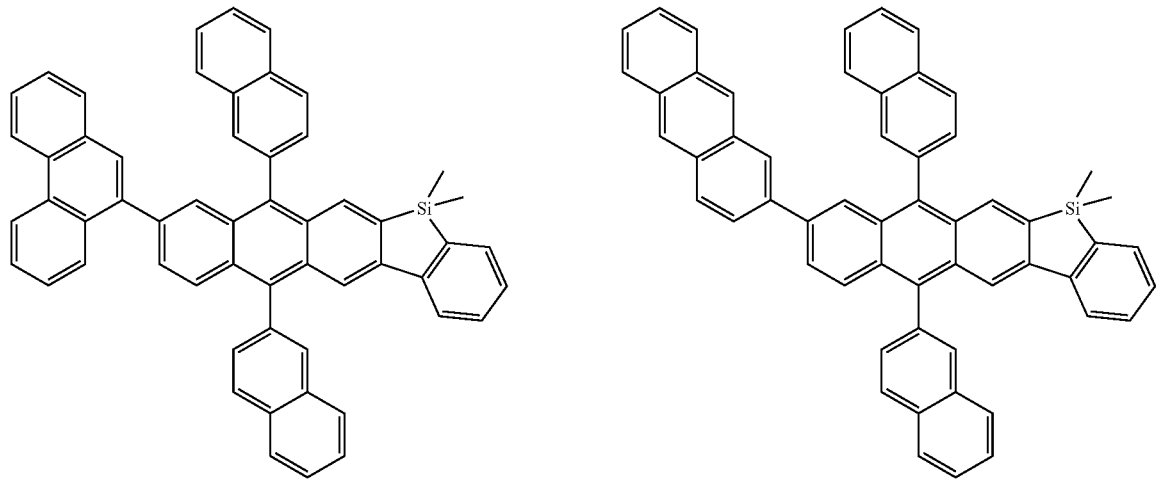

-continued
Inv 5-5
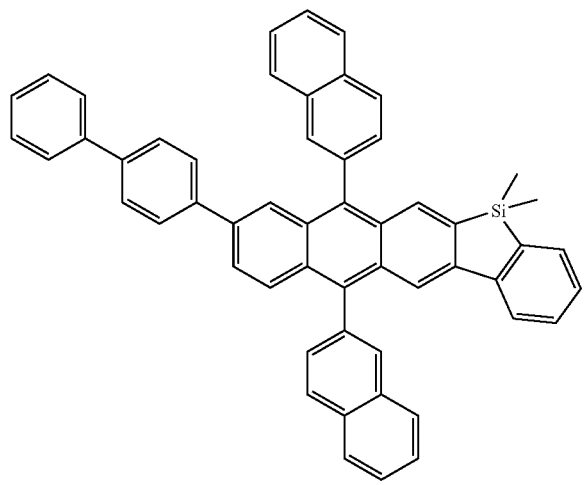
Inv 5-6
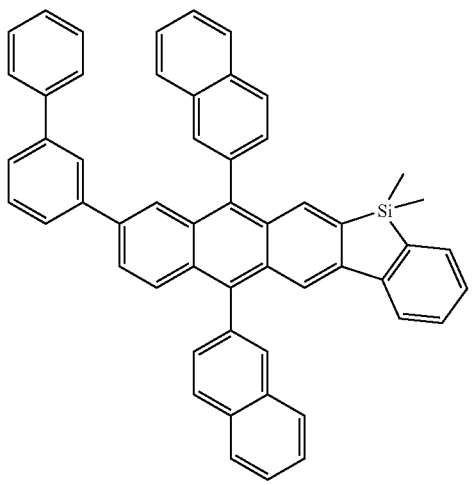
Inv 5-7
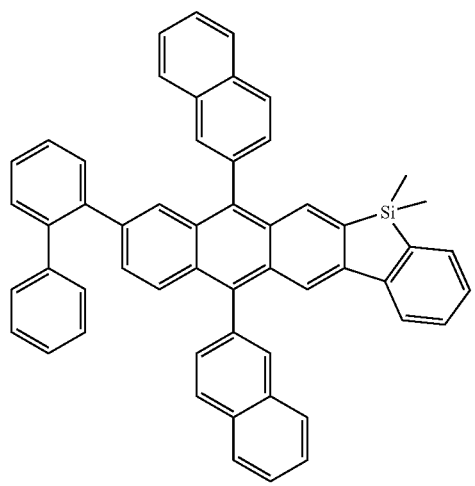
Inv 5-8
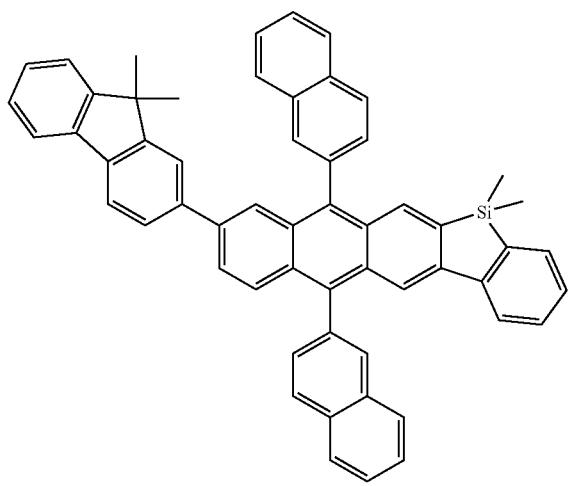
Inv 5-9
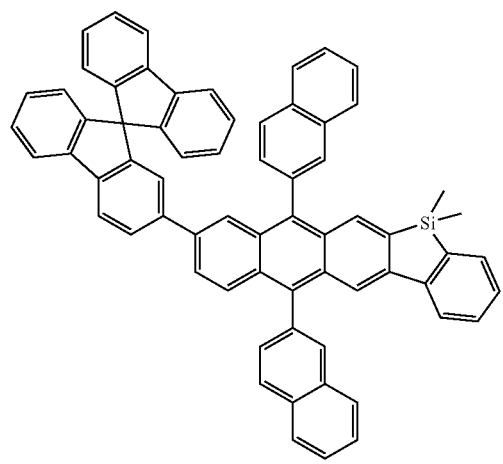
Inv 5-10
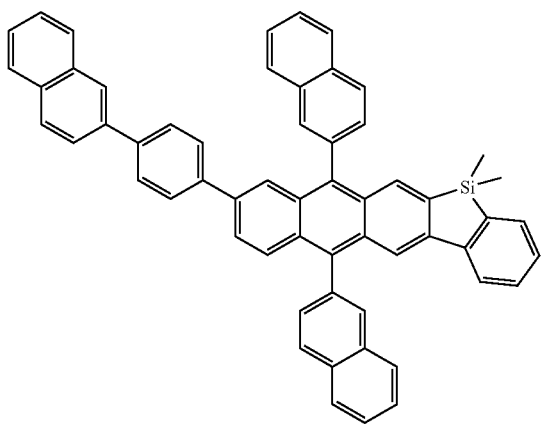

-continued
Inv 5-11
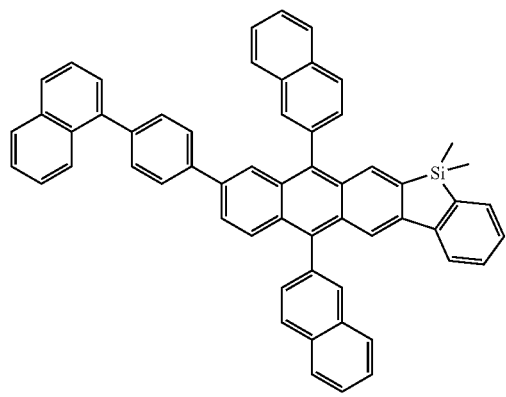
Inv 5-12
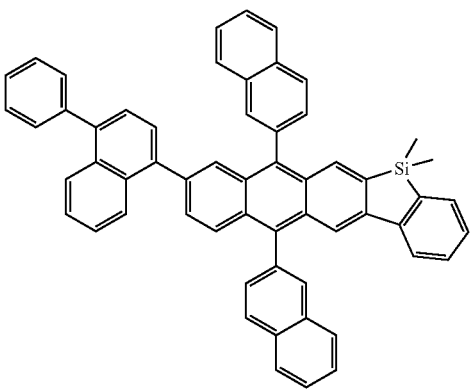
Inv 5-13
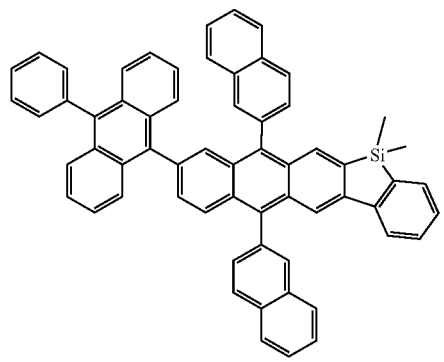
Inv 5-14
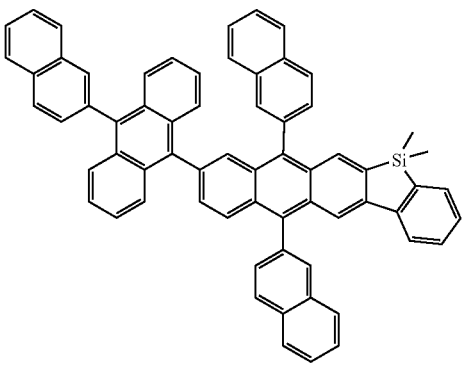
Inv 5-15
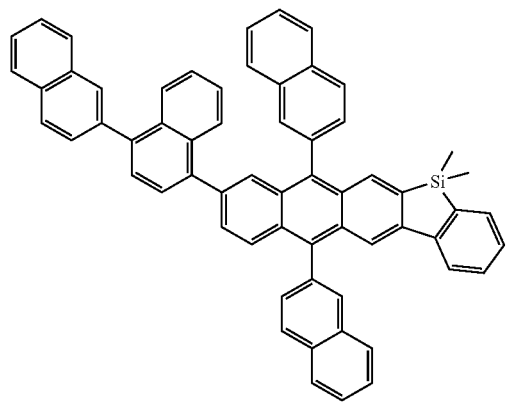
Inv 5-16
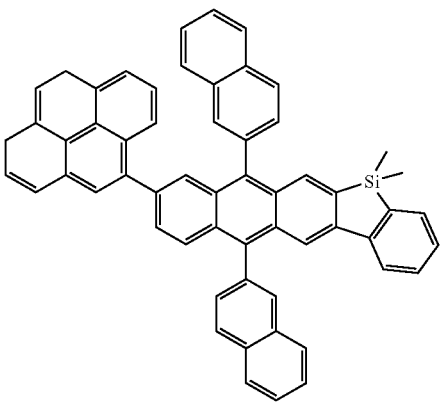
Inv 5-17
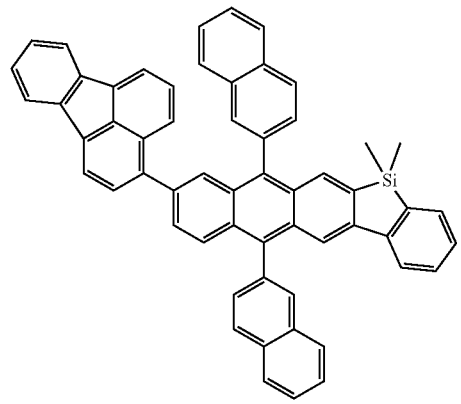
Inv 5-18
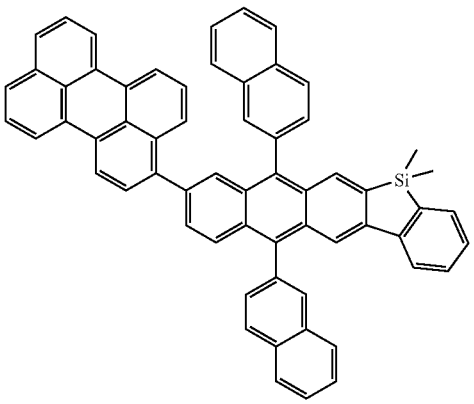

-continued
Inv 5-19
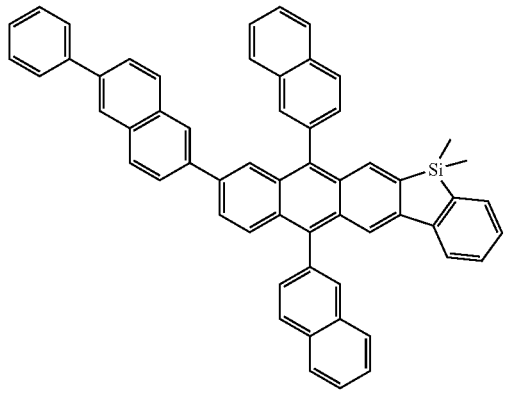
Inv 5-20
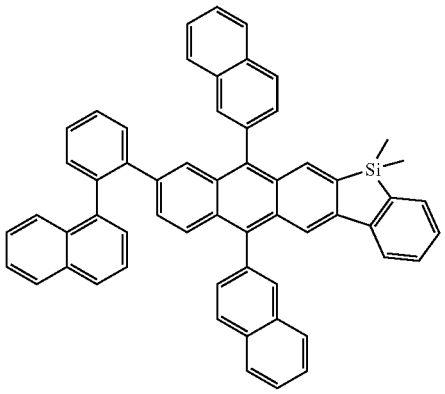
Inv 5-21
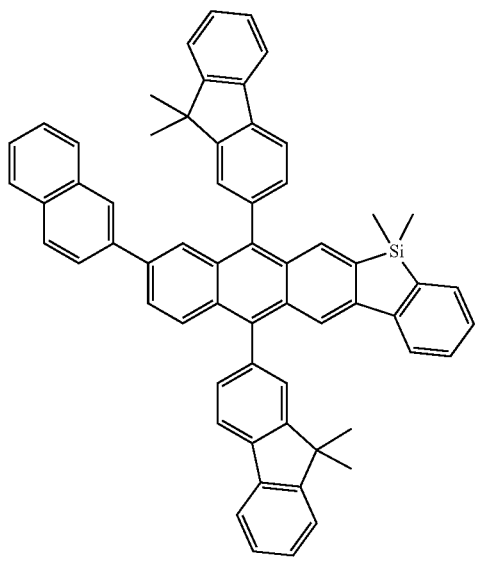
Inv 5-22
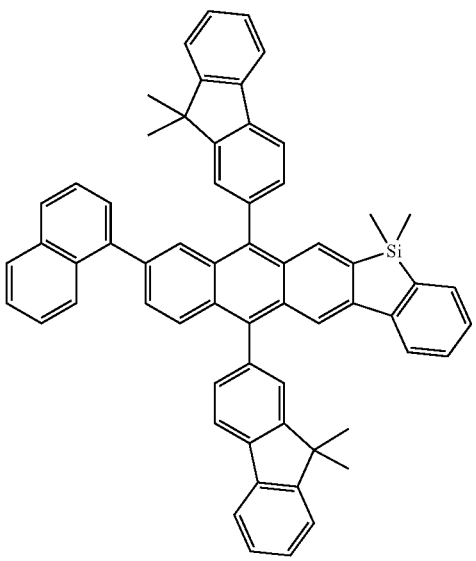
Inv 5-23
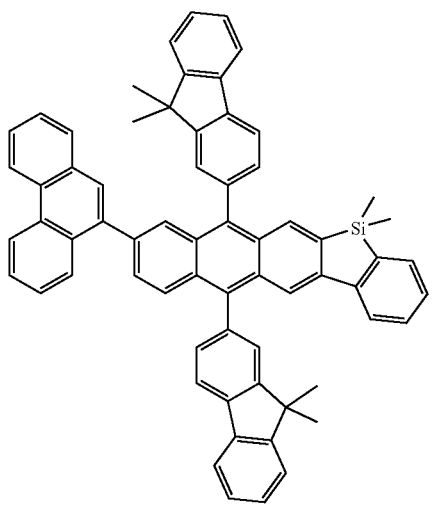
Inv 5-24
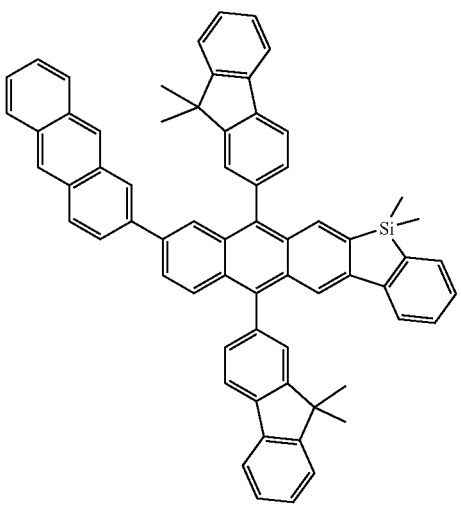

-continued
Inv 5-25
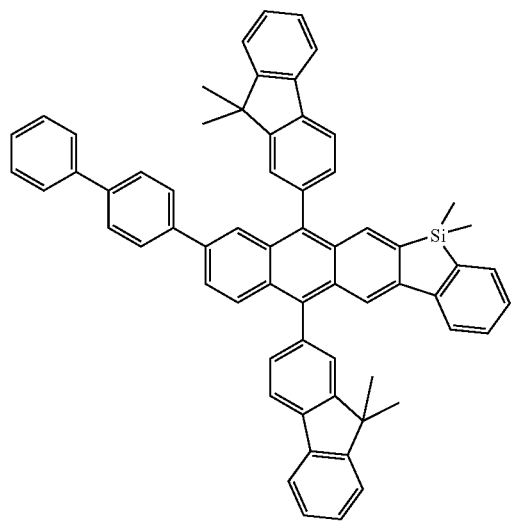
Inv 5-26
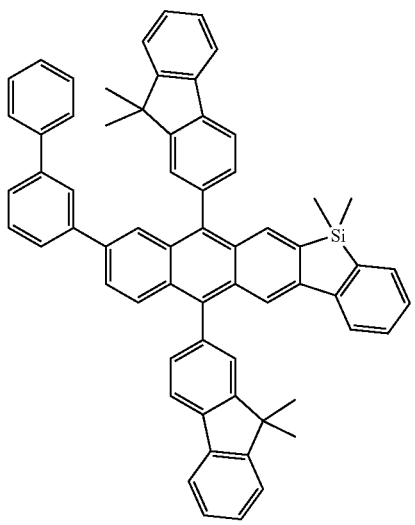
Inv 5-27
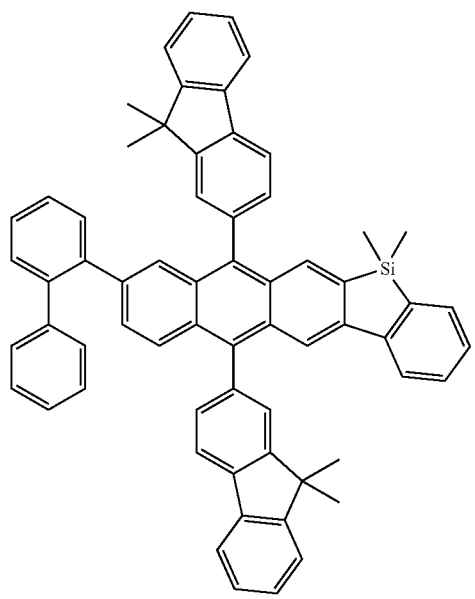
Inv 5-28
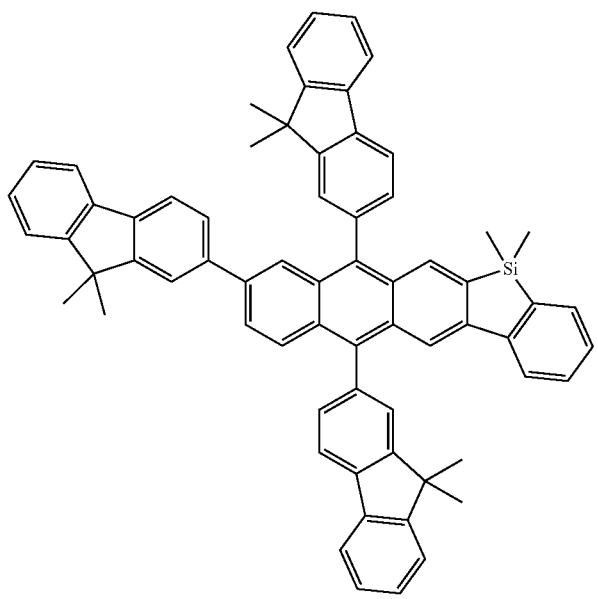
Inv 5-29
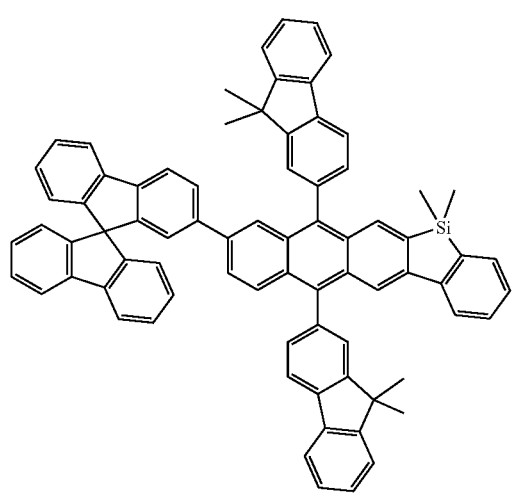
Inv 5-30
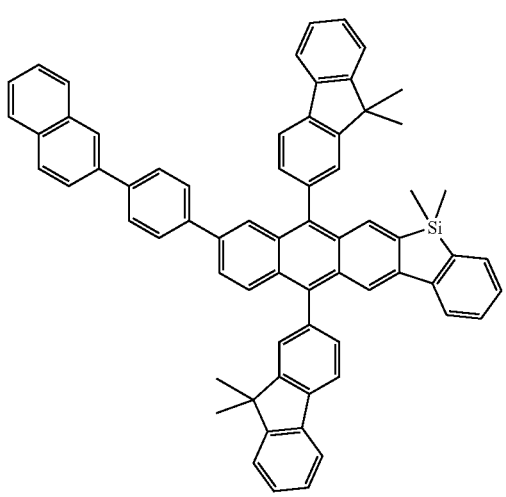

Inv 5-31
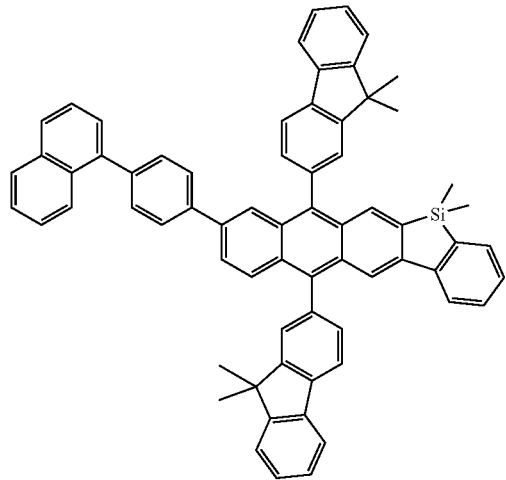
Inv 5-32
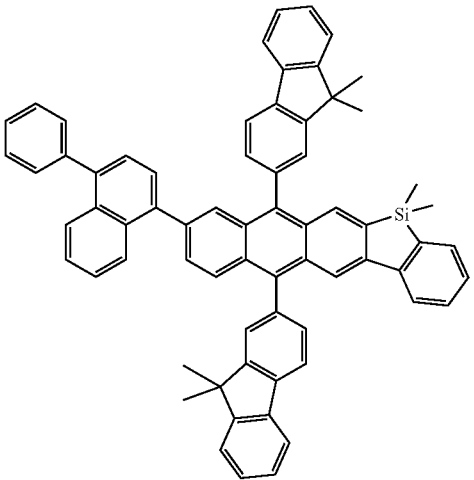
Inv 5-33
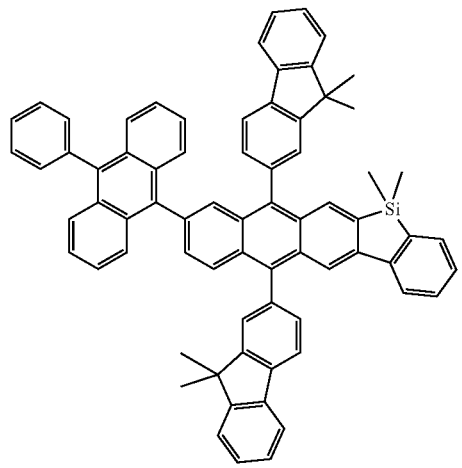
Inv 5-34
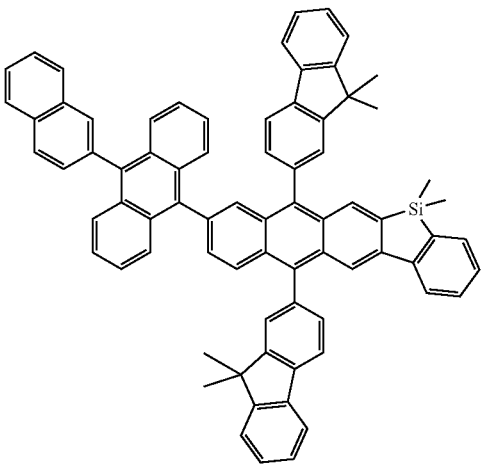
Inv 5-35
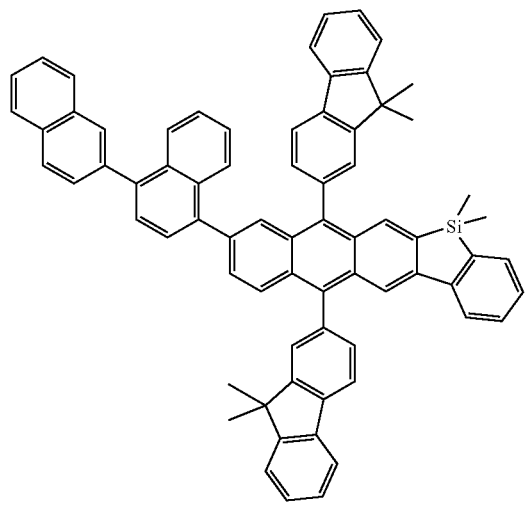
Inv 5-36
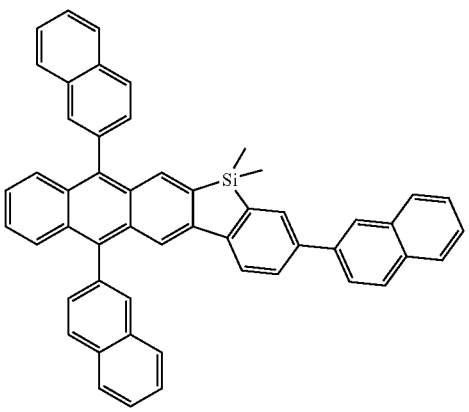

Inv 5-37

Inv 5-38

Inv 5-39

Inv 5-40

Inv 5-41

Inv 5-42

-continued
Inv 5-43
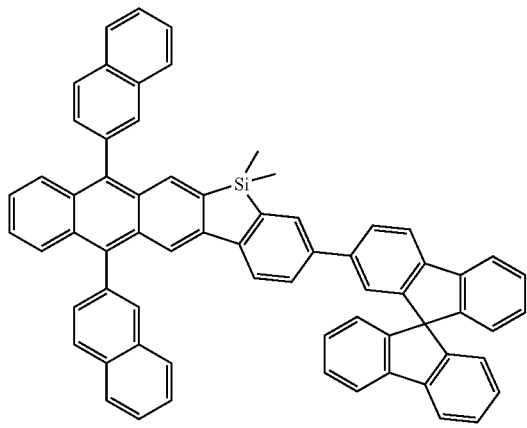
Inv 5-44
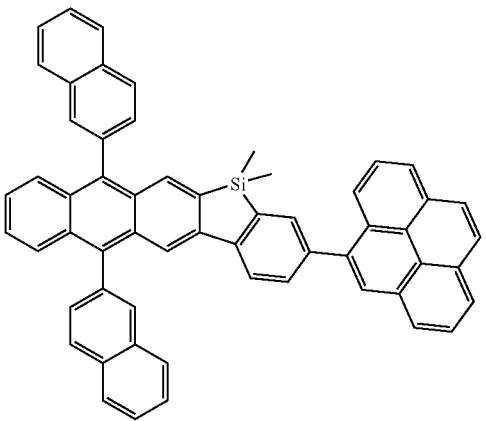
Inv 5-45
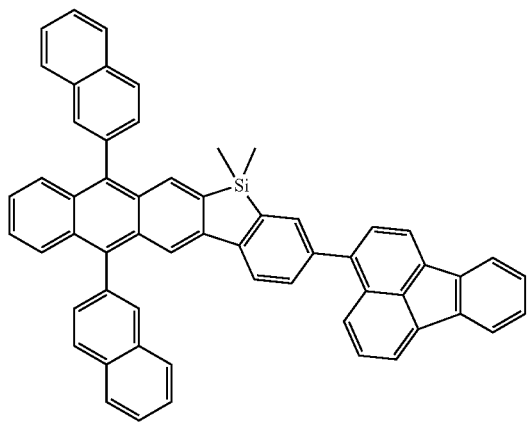
Inv 5-46
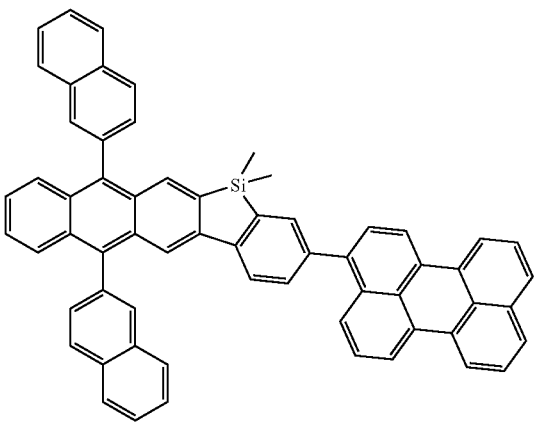
Inv 5-47
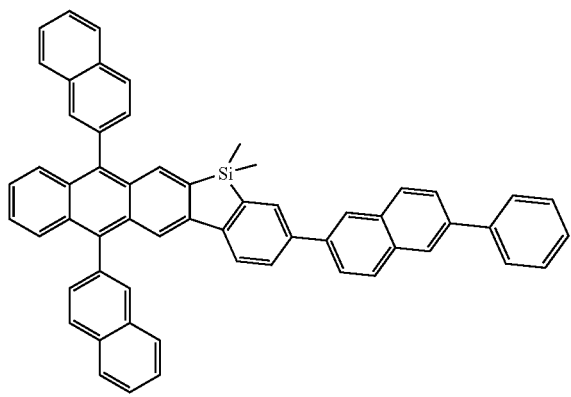
Inv 6-1
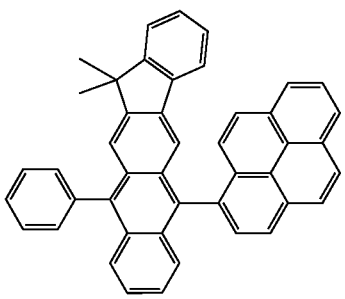

-continued
Inv 6-2
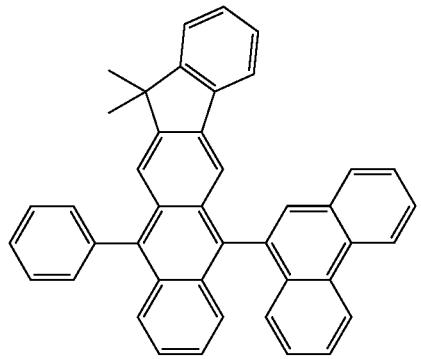
Inv 6-3
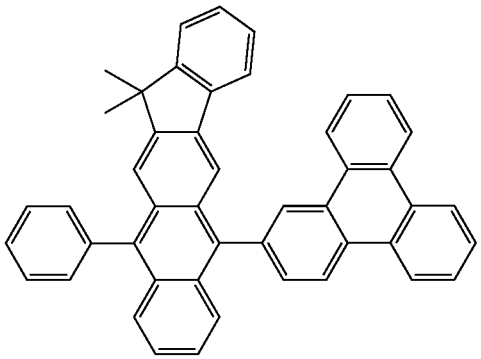
Inv 6-4
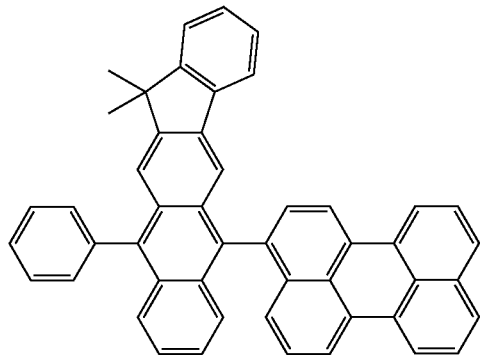
Inv 6-5
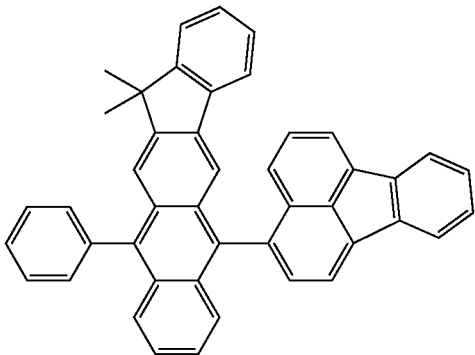
Inv 6-6
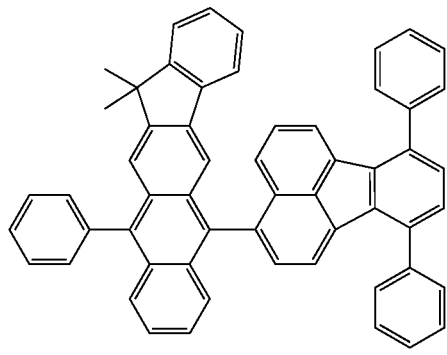
Inv6-7
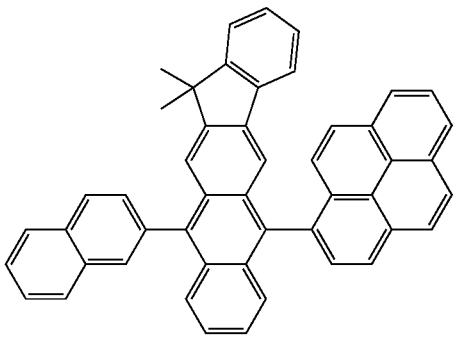
Inv6-8
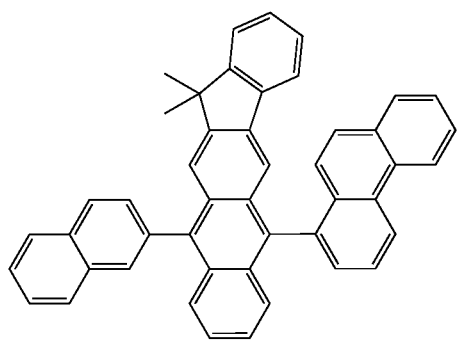
Inv6-9
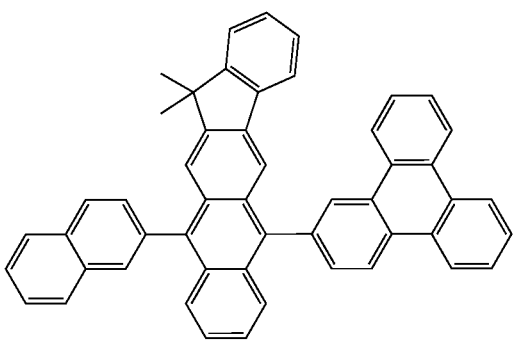

-continued
Inv6-10
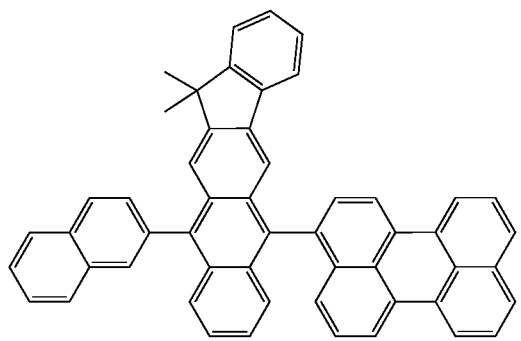
Inv6-11
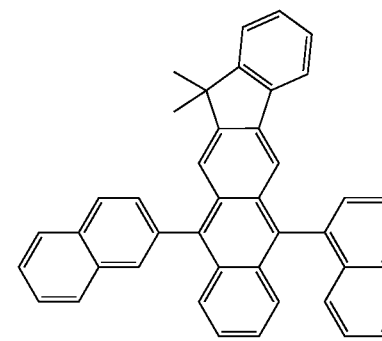
Inv6-12
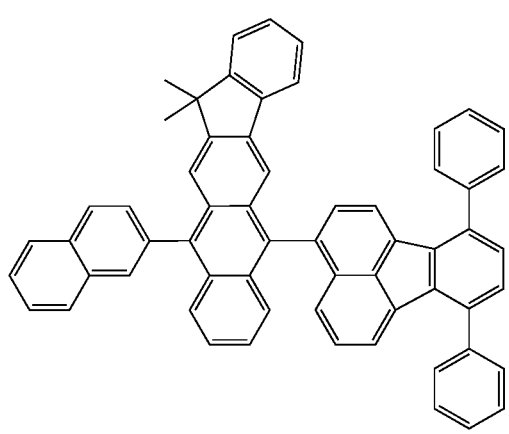
Inv6-13
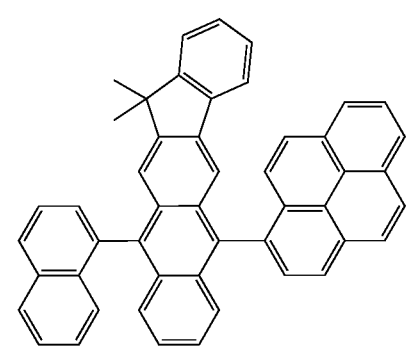
Inv6-14
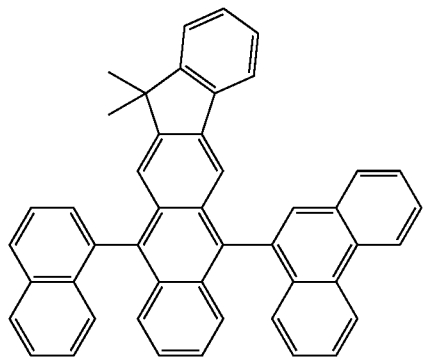
Inv6-15
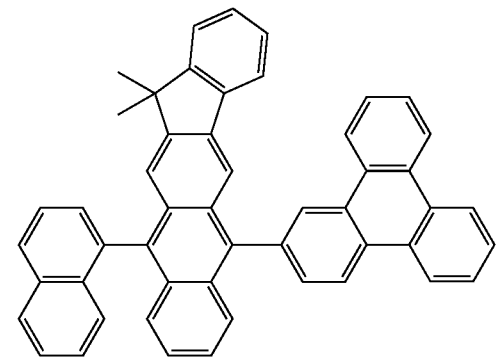
Inv6-16
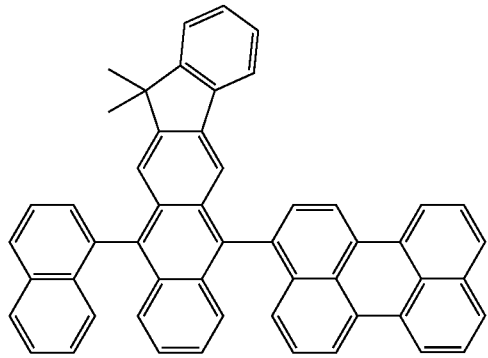
Inv6-17
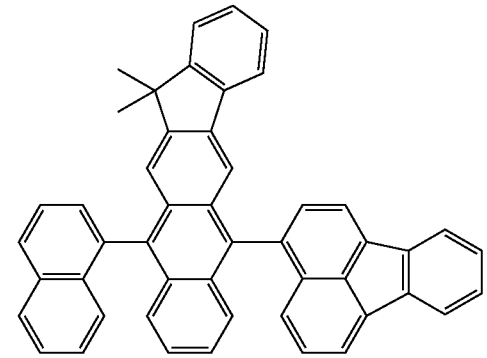

Inv6-18

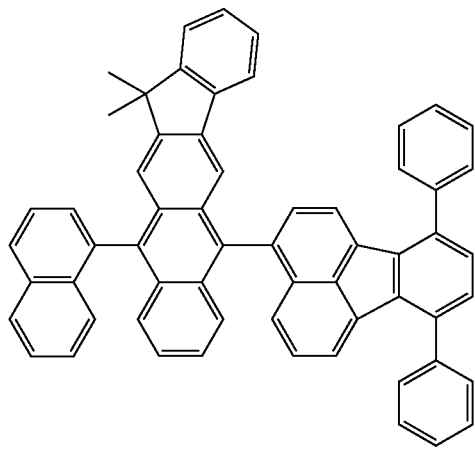

The present invention also provides an organic light-emitting layer including the above-described compound of Formula 1 and an organic light-emitting device including the above-described compound of Formula 1.

In detail, the inventive organic light-emitting device includes (i) an anode, (ii) a cathode, and (iii) one or more organic material layers interposed between the anode and the cathode, wherein at least one of the organic material layers is an organic material layer including the above-described compound of Formula 1.

The organic material layer including the compound of Formula 1 may be at least one of a hole injection layer, a hole transport layer, a light-emitting layer, an electron transport layer and an electron injection layer. Preferably, the compound of Formula 1 may be included as a light-emitting material in an organic light-emitting device. In this case, the organic light-emitting device can exhibit better emission efficiency, brightness, power efficiency, thermal stability and device lifetime. More preferably, the compound of Formula 1 may be included as a green or blue light-emitting material in an organic light-emitting device. Thus, it is preferred that the organic material layer including the compound of Formula 1 is a light-emitting layer.

In the inventive organic light-emitting device, other organic material layer(s) excluding the organic material layer including the compound of Formula 1 may be a hole injection layer, a hole transport layer, a light-emitting layer and/or an electron transport layer.

As a non-limiting example, the inventive organic light-emitting device may be structured such that a substrate, an anode, a hole injection layer, a hole transport layer, a light-emitting layer, an electron transport layer and a cathode are sequentially stacked one onto another. Here, the light-emitting layer includes the compound of Formula 1. An electron injection layer may also be disposed on the electron transport layer.

The inventive organic light-emitting device may also be structured such that an anode, one or more organic material layers and a cathode are sequentially stacked, as described above, and an insulating layer or an adhesive layer is interposed between an electrode and an organic material layer.

In the inventive organic light-emitting device, the organic material layer including the compound of Formula 1 may be formed by vacuum deposition or solution coating. Examples of the solution coating include spin coating, dip coating, doctor blading, inkjet printing, thermal transfer, etc., but are not limited thereto.

In the inventive organic light-emitting device, organic material layers and electrodes may be formed of materials known in the art using a method known in the art except that at least one layer of the organic material layers includes the compound of Formula 1.

For example, a substrate may be a silicon wafer, quartz, a glass plate, a metal plate, a plastic film or sheet, etc.

An anode material may be a metal such as vanadium, chromium, copper, zinc, or gold, or an alloy thereof; metal oxide such as zinc oxide, indium oxide, indium tin oxide (ITO), indium zinc oxide; a metal-oxide complex such as ZnO:Al or SnO$_2$:Sb; a conductive polymer such as polythiophene, poly(3-methylthiophene), poly[3,4-(ethylene-1, 2-dioxy)thiophene] (PEDT), polypyrrole and polyaniline; carbon black, etc., but is not limited thereto.

A cathode material may be a metal such as magnesium, calcium, sodium, potassium, titanium, indium, yttrium, lithium, gadolinium, aluminum, silver, tin or lead, or an alloy thereof; a multi-layered material such as LiF/Al or LiO$_2$/Al, but is not limited thereto.

Materials for a hole injection layer, a hole transport layer and an electron transport layer are not particularly limited, and may be materials commonly known in the art.

Hereinafter, the present invention will be described more specifically with reference to the following examples. The following examples are only for illustrative purposes and are not intended to limit the scope of the invention.

<Reaction Scheme 1>

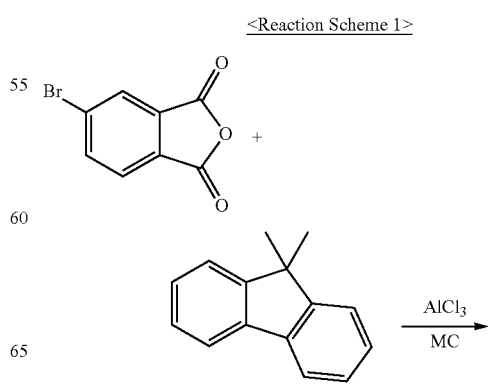

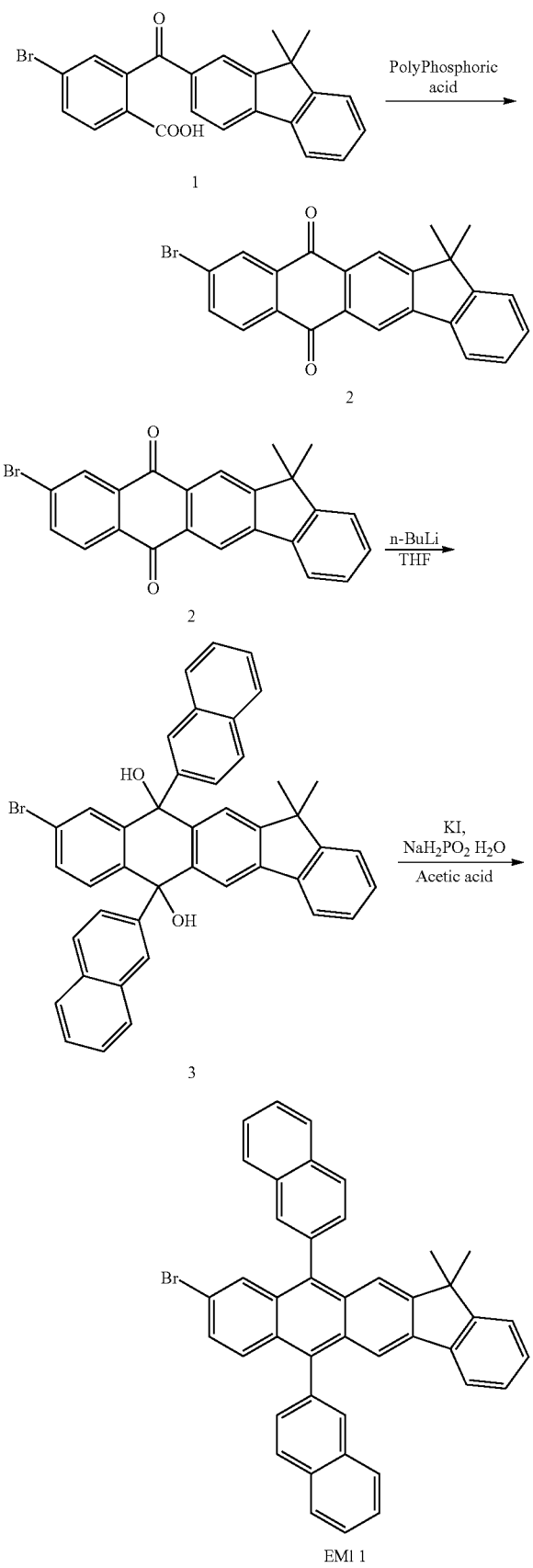

Synthesis Example 1-1

Preparation of bromo-2-(7-bromo-9,9-dimethyl-9H-fluorene-2-carbonyl)-benzoic acid of Reaction Scheme 1

Bromo-9,9-dimethyl-9H-fluorene (40 g, 1 eq, 0.146 mol) and 2-bromophthalic anhydride (36.5 g, 1.1 eq, 0.161 mol) were placed in a reaction vessel and dichloromethane (1.5 l) was added thereto. Then, aluminum chloride (29.2 g, 1.5 eq, 0.219 mol) was gradually added at 0° C., and the reaction mixture was stirred at room temperature for 12 hours. After the reaction was terminated, distilled water was gradually added at 0° C., and the reaction solution was extracted with an excess of dichloromethane and several times washed with distilled water. After solvent removal, the resultant solid was placed in a hexane(2 l)-containing vessel, washed, filtered and dried to give bromo-2-(7-bromo-9,9-dimethyl-9H-fluorene-2-carbonyl)-benzoic acid (59.8 g, yield 82%).

$^1$H-NMR: 8.44 (t, 2H), 8.23 (d, 1H), 7.96 (m, 5H), 7.72 (m, 5H), 7.55 (t, 1H), 1.67 (s, 6H).

Synthesis Example 1-2

Preparation of 9-bromo-13,13-dimethyl-6H-indeno[1,2-b]anthracene-6,11(13H)-dione of Reaction Scheme 1

Bromo-2-(7-bromo-9,9-dimethyl-9H-fluorene-2-carbonyl)-benzoic acid (20 g, 1 eq, 0.0399 mol) was placed in a flask, and polyphosphoric acid (50 ml) was added thereto. The reaction mixture was stirred at 140° C. for two hours while heating and cooled to less than 50° C., and distilled water was gradually added thereto. The resultant solid was filtered, washed with a small amount of methanol, and dried to give 9-bromo-13,13-dimethyl-6H-indeno[1,2-b]anthracene-6,11(13H)-dione (15 g, yield=78%).

$^1$H-NMR: 8.29 (t, 3H), 8.09 (s, 2H), 7.85 (d, 2H), 7.72 (m, 2H), 1.67 (s, 6H).

Synthesis Example 1-3

Preparation of 9-bromo-13,13-dimethyl-6,11-di(naphthalen-2-yl)-11,13-dihydro-6H-indeno[1,2-b]anthracene-6,11-diol of Reaction Scheme 1

2-Bromonaphthrene (4.96 g, 2.2 eq, 0.054 mol) was placed in a flask, and THF (200 ml) was dissolved therein. Then, n-BuLi (38.4 ml, 2.5 eq, 0.06 mol) was gradually added at −78° C., and the reaction mixture was stirred for one hour. 9-Dibromo-13,13-dimethyl-6H-indeno[1,2-b]anthracene-6,11(13H)-dione (11.8 g, 1 eq, 0.024 mol) was then added thereto and the reaction mixture was stirred at room temperature for 17 hours. After the reaction was terminated, the reaction solution was washed with distilled water, extracted with ethyl acetate, and purified by column chromatography to give 9-dibromo-13,13-dimethyl-6,11-di(naphthalen-2-yl)-11,13-dihydro-6H-indeno[1,2-b]anthracene-6,11-diol (13.8 g, yield=78%).

$^1$H-NMR: 8.02 (d, 3H), 7.95 (d, 2H), 7.61 (s, 2H), 7.64 (m, 9H), 7.46 (s, 2H), 7.19 (d, 2H), 1.67 (s, 6H).

Synthesis Example 1-4

Preparation of 9-bromo-13,13-dimethyl-6,11-di(naphthalen-2-yl)-13H-indeno[1,2-b]anthracene (EMl-1) of Reaction Scheme 1

9-Dibromo-13,13-dimethyl-6,11-di(naphthalen-2-yl)-11,13-dihydro-6H-indeno[1,2-b]anthracene-6,11-diol (10 g, 1 eq, 0.013 mol) and potassium iodide (21.58 g, 10 eq, 0.13 mol), and sodium hypophosphite (19.61 g, 16.5 eq, 0.223 mol) were placed in a flask, and acetic acid (500 ml) was added thereto. The reaction mixture was stirred for five hours while heating. After the reaction was terminated, the reaction solution was added to an excess of distilled water, and the resultant solid was washed, filtered and purified by column chromatography to give 9-dibromo-13,13-dimethyl-6,11-di(naphthalen-2-yl)-13H-indeno[1,2-b]anthracene (EMI 1) (6.9 g, yield=76%).

$^1$H-NMR: 8.11 (d, 3H), 8.02 (d, 2H), 7.95 (d, 2H), 7.61 (s, 2H), 7.64 (m, 4H), 7.46 (s, 2H), 7.19 (d, 2H), 1.67 (s, 6H).

Synthesis Example 1-5

Preparation of EMI 2 of Reaction Scheme 2

EMI 2 was synthesized in the same manner as in Synthesis Example 1-3 using 2-bromo-9,9-dimethyl-9H-fluorene instead of 2-bromonaphthrene.

Elemental Analysis: C, 84.00; H, 5.45; Br, 10.54/HRMS [M]$^+$: 758.

[Reaction Scheme 2]

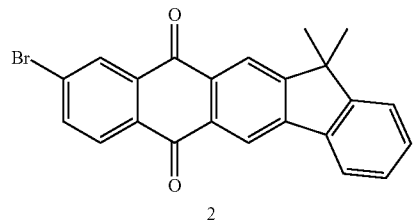

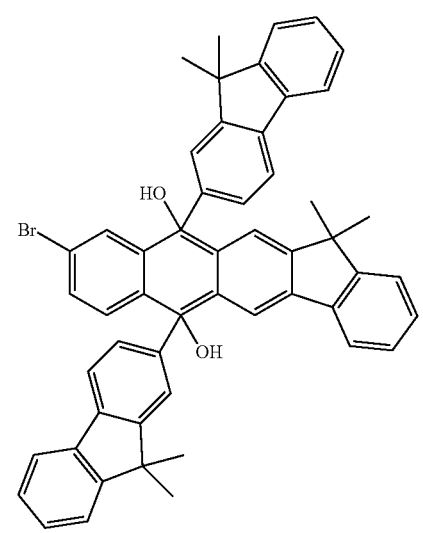

[Reaction Scheme 3]

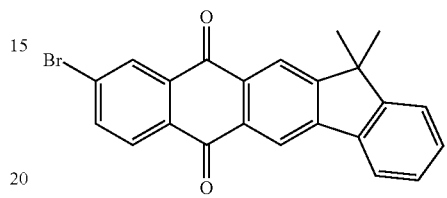

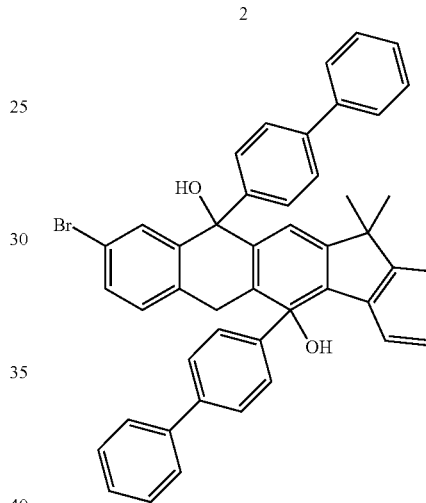

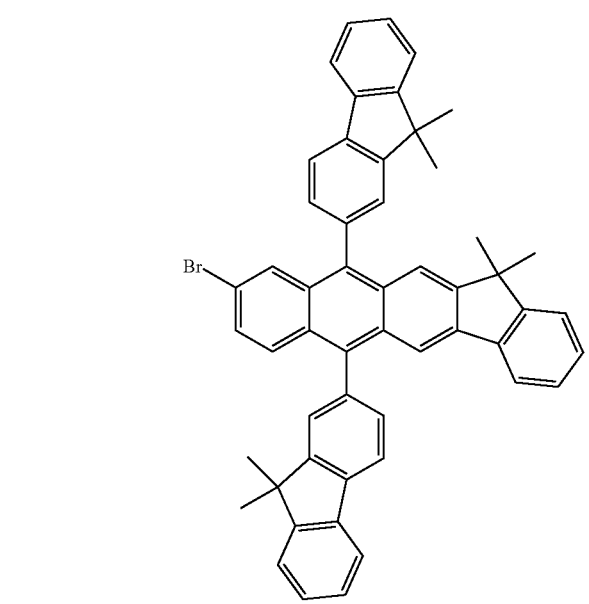

EMI 2

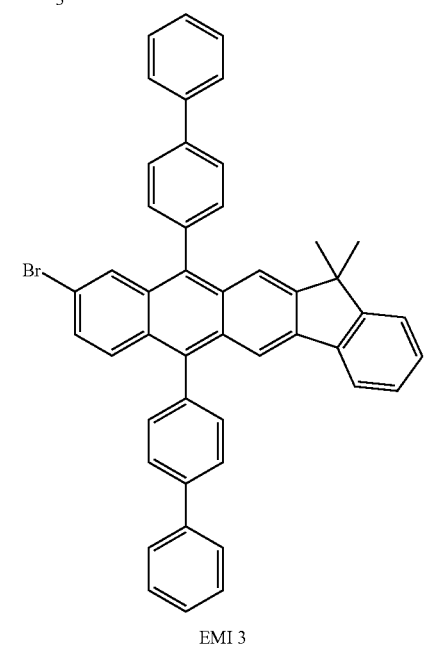

EMI 3

Synthesis Example 1-6

Preparation of EMI3 of Reaction Scheme 3

EMI 3 was synthesized in the same manner as in Synthesis Example 1-3 using 4-bromobiphenyl instead of 2-bromonaphthrene.
Elemental Analysis: C, 83.3; H, 4.91; Br, 11.79/HRMS [M]$^+$: 678.

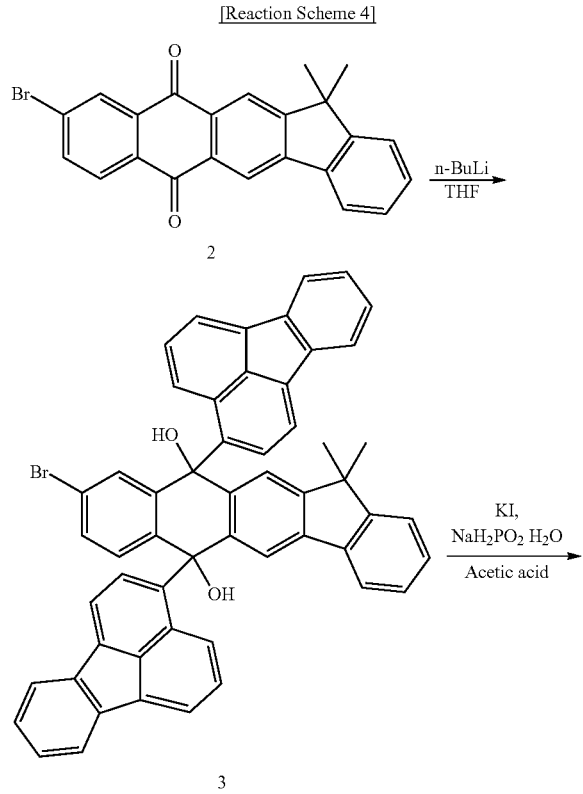

[Reaction Scheme 4]

Synthesis Example 1-7

Preparation of EMI4 of Reaction Scheme 4

EMI4 was synthesized in the same manner as in Synthesis Example 1-3 using 3-bromofluoranthene instead of 2-bromonaphthrene.
Elemental Analysis: C, 85.37; H, 4.30; Br, 10.33/HRMS [M]$^+$: 774.

Synthesis Example 1-8

Preparation of Inv 1-1

9-Dibromo-13,13-dimethyl-6,11-di(naphthalen-2-yl)-13H-indeno[1,2-b]anthracene (EMI1) (10 g, 1 eq, 0.016 mol) obtained in Synthesis Example 1-4, naphthalen-2-ylboronic acid (3.2 g, 1.2 eq, 0.019 mol), and Pd(PPh$_3$)$_4$ (0.65 g, 0.03 eq, 5.7 mmol) were placed in a flask, an aqueous saturated 2M K$_2$CO$_3$ solution (15 ml) and toluene (150 ml) were dissolved therein, and the reaction mixture was stirred for 12 hours while heating. After the reaction was terminated, the reaction solution was filtered through celite, extracted with methylene chloride (MC), and purified by column chromatography to give Inv 1-1 (13,13-dimethyl-6,9,11-tri(naphthalen-2-yl)-13H-indeno[1,2-b]anthracene) (9.5 g, yield=88.7%).
Inv 1-1: Elemental Analysis: C, 94.61; H, 5.39/HRMS [M]$^+$: 672.

Synthesis Examples 1-9~1-27

Preparation of Inv 1-2~Inv 1-20

Inv 1-2~Inv 1-20 were obtained as pale yellow solids according to the same procedure as in Synthesis Example 1-8 except for using corresponding starting materials instead of naphthalen-2-ylboronic acid.
Inv 1-2: Elemental Analysis: C, 94.61; H, 5.39/HRMS [M]$^+$: 672.
Inv 1-3: Elemental Analysis: C, 94.70; H, 5.30/HRMS [M]$^+$: 772
Inv 1-4: Elemental Analysis: C, 94.70; H, 5.30/HRMS [M]$^+$: 722
Inv 1-5: Elemental Analysis: C, 94.52; H, 5.48/HRMS [M]$^+$: 698
Inv 1-6: Elemental Analysis: C, 94.52; H, 5.48/HRMS [M]$^+$: 698
Inv 1-7: Elemental Analysis: C, 94.52; H, 5.48/HRMS [M]$^+$: 698
Inv 1-8: Elemental Analysis: C, 94.27; H, 5.73/HRMS [M]$^+$: 738
Inv 1-9: Elemental Analysis: C, 94.85; H, 5.15/HRMS [M]$^+$: 860
Inv 1-10: Elemental Analysis: C, 94.62; H, 5.38/HRMS [M]$^+$: 748
Inv 1-11: Elemental Analysis: C, 94.62; H, 5.38/HRMS [M]$^+$: 748
Inv 1-12: Elemental Analysis: C, 94.62; H, 5.38/HRMS [M]$^+$: 748
Inv 1-13: Elemental Analysis: C, 94.70; H, 5.30/HRMS [M]$^+$: 798
Inv 1-14: Elemental Analysis: C, 94.78; H, 5.22/HRMS [M]$^+$: 848
Inv 1-15: Elemental Analysis: C, 94.70; H, 5.30/HRMS [M]$^+$: 799
Inv 1-16: Elemental Analysis: C, 94.62; H, 5.38/HRMS [M]$^+$: 748

Inv 1-17: Elemental Analysis: C, 94.87; H, 5.13, HRMS [M]$^+$: 746

Inv 1-18: Elemental Analysis: C, 94.94; H, 5.06/HRMS [M]$^+$: 796

Inv 1-19: Elemental Analysis: C, 94.62; H, 5.38/HRMS [M]$^+$: 748

Inv 1-20: Elemental Analysis: C, 94.62; H, 5.38/HRMS [M]$^+$: 748

Synthesis Example 1-28

Preparation of Inv 1-21

9-Bromo-6,11-bis(9,9-dimethyl-9H-fluoren-2-yl)-13,13-dimethyl-13H-indeno[1,2-b]anthracene (EMI 2) (10 g, 1 eq, 0.014 mol) obtained in Synthesis Example 1-5, naphthalen-2-ylboronic acid (3.0 g, 1.2 eq, 0.016 mol), and Pd(PPh$_3$)$_4$ (0.6 g, 0.03 eq, 5.1 mmol) were placed in a flask, an aqueous saturated 2M K$_2$CO$_3$ solution (15 ml) and toluene (150 ml) were dissolved therein and the reaction mixture was stirred for 12 hours while heating. After the reaction was terminated, the reaction solution was filtered through celite, extracted with MC and purified by column chromatography to give Inv 1-21 (9.3 g, yield=83%).

Inv 1-21: Elemental Analysis: C, 93.99; H, 6.01/HRMS [M]$^+$: 804

Synthesis Examples 1-29~1-47

Preparation of Inv 1-22~Inv 1-40

Inv 1-22~Inv 1-40 were obtained as pale yellow solids according to the same procedure as in Synthesis Example 1-28 except for using corresponding starting materials instead of naphthalen-2-ylboronic acid.

Inv 1-22: Elemental Analysis: C, 93.99; H, 6.01/HRMS [M]$^+$: 804

Inv 1-23: Elemental Analysis: C, 94.11; H, 5.89/HRMS [M]$^+$: 854

Inv 1-24: Elemental Analysis: C, 94.11; H, 5.89/HRMS [M]$^+$: 854

Inv 1-25: Elemental Analysis: C, 93.94; H, 6.06/HRMS [M]$^+$: 830

Inv 1-26: Elemental Analysis: C, 93.94; H, 6.06/HRMS [M]$^+$: 830

Inv 1-27: Elemental Analysis: C, 93.94; H, 6.06/HRMS [M]$^+$: 830

Inv 1-28: Elemental Analysis: C, 93.75; H, 6.25/HRMS [M]$^+$: 870

Inv 1-29: Elemental Analysis: C, 94.32; H, 5.68/HRMS [M]$^+$: 992

Inv 1-30: Elemental Analysis: C, 94.05; H, 5.95/HRMS [M]$^+$: 880

Inv 1-31: Elemental Analysis: C, 94.05; H, 5.95/HRMS [M]$^+$: 880

Inv 1-32: Elemental Analysis: C, 94.05; H, 5.95/HRMS [M]$^+$: 880

Inv 1-33: Elemental Analysis: C, 94.16; H, 5.84/HRMS [M]$^+$: 930

Inv 1-34: Elemental Analysis: C, 94.25; H, 5.75/HRMS [M]$^+$: 980

Inv 1-35: Elemental Analysis: C, 94.16; H, 5.84/HRMS [M]$^+$: 930

Inv 1-36: Elemental Analysis: C, 94.05; H, 5.95/HRMS [M]$^+$: 880

Inv 1-37: Elemental Analysis: C, 94.27; H, 5.73/HRMS [M]$^+$: 878

Inv 1-38: Elemental Analysis: C, 94.36; H, 5.64/HRMS [M]$^+$: 928

Inv 1-39: Elemental Analysis: C, 94.05; H, 5.95/HRMS [M]$^+$: 880

Inv 1-40: Elemental Analysis: C, 94.05; H, 5.95/HRMS [M]$^+$: 880

Synthesis Example 1-48

Preparation of Inv 1-41

9-Bromo-6,11-bis(9,9-dimethyl-9H-fluoren-2-yl)-13,13-dimethyl-13H-indeno[1,2-b]anthracene (EMI3) (10 g, 1 eq, 0.014 mol) obtained in Synthesis Example 1-6, naphthalen-2-ylboronic acid (3.0 g, 1.2 eq, 0.016 mol), and Pd(PPh$_3$)$_4$ (0.6 g, 0.03 eq, 5.1 mmol) were placed in a flask, an aqueous saturated 2M K$_2$CO$_3$ solution (15 ml) and toluene (150 ml) were dissolved therein and the reaction mixture was stirred for 12 hours while heating. After the reaction was terminated, the reaction solution was filtered through celite, extracted with MC, and purified by column chromatography to give Inv 1-41 (9.3 g, yield=83%).

Inv 1-41: Elemental Analysis: C, 93.99; H, 6.01/HRMS [M]$^+$: 804

Synthesis Examples 1-49~1-57

Preparation of Inv 1-42~Inv 1-50

Inv 1-42~Inv 1-50 were obtained as pale yellow solids according to the same procedure as in Synthesis Example 1-48 except for using corresponding starting materials instead of naphthalen-2-ylboronic acid.

Inv 1-42: Elemental Analysis: C, 93.99; H, 6.01/HRMS [M]$^+$: 804

Inv 1-43: Elemental Analysis: C, 94.54; H, 5.46/HRMS [M]$^+$: 774

Inv 1-44: Elemental Analysis: C, 94.36; H, 5.64/HRMS [M]$^+$: 750

Inv 1-45: Elemental Analysis: C, 94.14; H, 5.86/HRMS [M]$^+$: 790

Inv 1-46: Elemental Analysis: C, 94.36; H, 5.64/HRMS [M]$^+$: 750

Inv 1-47: Elemental Analysis: C, 94.70; H, 5.30/HRMS [M]$^+$: 912

Inv 1-48: Elemental Analysis: C, 94.46; H, 5.54/HRMS [M]$^+$: 800

Inv 1-49: Elemental Analysis: C, 94.70; H, 5.30/HRMS [M]$^+$: 799

Inv 1-50: Elemental Analysis: C, 94.78; H, 5.22/HRMS [M]$^+$: 848

Synthesis Example 1-58

Preparation of Inv 1-51

9-Bromo-6,11-di(fluoranthen-3-yl)-13,13-dimethyl-13H-indeno[1,2-b]anthracene (EMI4) (10 g, 1 eq, 0.012 mol) obtained in Synthesis Example 1-7, naphthalen-2-ylboronic acid (2.9 g, 1.2 eq, 0.015 mol), and Pd(PPh$_3$)$_4$ (0.52 g, 0.03 eq, 4.6 mmol) were placed in a flask, an aqueous saturated 2M K$_2$CO$_3$ solution (15 ml) and toluene (150 ml) were dissolved therein and the reaction mixture was stirred for 12 hours while heating. After the reaction was terminated, the reaction solution was filtered through celite, extracted with MC, and purified by column chromatography to give Inv 1-51 (7.8 g, yield=80%).

Inv 1-51: Elemental Analysis: C, 95.09; H, 4.91/HRMS [M]$^+$: 820

Synthesis Examples 1-59~1-67

Preparation of Inv 1-52~Inv 1-60

Inv 1-52~Inv 1-60 were obtained as pale yellow solids according to the same procedure as in Synthesis Example 1-58 except for using corresponding starting materials instead of naphthalen-2-ylboronic acid.

Inv 1-52: Elemental Analysis: C, 94.78; H, 5.22/HRMS [M]$^+$: 848
Inv 1-53: Elemental Analysis: C, 95.14; H, 4.86/HRMS [M]$^+$: 870
Inv 1-54: Elemental Analysis: C, 95.00; H, 5.00/HRMS [M]$^+$: 846
Inv 1-55: Elemental Analysis: C, 94.77; H, 5.23/HRMS [M]$^+$: 886
Inv 1-56: Elemental Analysis: C, 95.00; H, 5.00/HRMS [M]$^+$: 846
Inv 1-57: Elemental Analysis: C, 95.21; H, 4.79/HRMS [M]$^+$: 1008
Inv 1-58: Elemental Analysis: C, 95.06; H, 4.94/HRMS [M]$^+$: 896
Inv 1-59: Elemental Analysis: C, 95.27; H, 4.73/HRMS [M]$^+$: 894
Inv 1-60: Elemental Analysis: C, 95.31; H, 4.69/HRMS [M]$^+$: 944

[Reaction Scheme 5]

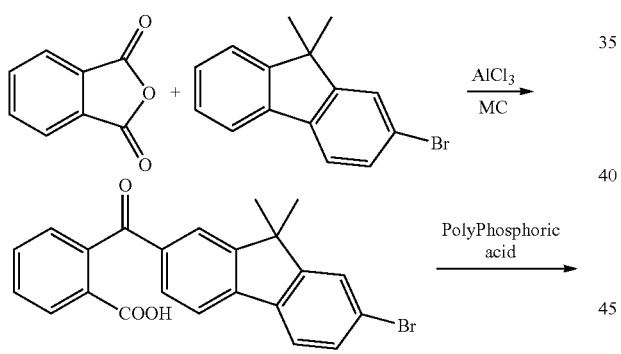

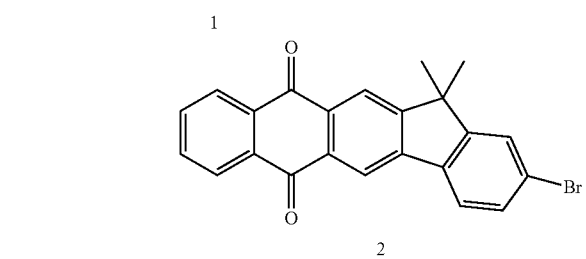

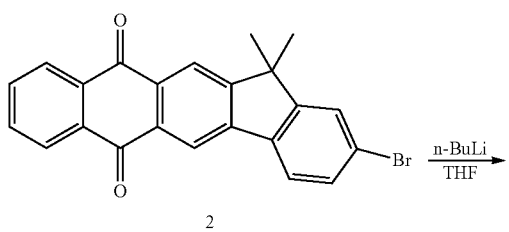

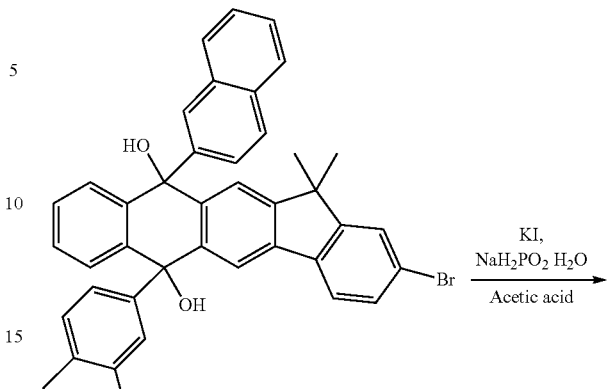

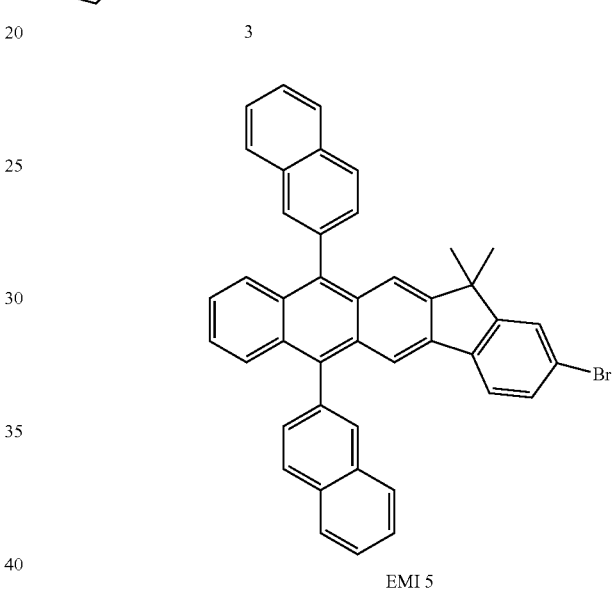

Synthesis Example 2-1

Preparation of 2-(7-bromo-9,9-dimethyl-9H-fluorene-2-carbonyl)benzoic acid of Reaction Scheme 5

2-Bromo-9,9-dimethyl-9H-fluorene (40 g, 1 eq, 0.146 mol) and phthalic anhydride (23.8 g, 1.1 eq, 0.161 mol) were placed in a reaction vessel, and dichloromethane (1 l) was added thereto. Aluminum chloride (29.2 g, 1.5 eq, 0.219 mol) was gradually added at 0° C., and the reaction mixture was stirred at room temperature for 12 hours. After the reaction was terminated, distilled water was gradually added at 0° C., and the reaction solution was extracted with an excess of dichloromethane and several times washed with distilled water. After solvent removal, the resultant solid was placed in a hexane (2 l)-containing vessel, washed, filtered, and dried to give 2-(7-bromo-9,9-dimethyl-9H-fluorene-2-carbonyl)benzoic acid (50.4 g, yield=82%).

$^1$H-NMR: 8.44 (t, 1H), 8.23 (d, 1H), 7.96 (m, 6H), 7.72 (m, 5H), 7.55 (t, 1H), 1.67 (s, 6H).

Synthesis Example 2-2

Preparation of 2-bromo-13,13-dimethyl-6H-indeno[1,2-b]anthracene-6,11(13H)-dione of Reaction Scheme 5

2-(7-Bromo-9,9-dimethyl-9H-fluorene-2-carbonyl)benzoic acid (20 g, 1 eq, 0.047 mol) was placed in a flask, and polyphosphoric acid (50 ml) was added thereto. The reaction mixture was heated at 140° C. for two hours and cooled to less than 50° C., and distilled water was gradually added thereto. The resultant solid was filtered, washed with a small amount of methanol, and dried to give 2-bromo-13,13-dimethyl-6H-indeno[1,2-b]anthracene-6,11(13H)-dione (16.6 g, yield=81%).

$^1$H-NMR: 8.29 (t, 2H), 8.09 (s, 2H), 7.85 (d, 2H), 7.72 (m, 3H), 1.67 (s, 6H).

Synthesis Example 2-3

Preparation of 2-bromo-13,13-dimethyl-6,11-di(naphthalen-2-yl)-11,13-dihydro-6H-indeno[1,2-b]anthracene-6,11-diol of Reaction Scheme 5

2-Bromonaphthrene (4.96 g, 2.2 eq, 0.054 mol) was placed in a flask, and THF (200 ml) was added thereto. Then, n-BuLi (38.4 ml, 2.5 eq, 0.06 mol) was gradually added at −78° C., and the reaction mixture was stirred for one hour. 2-Bromo-13,13-dimethyl-6H-indeno[1,2-b]anthracene-6,11(13H)-dione (10 g, 1 eq, 0.024 mol) was then added and the reaction mixture was stirred at room temperature for 17 hours. After the reaction was terminated, the reaction solution was washed with distilled water, extracted with ethyl acetate, and purified by column chromatography to give 2-bromo-13,13-dimethyl-6,11-di(naphthalen-2-yl)-11,13-dihydro-6H-indeno[1,2-b]anthracene-6,11-diol (11.38 g, yield=72%).

$^1$H-NMR: 8.02 (d, 2H), 7.95 (d, 2H), 7.61 (s, 2H), 7.64 (m, 10H), 7.46 (s, 2H), 7.19 (d, 2H), 1.67 (s, 6H).

Synthesis Example 2-4

Preparation of 2-bromo-13,13-dimethyl-6,11-di(naphthalen-2-yl)-13H-indeno[1,2-b]anthracene (EMI-5) of Reaction Scheme 5

2-Bromo-13,13-dimethyl-6,11-di(naphthalen-2-yl)-11,13-dihydro-6H-indeno[1,2-b]anthracene-6,11-diol (5 g, 1 eq, 0.0075 mol), potassium iodide (12.45 g, 10 eq, 0.075 mol), and sodium hypophosphite (6 g, 5 eq, 0.037 mol) were placed in a flask, and acetic acid (200 ml) was added thereto. The reaction mixture was stirred for five hours while heating. After the reaction was terminated, the reaction solution was added to an excess of distilled water. The resultant solid was washed, filtered, and purified by column chromatography to give a target compound (3.56 g, yield=76%).

$^1$H-NMR: 8.11 (d, 2H), 8.02 (d, 2H), 7.95 (d, 2H), 7.61 (s, 2H), 7.64 (m, 5H), 7.46 (s, 2H), 7.19 (d, 2H), 1.67 (s, 6H).

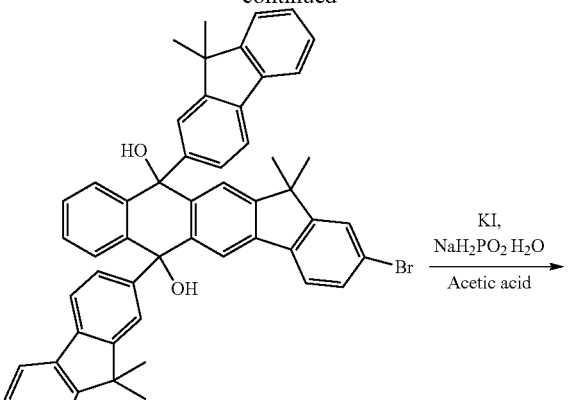

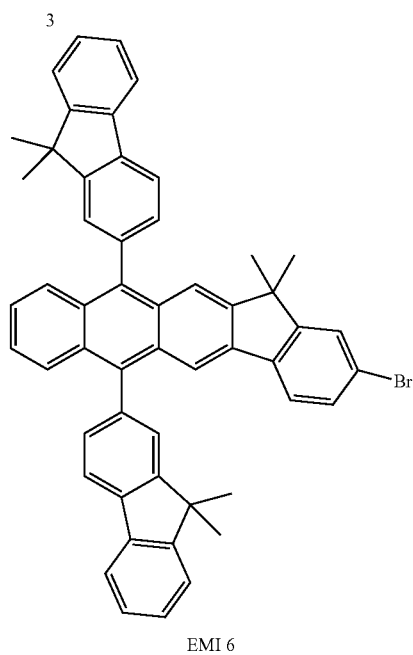

EMI 6

Synthesis Example 2-5

Preparation of EMI6 of Reaction Scheme 6

EMI 6 was synthesized in the same manner as in Synthesis Example 2-3 except for using 2-bromo-9,9-dimethyl-9H-fluorene instead of 2-bromonaphthrene.

Elemental Analysis: C, 84.00; H, 5.45; Br, 10.54/HRMS [M]$^+$: 758.

[Reaction Scheme 6]

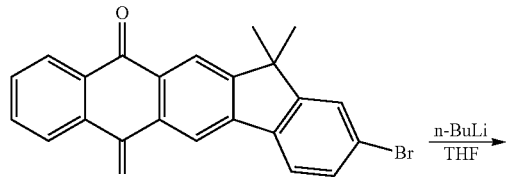

[Reaction Scheme 7]

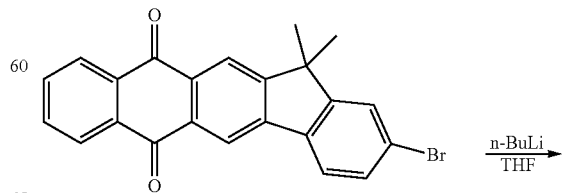

-continued

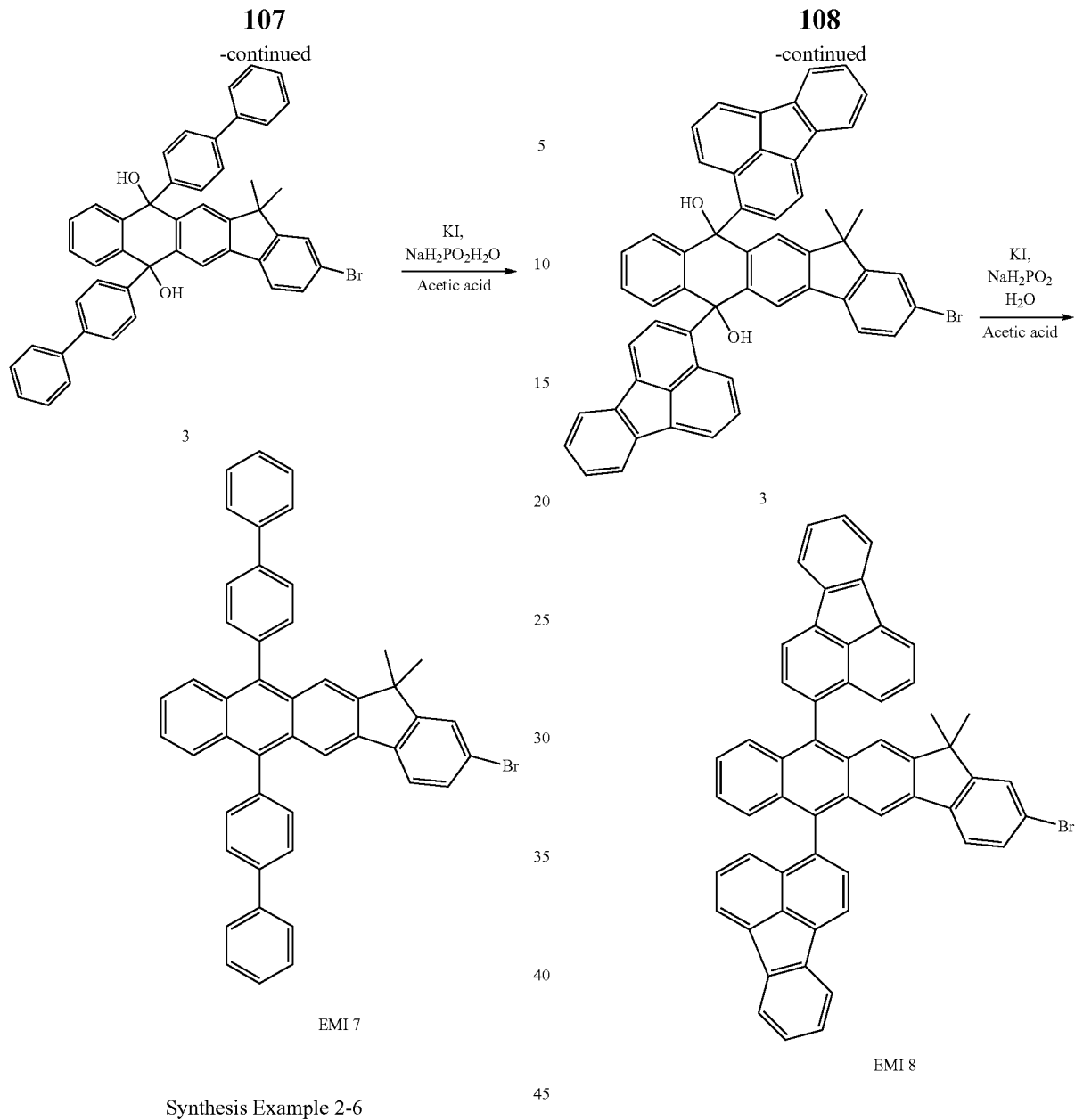

EMI 7

EMI 8

Synthesis Example 2-6

Preparation of EMI 7 of Reaction Scheme 7

EMI 7 was synthesized in the same manner as in Synthesis Example 2-3 except for using 4-bromobiphenyl instead of 2-bromonaphthrene.

Elemental Analysis: C, 83.3; H, 4.91; Br, 11.79/HRMS [M]$^+$: 678.

Synthesis Example 2-7

Preparation of EMI 8 of Reaction Scheme 8

EMI 8 was synthesized in the same manner as in Synthesis Example 2-3 except for using 3-bromofluoranthene instead of 2-bromonaphthrene.

Elemental Analysis: C, 85.37; H, 4.30; Br, 10.33/HRMS [M]$^+$: 774.

Synthesis Example 2-8

Preparation of Inv 2-1

2-Bromo-13,13-dimethyl-6,11-di(naphthalen-2-yl)-13H-indeno[1,2-b]anthracene EMI 5) (10 g, 1 eq, 0.014 mol) obtained in Synthesis Example 2-4, naphthalen-2-ylboronic acid (3.0 g, 1.2 eq, 0.016 mol), and Pd(PPh$_3$)$_4$ (0.6 g, 0.03 eq, 5.1 mmol) were placed in a flask, an aqueous saturated 2M K$_2$CO$_3$ solution (15 ml) and toluene (150 ml) were dissolved

[Reaction Scheme 8]

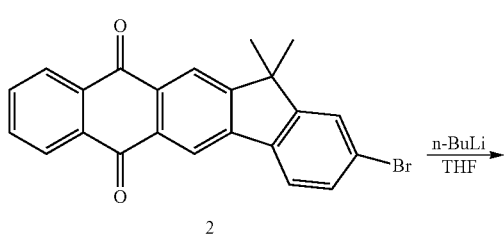

therein and the reaction mixture was stirred for 12 hours while heating. After the reaction was terminated, the reaction solution was filtered through celite, extracted with MC, and purified by column chromatography to give Inv 2-1 (9.3 g, yield=83%).

$^1$H-NMR: 8.11 (d, 3H), 8.02 (d, 3H), 7.95 (d, 3H), 7.61 (m, 5H), 7.64 (m, 5H), 7.46 (m, 3H), 7.19 (d, 2H), 1.67 (s, 6H).

Elemental Analysis: C, 94.61; H, 5.39/HRMS [M]$^+$: 672.

Synthesis Example 2-9

Preparation of Inv 2-2

2-Bromo-13,13-dimethyl-6,11-di(naphthalen-2-yl)-13H-indeno[1,2-b]anthracene (EMI 5) (10 g, 1 eq, 0.014 mmol) obtained in Synthesis Example 2-4, 10-(naphthalen-2-yl)anthracen-9-ylboronic acid (6.5 g, 1.2 eq, 0.016 mol), and Pd(PPh$_3$)$_4$ (0.6 g, 0.03 eq, 5.1 mmol) were placed in a flask, an aqueous saturated 2M K$_2$CO$_3$ solution (15 ml) and toluene (150 ml) were dissolved therein and the reaction mixture was stirred for 12 hours while heating. After the reaction was terminated, the reaction solution was filtered through celite, extracted with MC and purified by column chromatography to give Inv 2-2 (10.4 g, yield=82%).

$^1$H-NMR: 8.11 (m, 6H), 7.95 (m, 6H), 7.61 (m, 4H), 7.64 (s, 5H), 7.46 (m, 6H), 7.19 (m, 4H), 1.67 (s, 6H).

Elemental Analysis: C, 94.61; H, 5.39/HRMS [M]$^+$: 672.

Synthesis Example 2-10

Preparation of Inv 2-3

2-Bromo-13,13-dimethyl-6,11-di(naphthalen-2-yl)-13H-indeno[1,2-b]anthracene (EMI 5) (10 g, 1 eq, 0.014 mol) obtained in Synthesis Example 2-4, 3-(naphthalen-2-yl)phenylboronic acid (4.7 g, 1.2 eq, 0.016 mol), and Pd(PPh$_3$)$_4$ (0.6 g, 0.03 eq, 5.1 mmol) were placed in a flask, an aqueous saturated 2M K$_2$CO$_3$ solution (15 ml) and toluene (150 ml) were dissolved therein, and the reaction mixture was stirred for 12 hours while heating. After the reaction was terminated, the reaction solution was filtered through celite, extracted with MC and purified by column chromatography to give Inv 2-3 (9.9 g, yield=88%).

$^1$H-NMR: 8.11 (m, 6H), 7.95 (m, 6H), 7.61 (m, 4H), 7.64 (s, 5H), 7.46 (m, 6H), 7.27 (d, 3H), 7.19 (m, 4H), 1.67 (s, 6H).

Elemental Analysis: C, 94.70; H, 5.30/HRMS [M]$^+$: 772

Synthesis Examples 2-11~2-19

Preparation of Inv 2-4~Inv 2-12

Inv 2-4~2-12 were obtained as pale yellow solids according to the same procedure as in Synthesis Example 2-8 except for using corresponding starting materials instead of naphthalen-2-ylboronic acid.

Inv 2-4: Elemental Analysis: C, 94.52; H, 5.48/HRMS [M]$^+$: 698

Inv 2-5: Elemental Analysis: C, 94.52; H, 5.48/HRMS [M]$^+$: 698

Inv 2-6: Elemental Analysis: C, 94.52; H, 5.48/HRMS [M]$^+$: 698

Inv 2-7: Elemental Analysis: C, 94.27; H, 5.73/HRMS [M]$^+$: 738

Inv 2-8: Elemental Analysis: C, 94.85; H, 5.15/HRMS [M]$^+$: 860

Inv 2-9: Elemental Analysis: C, 94.62; H, 5.38/HRMS [M]$^+$: 746

Inv 2-10: Elemental Analysis: C, 94.87; H, 5.13/HRMS [M]$^+$: 746

Inv 2-11: Elemental Analysis: C, 94.94; H, 5.06/HRMS [M]$^+$: 796

Inv 2-12: Elemental Analysis: C, 94.62; H, 5.38/HRMS [M]$^+$: 748

Synthesis Example 2-20

Preparation of Inv 2-13

6,11-Bis(9,9-dimethyl-9H-fluoren-2-yl)-13,13-dimethyl-13H-indeno[1,2-b]anthracene (EMI 6) (10 g, 1 eq, 0.014 mol) obtained in Synthesis Example 2-5, naphthalen-2-ylboronic acid (3.0 g, 1.2 eq, 0.016 mol), and Pd(PPh$_3$)$_4$ (0.6 g, 0.03 eq, 5.1 mmol) were placed in a flask, an aqueous saturated 2M K$_2$CO$_3$ solution (15 ml) and toluene (150 ml) were dissolved therein and the reaction mixture was stirred for 12 hours while heating. After the reaction was terminated, the reaction solution was filtered through celite, extracted with MC and purified by column chromatography to give Inv 2-13 (9.3 g, yield=83%).

Inv 2-13: Elemental Analysis: C, 93.99; H, 6.01/HRMS [M]$^+$: 804

Synthesis Examples 2-21~2-31

Preparation of Inv 2-14~Inv 2-24

Inv 2-14~2-24 were obtained as pale yellow solids according to the same procedure as in Synthesis Example 2-20 except for using corresponding starting materials instead of naphthalen-2-ylboronic acid.

Inv 2-14: Elemental Analysis: C, 93.99; H, 6.01/HRMS [M]$^+$: 804

Inv 2-15: Elemental Analysis: C, 94.11; H, 5.89/HRMS [M]$^+$: 854

Inv 2-16: Elemental Analysis: C, 93.94; H, 6.06/HRMS [M]$^+$: 830

Inv 2-17: Elemental Analysis: C, 93.94; H, 6.06/HRMS [M]$^+$: 830

Inv 2-18: Elemental Analysis: C, 93.94; H, 6.06/HRMS [M]$^+$: 830

Inv 2-19: Elemental Analysis: C, 93.75; H, 6.25/HRMS [M]$^+$: 870

Inv 2-20: Elemental Analysis: C, 94.27; H, 5.73/HRMS [M]$^+$: 992

Inv 2-21: Elemental Analysis: C, 94.05; H, 5.95/HRMS [M]$^+$: 879

Inv 2-22: Elemental Analysis: C, 94.27; H, 5.73/HRMS [M]$^+$: 878

Inv 2-23: Elemental Analysis: C, 94.36; H, 5.64/HRMS [M]$^+$: 928

Inv 2-24: Elemental Analysis: C, 94.05; H, 5.95/HRMS [M]$^+$: 880

Synthesis Example 2-32

Preparation of Inv 2-25

9-Bromo-6,11-bis(9,9-dimethyl-9H-fluoren-2-yl)-13,13-dimethyl-13H-indeno[1,2-b]anthracene (EMI 7) (10 g, 1 eq, 0.014 mol) obtained in Synthesis Example 2-6, naphthalen-2-ylboronic acid (3.0 g, 1.2 eq, 0.016 mol), and Pd(PPh$_3$)$_4$ (0.6 g, 0.03 eq, 5.1 mmol) were placed in a flask, an aqueous saturated 2M K$_2$CO$_3$ solution (15 ml) and toluene (150 ml) were dissolved therein and the reaction mixture was stirred for 12 hours while heating. After the reaction was terminated, the reaction solution was filtered through celite, extracted with MC and purified by column chromatography to give Inv 2-25 (9.3 g, yield=83%).

Inv 2-25: Elemental Analysis: C, 93.99; H, 6.01/HRMS [M]$^+$: 804

Synthesis Examples 2-33~2-43

Preparation of Inv 2-26~Inv 2-36

Inv 2-26~2-36 were obtained as pale yellow solids according to the same procedure as in Synthesis Example 2-32 except for using corresponding starting materials instead of naphthalen-2-ylboronic acid.

Inv 2-26: Elemental Analysis: C, 93.99; H, 6.01/HRMS [M]$^+$: 804
Inv 2-27: Elemental Analysis: C, 94.54; H, 5.46/HRMS [M]$^+$: 774
Inv 2-28: Elemental Analysis: C, 94.36; H, 5.64/HRMS [M]$^+$: 750
Inv 2-29: Elemental Analysis: C, 94.36; H, 5.64/HRMS [M]$^+$: 750
Inv 2-30: Elemental Analysis: C, 94.36; H, 5.64/HRMS [M]$^+$: 750
Inv 2-31: Elemental Analysis: C, 94.14; H, 5.86/HRMS [M]$^+$: 790
Inv 2-32: Elemental Analysis: C, 94.70; H, 5.30/HRMS [M]$^+$: 912
Inv 2-33: Elemental Analysis: C, 94.46; H, 5.54/HRMS [M]$^+$: 800
Inv 2-34: Elemental Analysis: C, 94.70; H, 5.30/HRMS [M]$^+$: 799
Inv 2-35: Elemental Analysis: C, 94.78; H, 5.22/HRMS [M]$^+$: 848
Inv 2-36: Elemental Analysis: C, 94.46; H, 5.54/HRMS [M]$^+$: 800

Synthesis Example 2-44

Preparation of Inv 2-37

9-Bromo-6,11-di(fluoranthen-3-yl)-13,13-dimethyl-13H-indeno[1,2-b]anthracene (EMI 8) (10 g, 1 eq, 0.012 mol) obtained in Synthesis Example 2-7, naphthalen-2-ylboronic acid (2.9 g, 1.2 eq, 0.015 mol), and Pd(PPh$_3$)$_4$ (0.52 g, 0.03 eq, 4.6 mmol) were placed in a flask, an aqueous saturated 2M K$_2$CO$_3$ solution (15 ml) and toluene (150 ml) were dissolved therein and the reaction mixture was stirred for 12 hours while heating. After the reaction was terminated, the reaction solution was filtered through celite, extracted with MC, and purified by column chromatography to give Inv 2-37 (7.8 g, yield=80%).

Inv 2-37: Elemental Analysis: C, 95.09; H, 4.91/HRMS [M]$^+$: 820

Synthesis Example 2-45~2-55

Preparation of Inv 2-38~Inv 2-48

Inv 2-38~2-48 were obtained as pale yellow solids according to the same procedure as in Synthesis Example 2-44 except for using corresponding starting materials instead of naphthalen-2-ylboronic acid.

Inv 2-38: Elemental Analysis: C, 94.78; H, 5.22/HRMS [M]$^+$: 848

Inv 2-39: Elemental Analysis: C, 95.14; H, 4.86/HRMS [M]$^+$: 870
Inv 2-40: Elemental Analysis: C, 95.00; H, 5.00/HRMS [M]$^+$: 846
Inv 2-41: Elemental Analysis: C, 95.00; H, 5.00/HRMS [M]$^+$: 846
Inv 2-42: Elemental Analysis: C, 95.00; H, 5.00/HRMS [M]$^+$: 846
Inv 2-43: Elemental Analysis: C, 94.77; H, 5.23/HRMS [M]$^+$: 886
Inv 2-44: Elemental Analysis: C, 95.00; H, 5.00/HRMS [M]$^+$: 846
Inv 2-45: Elemental Analysis: C, 95.21; H, 4.79/HRMS [M]$^+$: 1008
Inv 2-46: Elemental Analysis: C, 95.06; H, 4.94/HRMS [M]$^+$: 896
Inv 2-47: Elemental Analysis: C, 95.27; H, 4.73/HRMS [M]$^+$: 894
Inv 2-48: Elemental Analysis: C, 95.31; H, 4.69/HRMS [M]$^+$: 944

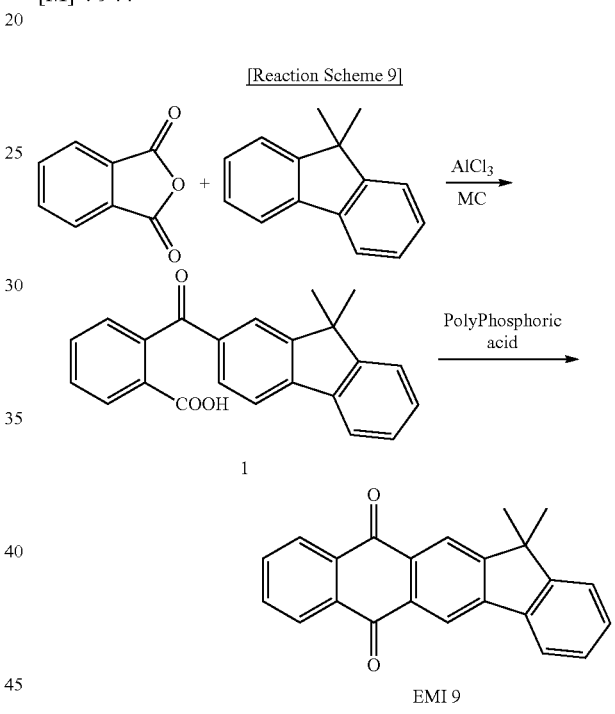

Synthesis Example 3-1

Preparation of 2-(9,9-dimethyl-9H-fluorene-2-carbonyl)benzoic acid of Reaction Scheme 9

9,9-Dimethyl-9H-fluorene (40 g, 1 eq, 0.146 mol) and phthalic anhydride (36.5 g, 1.1 eq, 0.161 mol) were placed in a reaction vessel, and dichloromethane (1.5 l) was added thereto. Then, aluminum chloride (29.2 g, 1.5 eq, 0.219 mol) was gradually added at 0° C., and the reaction mixture was stirred at room temperature for 12 hours. After the reaction was terminated, distilled water was gradually added at 0° C., and the resultant solution was extracted with an excess of dichloromethane and several times washed with distilled water. After solvent removal, the resultant solid was placed in a hexane (2 l)-containing vessel, washed, filtered, and dried to give 2-(9,9-dimethyl-9H-fluorene-2-carbonyl)benzoic acid (59.8 g, yield=82%).

¹H-NMR: 8.44 (t, 2H), 8.23 (d, 1H), 7.96 (m, 5H), 7.72 (m, 5H), 7.55 (t, 1H), 1.67 (s, 6H).

Synthesis Example 3-2

Preparation of 13,13-dimethyl-6H-indeno[1,2-b] anthracene-6,11(13H)-dione (EMI 9) of Reaction Scheme 9

2-(9,9-Dimethyl-9H-fluorene-2-carbonyl)benzoic acid (20 g, 1 eq, 0.0399 mol) was placed in a flask and polyphosphoric acid (50 ml) was added thereto. The reaction mixture was stirred at 140° C. for two hours while heating and cooled to less than 50° C., and distilled water was gradually added thereto. The resultant solid was filtered, washed with a small amount of methanol and dried to give 13,13-dimethyl-6H-indeno[1,2-b]anthracene-6,11(13H)-dione (EMI-9) (15 g, yield=78%).
¹H-NMR: 8.29 (t, 3H), 8.09 (s, 2H), 7.85 (d, 2H), 7.72 (m, 2H), 1.67 (s, 6H).

[Reaction Scheme 10]

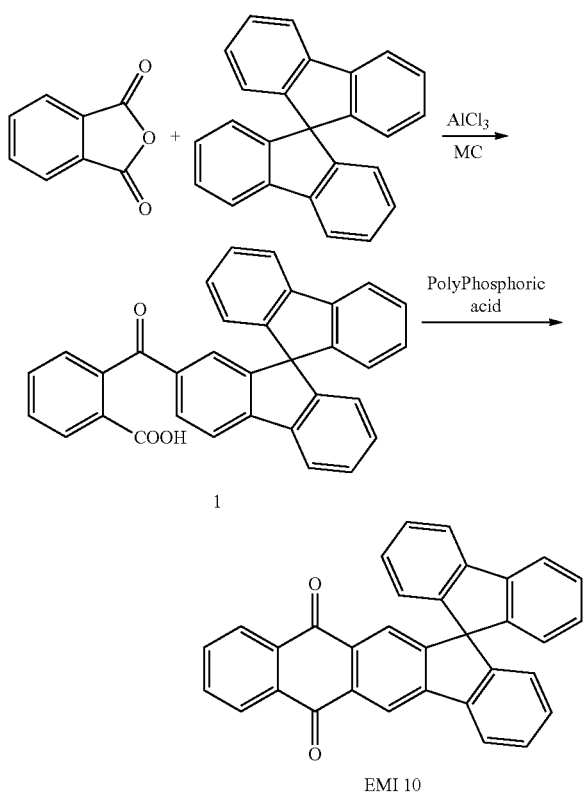

Synthesis Example 3-3

Preparation of 2-(9,9'-spirobi[fluorene]-2-ylcarbonyl)benzoic acid of Reaction Scheme 10

Spirofluorene (10 g, 1 eq, 0.06 mol) and phthalic anhydride (10.2 g, 1.1 eq, 0.069 mol) were placed in a reaction vessel, and dichloromethane (1l) was added thereto. Then, aluminum chloride (13.8 g, 1.5 eq, 0.1 mol) was gradually added at 0° C. and the reaction mixture was stirred at room temperature for 12 hours. After the reaction was terminated, distilled water was gradually added at 0° C., and the resultant solution was extracted with an excess of dichloromethane and several times washed with distilled water. After solvent removal, the resultant solid was placed in a hexane (2 l)-containing vessel, washed, filtered and dried to give 2-(9,9'-spirobi[fluorene]-2-ylcarbonyl)benzoic acid (22 g, yield=82%).
¹H-NMR: 8.44 (t, 2H), 8.23 (d, 1H), 7.96 (m, 5H), 7.72 (m, 5H), 7.55 (t, 1H), 1.67 (s, 6H).

Synthesis Example 3-4

Preparation of spiro[fluorene-9,13'-indeno[1,2-b] anthracene]-6',11'-dione (EMI 10) of Reaction Scheme 10

2-(9,9'-Spirobi[fluorene]-2-ylcarbonyl)benzoic acid (20 g, 1 eq, 0.04 mol) was placed in a flask, and polyphosphoric acid (50 ml) was added thereto. The reaction mixture was stirred at 140° C. for two hours while heating and cooled to less than 50° C., and distilled water was gradually added thereto. The resultant solid was filtered, washed with a small amount of methanol and dried to give spiro[fluorene-9,13'-indeno[1,2-b]anthracene]-6',11'-dione (EMI-10) (15 g, yield=78%).
¹H-NMR: 8.29 (t, 3H), 8.09 (s, 2H), 7.85 (d, 2H), 7.72 (m, 2H), 1.67 (s, 6H).

Synthesis Example 3-5

Preparation of Inv 3-1

2-Bromonaphthrene (5.3 g, 2.2 eq, 0.067 mol) was placed in a flask, THF (200 ml) was dissolved therein, and n-BuLi (45.3 ml, 2.5 eq, 0.075 mol) was gradually added at −78l. The reaction mixture was stirred for one hour, 13,13-dimethyl-13H-indeno[1,2-b]anthracene-6,11-dione (EMI 9) (10 g, 1 eq, 0.03 mol) obtained in Synthesis Example 3-2 was added, and the resultant mixture was stirred at room temperature for 17 hours. After the reaction was terminated, the reaction solution was washed with distilled water, extracted with ethyl acetate and purified by column chromatography to give 13,13-dimethyl-6,11-di(naphthalen-2-yl)-11,13-dihydro-6H-indeno[1,2-b]anthracene-6,11-diol (11.38 g, yield=72%).

13,13-dimethyl-6,11-di(naphthalen-2-yl)-11,13-dihydro-6H-indeno[1,2-b]anthracene-6,11-diol (5 g, 1 eq, 0.0075 mol), potassium iodide (12.45 g, 10 eq, 0.075 mol), and sodium hypophosphite (6 g, 5 eq, 0.037 mol) were placed in a flask, acetic acid (200 ml) was added thereto, and the reaction mixture was stirred for five hours while heating. After the reaction was terminated, the reaction solution was added to an excess of distilled water. The resultant solid was washed, filtered and purified by column chromatography to give 13,13-dimethyl-6,11-di(naphthalen-2-yl)-13H-indeno[1,2-b]anthracene (3.56 g, yield=76%).

Inv 3-1: Elemental Analysis: C, 94.47; H, 5.53/HRMS [M]⁺: 546

Synthesis Examples 3-6~3-33

Preparation of Inv 3-2~Inv 3-29

Inv 3~2~3-29 were obtained as pale yellow solids according to the same procedure as in Synthesis Example 3-5 except for using corresponding starting materials instead of 2-bromonaphthalene.

Inv 3-2: Elemental Analysis: C, 94.28; H, 5.72/HRMS [M]⁺: 598

Inv 3-3: Elemental Analysis: C, 94.28; H, 5.72/HRMS [M]+: 678
Inv 3-4: Elemental Analysis: C, 94.28; H, 5.72/HRMS [M]+: 598
Inv 3-5: Elemental Analysis: C, 94.70; H, 5.30/HRMS [M]+: 646
Inv 3-6: Elemental Analysis: C, 94.70; H, 5.30/HRMS [M]+: 646
Inv 3-7: Elemental Analysis: C, 94.52; H, 5.48/HRMS [M]+: 698
Inv 3-8: Elemental Analysis: C, 94.47; H, 5.53/HRMS [M]+: 546
Inv 3-9: Elemental Analysis: C, 95.07; H, 4.93/HRMS [M]+: 694
Inv 3-10: Elemental Analysis: C, 94.52; H, 5.48/HRMS [M]+: 698
Inv 3-11: Elemental Analysis: C, 95.18; H, 4.82/HRMS [M]+: 794
Inv 3-12: Elemental Analysis: C, 94.70; H, 5.30/HRMS [M]+: 646
Inv 3-13: Elemental Analysis: C, 94.36; H, 5.64/HRMS [M]+: 750
Inv 3-14: Elemental Analysis: C, 94.98; H, 5.02/HRMS [M]+: 922
Inv 3-15: Elemental Analysis: C, 95.18; H, 4.82/HRMS [M]+: 668
Inv 3-16: Elemental Analysis: C, 94.97; H, 5.03/HRMS [M]+: 720
Inv 3-17: Elemental Analysis: C, 94.46; H, 5.54/HRMS [M]+: 800
Inv 3-18: Elemental Analysis: C, 94.97; H, 5.03/HRMS [M]+: 720
Inv 3-19: Elemental Analysis: C, 95.28; H, 4.72/HRMS [M]+: 768
Inv 3-20: Elemental Analysis: C, 95.07; H, 4.93/HRMS [M]+: 694
Inv 3-21: Elemental Analysis: C, 94.52; H, 5.48/HRMS [M]+: 698
Inv 3-22: Elemental Analysis: C, 95.18; H, 4.82/HRMS [M]+: 794
Inv 3-23: Elemental Analysis: C, 94.70; H, 5.30/HRMS [M]+: 646
Inv 3-24: Elemental Analysis: C, 94.36; H, 5.64/HRMS [M]+: 750
Inv 3-25: Elemental Analysis: C, 94.98; H, 5.02/HRMS [M]+: 922
Inv 3-26: Elemental Analysis: C, 95.18; H, 4.82/HRMS [M]+: 668
Inv 3-27: Elemental Analysis: C, 94.97; H, 5.03/HRMS [M]+: 720
Inv 3-28: Elemental Analysis: C, 94.46; H, 5.54/HRMS [M]+: 800
Inv 3-29: Elemental Analysis: C, 94.97; H, 5.03/HRMS [M]+: 720

[Reaction Scheme 11]

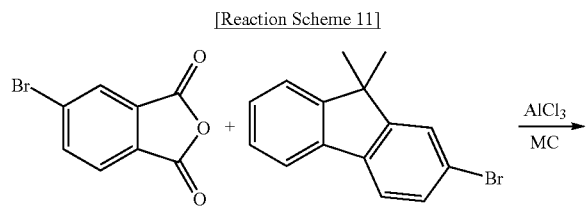

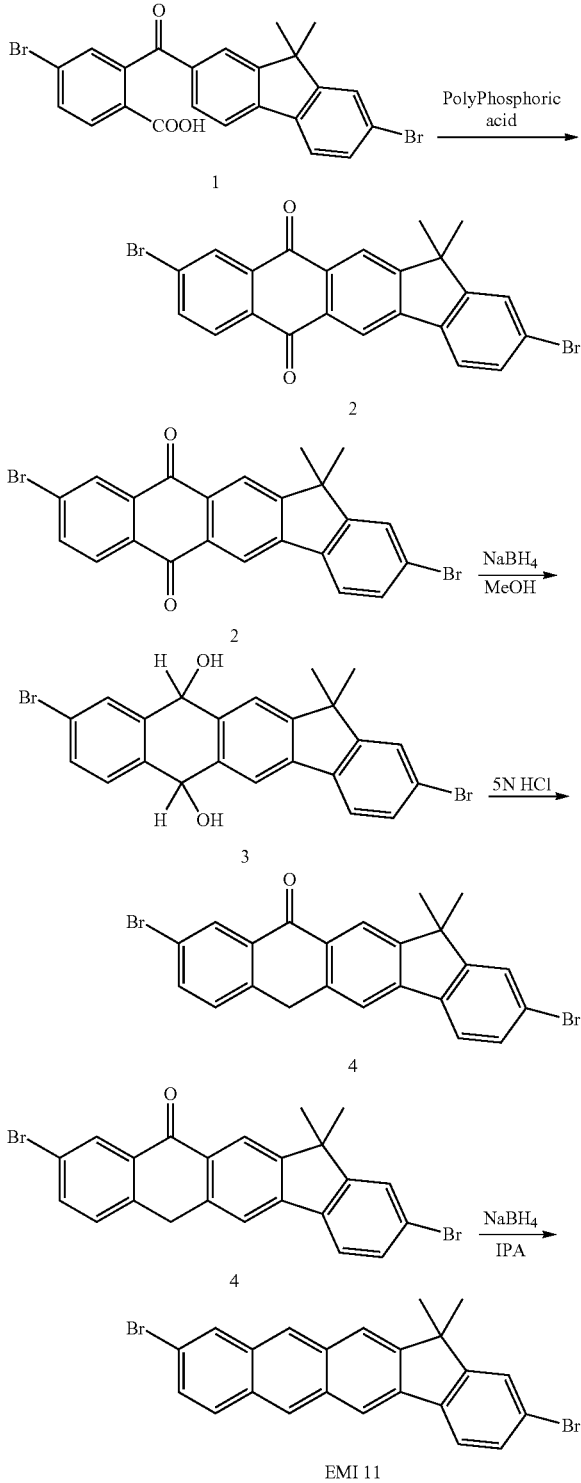

Synthesis Example 4-1

Preparation of 4-bromo-2-(7-bromo-9,9-dimethyl-9H-fluorene-2-carbonyl)-benzoic acid of Reaction Scheme 11

2-Bromo-9,9-dimethyl-9H-fluorene (40 g, 1 eq, 0.146 mol) and 2-bromophthalic anhydride (36.5 g, 1.1 eq, 0.161 mol) were placed in a reaction vessel, and dichloromethane (1.5 l) was added thereto. Then, aluminum chloride (29.2 g, 1.5 eq, 0.219 mol) was gradually added at 0° C., and the reaction mixture was stirred at room temperature for 12 hours. After the reaction was terminated, distilled water was gradually added at 0° C., and the reaction solution was extracted with an excess of dichloromethane, and several times washed with distilled water. After solvent removal, the resultant solid was placed in a hexane (2 l)-containing vessel, washed, filtered and dried to give 4-bromo-2-(7-bromo-9,9-dimethyl-9H-fluorene-2-carbonyl)-benzoic acid (59.8 g, yield=82%).

$^1$H-NMR: 8.44 (t, 1H), 8.23 (d, 1H), 7.96 (m, 5H), 7.72 (m, 5H), 7.55 (t, 1H), 1.67 (s, 6H).

Synthesis Example 4-2

Preparation of 2,9-dibromo-13,13-dimethyl-6H-indeno[1,2-b]anthracene-6,11(13H)-dione of Reaction Scheme 11

4-Bromo-2-(7-bromo-9,9-dimethyl-9H-fluorene-2-carbonyl)-benzoic acid (20 g, 1 eq, 0.0399 mol) was placed in a flask, and polyphosphoric acid (50 ml) was added thereto. The reaction mixture was stirred at 140° C. for two hours while heating and cooled to less than 50° C., and distilled water was gradually added thereto. The resultant solid was filtered, washed with a small amount of methanol, and dried to give 2,9-dibromo-13,13-dimethyl-6H-indeno[1,2-b]anthracene-6,11(13H)-dione (15 g, yield=78%).

$^1$H-NMR: 8.29 (t, 2H), 8.09 (s, 2H), 7.85 (d, 2H), 7.72 (m, 2H), 1.67 (s, 6H).

Synthesis Example 4-3

Preparation of 2,9-dibromo-13,13-dimethyl-11,13-dihydro-6H-indeno[1,2-b]anthracene-6,11-diol of Reaction Scheme 11

2,9-Dibromo-13,13-dimethyl-6H-indeno[1,2-b]anthracene-6,11(13H)-dione (20 g, 1 eq, 0.041 mol) was placed in a flask, and MeOH (150 ml) was added thereto. Then, sodium borohydride (6.2 g, 4 eq, 0.164 mol) was gradually added at 0° C., the reaction mixture was stirred for five hours, and ice water was gradually added thereto. The reaction solution was extracted with MC and recrystallized from hexane to give 2,9-dibromo-13,13-dimethyl-11,13-dihydro-6H-indeno[1,2-b]anthracene-6,11-diol (15 g, yield=78%).

HRMS [M]$^+$: calcd 486.6. found 485.97.

Synthesis Example 4-4

Preparation of 2,9-dibromo-13,13-dimethyl-6H-indeno[1,2-b]anthracen-11(13H)-one of Reaction Scheme 11

2,9-Dibromo-13,13-dimethyl-11,13-dihydro-6H-indeno[1,2-b]anthracene-6,11-diol (15 g, 1 eq, 0.003 mol) was placed in a flask, and 5N HCl (100 ml) was added thereto. The reaction mixture was stirred for five hours while heating. The resultant solid was filtered, several times washed with distilled water and dried to give 2,9-dibromo-13,13-dimethyl-6H-indeno[1,2-b]anthracen-11(13H)-one (13.2 g, yield=92%).

HRMS [M]$^+$: calcd 468.18. found 465.9.

Synthesis Example 4-5

Preparation of 2,9-dibromo-13,13-dimethyl-13H-indeno[1,2-b]anthracene (EMI 11) of Reaction Scheme 11

2,9-Dibromo-13,13-dimethyl-6H-indeno[1,2-b]anthracen-11(13H)-one (13 g, 1 eq, 0.027 mol) was placed in a flask, and IPA (200 ml) was added thereto. Then, sodium borohydride (3.1 g, 3 eq, 0.081 mol) was gradually added at 0° C., the reaction mixture was stirred at 100° C. while heating for 24-36 hours and cooled to room temperature, and ice water was gradually added thereto. The resultant solid was filtered, several times washed with distilled water, dried and purified by column chromatography to give 2,9-dibromo-13,13-dimethyl-13H-indeno[1,2-b]anthracene (EMI 11) (8.5 g, yield=70%).

HRMS [M]$^+$: calcd 452.1 found 449.9.

[Reaction Scheme 12]

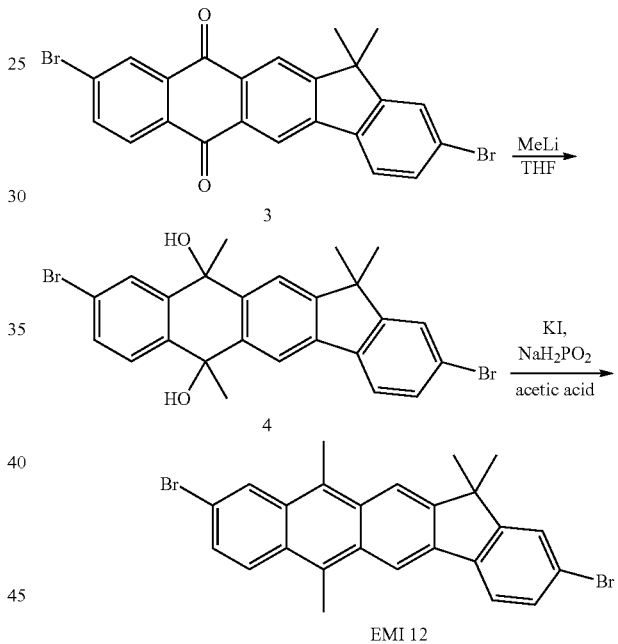

Synthesis Example 4-6

Preparation of 2,9-dibromo-6,11,13,13-tetramethyl-11,13-dihydro-6H-indeno[1,2-b]anthracene-6,11-diol of Reaction Scheme 12

2,9-Dibromo-13,13-dimethyl-6H-indeno[1,2-b]anthracene-6,11(13H)-dione (10 g, 1 eq, 0.02 mol) was placed in a flask, and THF (200 ml) was added thereto. Then, methyllithium (1 g, 2.2 eq, 0.045 mol) was gradually added at 0° C., the reaction mixture was stirred at 60° C. while heating for 12 hours and cooled to room temperature, and ice water was gradually added thereto. The reaction solution was extracted with MC and several times washed with distilled water. After solvent removal, the resultant solid was purified by column chromatography to give 2,9-dibromo-6,11,13,13-tetramethyl-11,13-dihydro-6H-indeno[1,2-b]anthracene-6,11-diol (2.5 g, yield=25%).

Elemental Analysis: C, 58.39; H, 4.31; Br, 31.08; O, 6.22/ HRMS [M]+: 514.

Synthesis Example 4-7

Preparation of 2,9-dibromo-6,11,13,13-tetramethyl-13H-indeno[1,2-b]anthracene (EMI 12) of Reaction Scheme 12

2,9-Dibromo-6,11,13,13-tetramethyl-13H-indeno[1,2-b]anthracene (EMI 12) was synthesized in the same manner as in Synthesis Example 2-4 using 2,9-dibromo-6,11,13,13-tetramethyl-11,13-dihydro-6H-indeno[1,2-b]anthracene-6,11-diol (2.5 g).

Elemental Analysis: C, 62.53; H, 4.20; Br, 33.28/HRMS [M]+: 477.

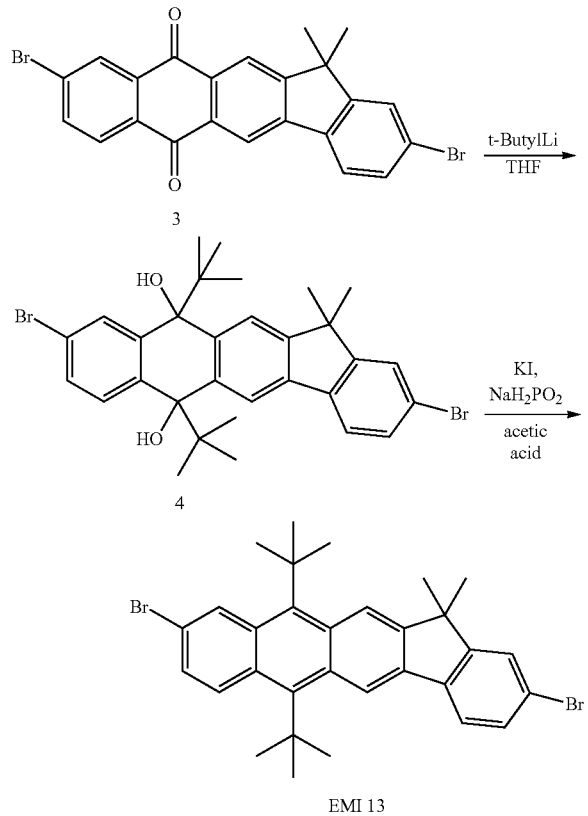

[Reaction Scheme 13]

Synthesis Example 4-8

Preparation of 2,9-dibromo-6,11-di-tert-butyl-13,13-dimethyl-11,13-dihydro-6H-indeno[1,2-b]anthracene-6,11-diol of Reaction Scheme 13

The same procedure as in Synthesis Example 4-6 was performed except for using t-butyllithium instead of methyllithium to give 2,9-dibromo-6,11-di-tert-butyl-13,13-dimethyl-11,13-dihydro-6H-indeno[1,2-b]anthracene-6,11-diol (3.2 g, yield=20%).

Elemental Analysis: C, 62.22; H, 5.73; Br, 27.71; O, 5.35/ HRMS [M]+: 598.

Synthesis Example 4-9

Preparation of 2,9-dibromo-6,11,13,13-tetramethyl-13H-indeno[1,2-b]anthracene (EMI 13) of Reaction Scheme 13

The same procedure as in Synthesis Example 4-7 was performed using 2,9-dibromo-6,11-di-tert-butyl-13,13-dimethyl-11,13-dihydro-6H-indeno[1,2-]anthracene-6,11-diol to give 2,9-dibromo-6,11,13,13-tetramethyl-13H-indeno[1,2-b]anthracene (2 g, yield=77%).

Elemental Analysis: C, 65.97; H, 5.71; Br, 28.31/HRMS [M]+: 564.

Synthesis Example 4-10

Preparation of Inv 4-1

2,9-Dibromo-13,13-dimethyl-13H-indeno[1,2-b]anthracene (EMI 11) (10 g, 1 eq, 0.022 mol) obtained in Synthesis Example 4-5, naphthalen-2-ylboronic acid (6.2 g, 2.2 eq, 0.048 mol), and Pd(PPh$_3$)$_4$ (0.76 g, 0.03 eq, 6.61 mmol) were placed in a flask, an aqueous saturated 2M K$_2$CO$_3$ solution (20 ml) and toluene (300 ml) were dissolved therein and the reaction mixture was stirred for 12 hours while heating. After the reaction was terminated, the reaction solution was filtered through celite, extracted with MC and purified by column chromatography to give Inv 4-1 (9.96 g, yield=83%).

Inv 4-1: Elemental Analysis: C, 94.47; H, 5.53/HRMS [M]+: 546

Synthesis Examples 4-11~4-39

Preparation of Inv 4-2~Inv 4-30

Inv 4-2~4-30 were obtained as pale yellow solids according to the same procedure as in Synthesis Example 4-10 except for using corresponding starting materials instead of naphthalen-2-ylboronic acid.

Inv 4-2: Elemental Analysis: C, 94.47; H, 5.53/HRMS [M]+: 546
Inv 4-3: Elemental Analysis: C, 94.79; H, 5.21/HRMS [M]+: 696
Inv 4-4: Elemental Analysis: C, 94.28; H, 5.72/HRMS [M]+: 698
Inv 4-5: Elemental Analysis: C, 94.28; H, 5.72/HRMS [M]+: 698
Inv 4-6: Elemental Analysis: C, 94.36; H, 5.64/HRMS [M]+: 750
Inv 4-7: Elemental Analysis: C, 94.52; H, 5.48/HRMS [M]+: 698
Inv 4-8: Elemental Analysis: C, 95.07; H, 4.93/HRMS [M]+: 694
Inv 4-9: Elemental Analysis: C, 93.76; H, 6.24/HRMS [M]+: 678
Inv 4-10: Elemental Analysis: C, 94.98; H, 5.02/HRMS [M]+: 923
Inv 4-11: Elemental Analysis: C, 94.04; H, 5.96/HRMS [M]+: 574
Inv 4-12: Elemental Analysis: C, 94.04; H, 5.96/HRMS [M]+: 574
Inv 4-13: Elemental Analysis: C, 94.44; H, 5.56/HRMS [M]+: 724
Inv 4-14: Elemental Analysis: C, 93.89; H, 6.11/HRMS [M]+: 626
Inv 4-15: Elemental Analysis: C, 93.89; H, 6.11/HRMS [M]+: 626

Inv 4-16: Elemental Analysis: C, 94.05; H, 5.95/HRMS [M]⁺: 778

Inv 4-17: Elemental Analysis: C, 94.18; H, 5.82/HRMS [M]⁺: 726

Inv 4-18: Elemental Analysis: C, 94.70; H, 5.30/HRMS [M]⁺: 722

Inv 4-19: Elemental Analysis: C, 93.44; H, 6.56/HRMS [M]⁺: 706

Inv 4-20: Elemental Analysis: C, 94.70; H, 5.30/HRMS [M]⁺: 951

Inv 4-21: Elemental Analysis: C, 94.36; H, 5.64/HRMS [M]⁺: 750

Inv 4-22: Elemental Analysis: C, 94.52; H, 5.48/HRMS [M]⁺: 698

Inv 4-23: Elemental Analysis: C, 95.07; H, 4.93/HRMS [M]⁺: 694

Inv 4-24: Elemental Analysis: C, 93.76; H, 6.24/HRMS [M]⁺: 678

Inv 4-25: Elemental Analysis: C, 94.98; H, 5.02/HRMS [M]⁺: 923

Inv 4-26: Elemental Analysis: C, 94.04; H, 5.96/HRMS [M]⁺: 574

Inv 4-27: Elemental Analysis: C, 94.04; H, 5.96/HRMS [M]⁺: 574

Inv 4-28: Elemental Analysis: C, 94.44; H, 5.56/HRMS [M]⁺: 724

Inv 4-29: Elemental Analysis: C, 93.89; H, 6.11/HRMS [M]⁺: 626

Inv 4-30: Elemental Analysis: C, 93.89; H, 6.11/HRMS [M]⁺: 626

[Reaction Scheme 14]

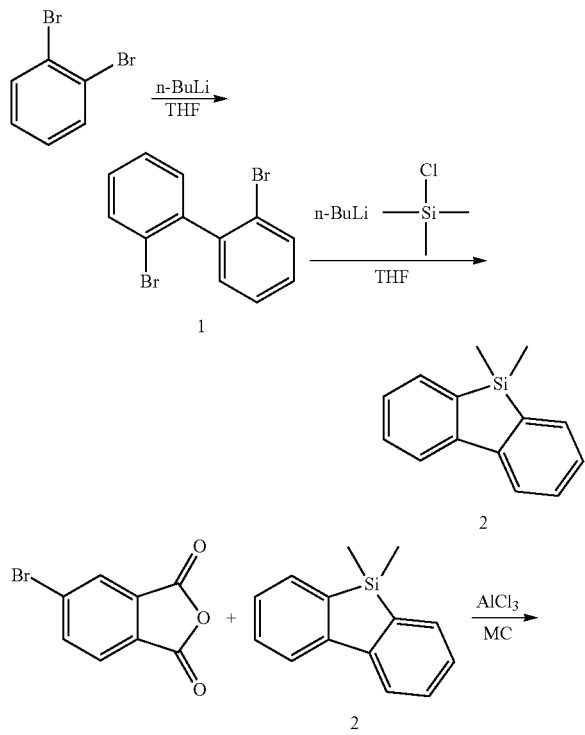

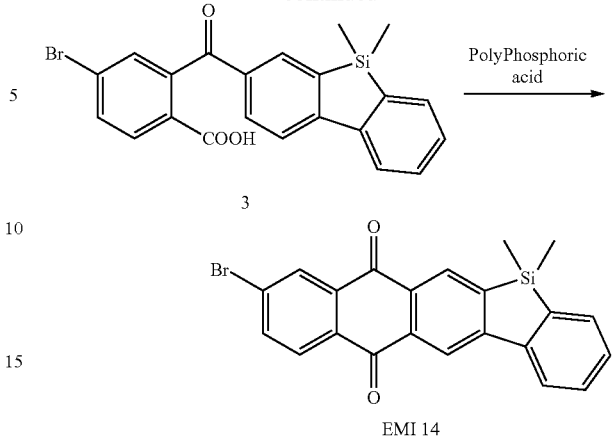

EMI 14

Synthesis Example 5-1

Preparation of 2,2'-dibromobiphenyl of Reaction Scheme 14

1,2-Dibromobenzene (10 g, 1 eq, 0.042 mol) was placed in a flask and THF (150 ml) was added thereto. Then, n-butyl-lithium (14.2 ml, 0.5 eq, 0.021 mol) was gradually added at −78° C. and heated to room temperature. The reaction mixture was stirred for one hour, distilled water was added thereto, and the resultant solution was stirred for one minute. The reaction solution was extracted with hexane, dried to remove the solvent, and purified by column chromatography to give 2,2'-dibromobiphenyl (5 g, yield=65%).

Elemental Analysis: C, 46.20; H, 2.58; Br, 51.22/HRMS [M]⁺: 312.

Synthesis Example 5-2

Preparation of 5,5-dimethyl-5H-dibenzo[b,d]silole of Reaction Scheme 14

1,2-Dibromobiphenyl (10 g, 1 eq, 0.032 mol) was placed in a flask, and THF (150 ml) was added thereto. Then, n-buth-yllithium (24.1 ml, 1.2 eq, 0.038 mol) was gradually added at −78° C., the reaction mixture was stirred for 30 minutes, and chlorotrimethylsilane (4.1 g, 1.2 eq, 0.038 mol) was added thereto. The resultant solution was stirred for four hours and distilled water was added thereto, followed by stirring for about 10 minutes. The reaction solution was extracted with hexane, dried to remove the solvent and purified by column chromatography to give 5,5-dimethyl-5H-dibenzo[b,d]silole (5.17 g, yield=77%).

Elemental Analysis: C, 79.94; H, 6.71; Si, 13.35/HRMS [M]⁺: 210.

Synthesis Example 5-3

Preparation of 4-bromo-2-(5,5-dimethyl-5H-dibenzo [b,d]silole-3-carbonyl)benzoic acid of Reaction Scheme 14

5,5-Dimethyl-5H-dibenzo[b,d]silole (5 g, 1 eq, 0.023 mol) and 2-bromophthalic anhydride (5.7 g, 1.1 eq, 0.025 mol) were placed in a flask, and dichloromethane (200 ml) was added thereto. Then, aluminum chloride (4.5 g, 1.5 eq, 0.0345 mol) was gradually added at 0° C. and the reaction mixture was stirred at room temperature for 12 hours. After the reaction was terminated, distilled water was gradually added thereto at 0° C., and the reaction solution was extracted with an excess of dichloromethane and several times washed with distilled water. After solvent removal, the resultant solid was placed in a hexane (500 ml)-containing vessel, washed, filtered, and dried to give 4-bromo-2-(5,5-dimethyl-5H-dibenzo[b,d]silole-3-carbonyl)benzoic acid (6.5 g, yield=65%).

Elemental Analysis: C, 60.42; H, 3.92; Br, 18.27; 0, 10.97; Si, 6.42

HRMS [M]$^+$: 436.

Synthesis Example 5-4

Preparation of 9-bromo-5,5-dimethyl-5H-anthra[2,3-b]benzo[d]silole-7,12-dione (EMI 14) of Reaction Scheme 14

4-Bromo-2-(5,5-dimethyl-5H-dibenzo[b,d]silole-3-carbonyl)benzoic acid (5 g, 1 eq, 0.011 mol) was placed in a flask, and polyphosphoric acid (50 ml) was added thereto. The reaction mixture was stirred at 140° C. for two hours while heating and cooled to less than 50° C., and distilled water was gradually added thereto. The resultant solid was filtered, washed with a small amount of methanol and dried to give 9-bromo-5,5-dimethyl-5H-anthra[2,3-b]benzo[d]silole-7,12-dione (EMI 14) (4.5 g, yield=72%).

Elemental Analysis: C, 63.01; H, 3.61; Br, 19.05; 0, 7.63; Si, 6.70

HRMS [M]$^+$: 418

Synthesis Example 5-5

Preparation of Inv 5-1

EMI 14 (10 g, 1 eq, 0.016 mol) obtained in Synthesis Example 5-4, naphthalen-2-ylboronic acid (3.2 g, 1.2 eq, 0.019 mol), and Pd(PPh$_3$)$_4$ (0.65 g, 0.03 eq, 5.7 mmol) were placed in a flask, an aqueous saturated 2M K$_2$CO$_3$ solution (15 ml) and toluene (150 ml) were dissolved therein and stirred for 12 hours while heating. After the reaction was terminated, the reaction solution was filtered through celite, extracted with MC and purified by column chromatography to give Inv 5-1 (13,13-dimethyl-6,9,11-tri(naphthalen-2-yl)-13H-indeno[1,2-b]anthracene (9.5 g, yield=88.7%).

Inv 5-1: Elemental Analysis: C, 94.61; H, 5.39/HRMS [M]$^+$: 672.

Synthesis Examples 5-6~5-51

Preparation of Inv 5-2~Inv 5-47

Inv 5-2~5-47 were obtained as pale yellow solids according to the same procedure as in Synthesis Example 5-5 except for using corresponding starting materials instead of naphthalen-2-ylboronic acid.

Inv 5-2: Elemental Analysis: C, 94.61; H, 5.39/HRMS [M]$^+$: 672.
Inv 5-3: Elemental Analysis: C, 94.70; H, 5.30/HRMS [M]$^+$: 772
Inv 5-4: Elemental Analysis: C, 94.70; H, 5.30/HRMS [M]$^+$: 722
Inv 5-5: Elemental Analysis: C, 94.52; H, 5.48/HRMS [M]$^+$: 698
Inv 5-6: Elemental Analysis: C, 94.52; H, 5.48/HRMS [M]$^+$: 698
Inv 5-7: Elemental Analysis: C, 94.52; H, 5.48/HRMS [M]$^+$: 698
Inv 5-8: Elemental Analysis: C, 94.27; H, 5.73/HRMS [M]$^+$: 738
Inv 5-9: Elemental Analysis: C, 94.85; H, 5.15/HRMS [M]$^+$: 860
Inv 5-10: Elemental Analysis: C, 94.62; H, 5.38/HRMS [M]$^+$: 748
Inv 5-11: Elemental Analysis: C, 94.62; H, 5.38/HRMS [M]$^+$: 748
Inv 5-12: Elemental Analysis: C, 94.62; H, 5.38/HRMS [M]$^+$: 748
Inv 5-13: Elemental Analysis: C, 94.70; H, 5.30/HRMS [M]$^+$: 798
Inv 5-14: Elemental Analysis: C, 94.78; H, 5.22/HRMS [M]$^+$: 848
Inv 5-15: Elemental Analysis: C, 94.70; H, 5.30/HRMS [M]$^+$: 799
Inv 5-16: Elemental Analysis: C, 94.62; H, 5.38/HRMS [M]$^+$: 748
Inv 5-17: Elemental Analysis: C, 94.87; H, 5.13/HRMS [M]$^+$: 746
Inv 5-18: Elemental Analysis: C, 94.94; H, 5.06/HRMS [M]$^+$: 796
Inv 5-19: Elemental Analysis: C, 94.62; H, 5.38/HRMS [M]$^+$: 748
Inv 5-20: Elemental Analysis: C, 94.62; H, 5.38/HRMS [M]$^+$: 748
Inv 5-21: Elemental Analysis: C, 93.99; H, 6.01/HRMS [M]$^+$: 804
Inv 5-22: Elemental Analysis: C, 93.99; H, 6.01/HRMS [M]$^+$: 804
Inv 5-23: Elemental Analysis: C, 94.11; H, 5.89/HRMS [M]$^+$: 854
Inv 5-24: Elemental Analysis: C, 94.11; H, 5.89/HRMS [M]$^+$: 854
Inv 5-25: Elemental Analysis: C, 93.94; H, 6.06/HRMS [M]$^+$: 830
Inv 5-26: Elemental Analysis: C, 93.94; H, 6.06/HRMS [M]$^+$: 830
Inv 5-27: Elemental Analysis: C, 93.94; H, 6.06/HRMS [M]$^+$: 830
Inv 5-28: Elemental Analysis: C, 93.75; H, 6.25/HRMS [M]$^+$: 870
Inv 5-29: Elemental Analysis: C, 94.32; H, 5.68/HRMS [M]$^+$: 992
Inv 5-30: Elemental Analysis: C, 94.05; H, 5.95/HRMS [M]$^+$: 880
Inv 5-31: Elemental Analysis: C, 94.05; H, 5.95/HRMS [M]$^+$: 880
Inv 5-32: Elemental Analysis: C, 94.05; H, 5.95/HRMS [M]$^+$: 880
Inv 5-33: Elemental Analysis: C, 94.16; H, 5.84/HRMS [M]$^+$: 930
Inv 5-34: Elemental Analysis: C, 94.25; H, 5.75/HRMS [M]$^+$: 980
Inv 5-35: Elemental Analysis: C, 94.16; H, 5.84/HRMS [M]$^+$: 930
Inv 5-36: Elemental Analysis: C, 94.05; H, 5.95/HRMS [M]$^+$: 880
Inv 5-37: Elemental Analysis: C, 94.27; H, 5.73/HRMS [M]$^+$: 878
Inv 5-38: Elemental Analysis: C, 94.36; H, 5.64/HRMS [M]$^+$: 928
Inv 5-39: Elemental Analysis: C, 94.05; H, 5.95/HRMS [M]$^+$: 880

Inv 5-40: Elemental Analysis: C, 94.05; H, 5.95/HRMS [M]+: 880
Inv 5-41: Elemental Analysis: C, 94.05; H, 5.95/HRMS [M]+: 880
Inv 5-42: Elemental Analysis: C, 93.99; H, 6.01/HRMS [M]+: 804
Inv 5-43: Elemental Analysis: C, 94.54; H, 5.46/HRMS [M]+: 774
Inv 5-44: Elemental Analysis: C, 94.36; H, 5.64/HRMS [M]+: 750
Inv 5-45: Elemental Analysis: C, 94.14; H, 5.86/HRMS [M]+: 790
Inv 5-46: Elemental Analysis: C, 94.36; H, 5.64/HRMS [M]+: 750
Inv 5-47: Elemental Analysis: C, 94.70; H, 5.30/HRMS [M]+: 912

Synthesis Example 6-1

Preparation of Inv 6-1

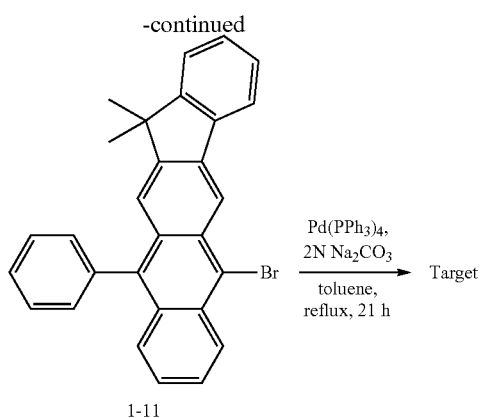

<Step 1> Synthesis of 2-(9,9-dimethyl-9H-fluorene-2-carbonyl)benzoic acid (Compound 1-3)

9,9-Dimethylfluorene (20 g, compound 1-1) and phthalic anhydride (23 g, compound 1-2) were dissolved in dichloromethane, and the reaction mixture was stirred at room temperature and aluminum chloride (20.5 g) was gradually added thereto at 0° C.

When it was stabilized, the reaction solution was stirred under reflux at 40° C. for six hours, concentrated and purified by column chromatography. The resultant product was dissolved in dichloromethane, precipitated with n-hexane and filtered. The solid thus obtained was dried under reduced pressure to give a titled compound (27 g, yield 76%).

$^1$H NMR: 8.44 (t, 2H), 8.23 (d, 1H), 7.96 (m, 5H), 7.72 (m, 5H), 7.55 (t, 1H), 1.67 (s, 6H).

<Step 2> Synthesis of 13,13-dimethyl-6H-indeno[1,2-b]anthracene-6,11(13H)-dione (compound 1-4)

Polyphosphoric acid (50 ml) was added to the compound (27 g) obtained in <Step 1>, and the reaction mixture was stirred at 130° C. for three hours while heating. Then, ice water (400 ml) was added thereto at room temperature, and the resultant solid was filtered, washed with methanol, and dried under reduced pressure to give a titled compound (19 g, yield 74%).

$^1$H NMR: 8.29 (t, 3H), 8.09 (s, 2H), 7.85 (d, 2H), 7.72 (m, 2H), 1.67 (s, 6H).

<Step 3> Synthesis of 13,13-dimethyl-11,13-dihydro-6H-indeno[1,2-b]anthracene-6,11-diol (Compound 1-5)

The compound (64 g) obtained through repetition of <Step 2> was dispersed in methanol (2 l), and three fractions of sodium borohydride (30 g) were sequentially gradually added thereto at 0° C. The reaction mixture was stirred at 0° C. for three hours and filtered with water (3 l). The resultant solid was sufficiently washed with water and dried at room temperature.

<Step 4> Synthesis of 13,13-dimethyl-6H-indeno[1,2-b]anthracen-11(13H)-one (Compound 1-6)

The product obtained in <Step 3> was dispersed in 5N HCl (300 ml) and the reaction mixture was stirred under reflux for 20 hours. The reaction solution was cooled to room temperature and filtered with water (300 ml).

The resultant solid was sufficiently washed with water and dried under reduced pressure to give a titled compound (60.3 g, yield 98.5%).

<Step 5> Synthesis of 13,13-dimethyl-13H-indeno[1,2-b]anthracene (Compound 1-7)

The compound (60.3 g) obtained in <Step 4> was dispersed in isopropanol (1.5 l) and sodium borohydride (36.7 g) was added thereto. The reaction mixture was stirred under reflux for 22 hours and cooled to room temperature. The resultant red product was poured into water (2 l) and the resultant solution was stirred. The resultant solid was filtered and sufficiently washed with water to obtain a yellowish solid.

The solid was subjected to water removal and purified by column chromatography to give a titled compound (27.9 g, yield 48.7%) as a light green solid.

$^1$H NMR (500 MHz, THF-d8) 8.49 (s, 1H), 8.43 (s, 1H), 8.34 (s, 1H), 8.03 (s, 1H), 7.98 (dd, 2H), 7.95 (m, 1H), 7.50 (m, 1H), 7.40 (m, 2H), 7.35 (m, 2H), 1.60 (s, 6H)
Mass: [M+1]+ 294

<Step 6> Synthesis of 11-bromo-13,13-dimethyl-13H-indeno[1,2-b]anthracene (Compound 1-8)

The compound (27.9 g) obtained in <Step 5> was dissolved in dimethylformamide (400 ml) and N-bromosuccinimide (18.5 g) was added thereto.

The reaction mixture was stirred at room temperature for one hour and poured into water (1l). The resultant solid was filtered, sufficiently washed with water and methanol and dried under reduced pressure to give a titled compound (33.3 g, yield 94.2%) as a pale yellow solid.

$^1$H NMR (500 MHz, THF-d8) 8.83 (s, 1H), 8.53 (s, 1H), 8.48 (d, 1H), 8.08 (s, 1H), 8.06 (t, 1H), 8.03 (d, 1H), 7.59 (m, 1H), 7.53 (m, 1H), 7.49 (m, 1H), 7.40 (m, 2H), 1.62 (s, 6H)
Mass: [M+1]+ 372

<Step 7> Synthesis of 13,13-dimethyl-1'-phenyl-13H-indeno[1,2-b]anthracene (Compound 1-10)

The compound (33.3 g) obtained in <Step 6> and phenylboronic acid (compound 1-9, 13 g) were dissolved in toluene (450 ml), tetrakis(triphenylphosphine)palladium(0) (3 g) and 2N sodium carbonate (150 ml) were added thereto, and the reaction mixture was stirred under reflux.

The reaction solution was cooled to room temperature, and an organic layer was collected, washed with water and a saturated sodium chloride solution, dried over anhydrous sodium sulfate and concentrated.

The crude product was purified by column chromatography (n-hexane~n-hexane/dichloromethane=9/1), precipitated with n-hexane and filtered to give a titled compound (32.3 g, yield 97.8%) as a yellow solid.

$^1$H NMR (500 MHz, THF-d8) 8.54 (s, 1H), 8.49 (s, 1H), 8.37 (d, 1H), 7.86 (m, 2H), 7.80 (m, 2H), 7.71 (s, 1H), 7.64 (m, 3H), 7.54 (m, 3H), 7.38 (m, 2H), 1.65 (s, 6H)
Mass: [M+1]+ 370

<Step 8> Synthesis of 6-bromo-13,13-dimethyl-11-phenyl-13H-indeno[1,2-b]anthracene (Compound 1-11)

The compound (32.3 g) obtained in <Step 7> was dissolved in dimethylformamide (400 ml) and N-bromosuccinimide (17.1 g) was added thereto.

The reaction mixture was stirred at room temperature for one hour and poured into water (1 l). The resultant solid was filtered, sufficiently washed with water and methanol and dried under reduced pressure to give a titled compound (38.2 g, yield 97.5%) as a pale yellow solid.

$^1$H NMR (500 MHz, THF-d8) 8.64 (s, 1H), 8.58 (d, 1H), 7.92 (s, 1H), 7.62 (m, 6H), 7.51 (d, 1H), 7.47 (dd, 2H), 7.36 (m, 2H), 7.26 (t, 1H), 1.65 (s, 6H)

Mass: [M+1]+ 448

<Step 9> Synthesis of pyrene-1-boronic acid (Compound 1-13)

1-Bromopyrene (compound 1-12, 30 g) was dissolved in tetrahydrofuran (500 ml). The reaction mixture was cooled to −78° C. and stirred for one hour while gradually adding an n-butyllithium solution (1.6N, 80 ml) thereto, and triisopropylborate (30 ml) was added thereto.

The reaction solution was gradually raised to room temperature and stirred at that temperature for 15 hours. 1N HCl (250 ml) was gradually added and an aqueous layer was removed. The resultant organic layer was washed with a saturated ammonium chloride solution and a saturated sodium chloride solution, dried over anhydrous sodium sulfate and concentrated. The crude product was recrystallized from n-hexane to give a titled compound (15.7 g, yield 60.0%) as a pale yellow solid.

<Step 10> Synthesis of 13,13-dimethyl-1'-phenyl-6-(pyren-1-yl)-13H-indeno[1,2-b]anthracene (Inv 6-1)

The compound (20 g) obtained in <Step 8> and the compound (11.8 g) obtained in <Step 9> were dissolved in toluene (200 ml), tetrakis(triphenylphosphine)palladium(0) (1.4 g) and an aqueous 2N sodium carbonate solution (60 ml) were added thereto, and the reaction mixture was stirred under reflux for 21 hours.

The reaction solution was cooled to room temperature, and an organic layer was collected, washed with water and a saturated sodium chloride solution, dried over anhydrous sodium sulfate and concentrated.

The crude product was purified by column chromatography (n-hexane~n-hexane/dichloromethane=9/1), precipitated with n-hexane and filtered to give a titled compound (5.75 g, yield 25.2%) as a pale yellow solid, represented by the following structure.

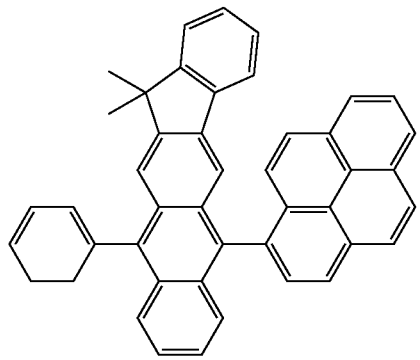 [SMILES: CC1(C)c2ccccc2-c2cc3c(-c4ccc5ccc6cccc7ccc4c5c67)c4ccccc4c(C4=CC=CCC4)c3cc21]

$^1$H NMR (500 MHz, THF-d8) 8.48 (d, 1H), 8.31 (m, 2H), 8.26 (m, 1H), 8.17 (dd, 1H), 8.13 (dd, 1H), 8.08 (s, 1H), 8.03 (t, 1H), 7.86 (d, 1H), 7.72 (m, 3H), 7.64 (m, 4H), 7.49 (s, 1H), 7.44 (d, 1H), 7.34 (m, 1H), 7.26 (m, 4H), 7.12 (m, 1H), 1.28 (s, 3H), 1.14 (s, 3H)

Mass: [M]+ 546

Synthesis Example 6-2

Preparation of Inv 6-2

The compound (20 g) obtained in <Step 8> of Synthesis Example 6-1 and 4,4,5,5-tetramethyl-2-(phenanthren-9-yl)-1,3,2-dioxaborolane (14.6 g) were dissolved in toluene (200 ml), tetrakis(triphenylphosphine)palladium(0) (1.4 g), 2N sodium carbonate (60 ml) and aliquat 336 (1.8 ml) were added thereto, and the reaction mixture was stirred under reflux for 21 hours.

The reaction solution was cooled to room temperature, and an organic layer was collected, washed with water and a saturated sodium chloride solution, dried over anhydrous sodium sulfate and concentrated.

The crude product was purified by column chromatography (n-hexane~n-hexane/dichloromethane=9/1), precipitated with n-hexane and filtered to give a titled compound (12.7 g, yield 58.0%) as a pale yellow solid, represented by the following structure.

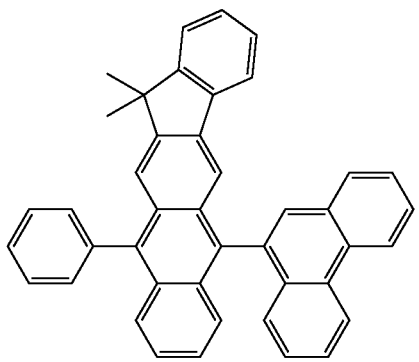 [SMILES: CC1(C)c2ccccc2-c2cc3c(-c4cc5ccccc5c5ccccc45)c4ccccc4c(-c4ccccc4)c3cc21]

$^1$H NMR (500 MHz, THF-d8) 8.98 (m, 2H), 8.04 (s, 1H), 7.99 (d, 1H), 7.94 (s, 1H), 7.79 (m, 1H), 7.68 (m, 4H), 7.61 (m, 5H), 7.58 (d, 1H), 7.46 (d, 1H), 7.35 (d, 1H), 7.26 (m, 5H), 7.16 (t, 1H), 1.30 (s, 3H), 1.18 (s, 3H)

Mass: [M]+ 570

Synthesis Example 6-3

Preparation of Inv 6-3

The compound (20 g) obtained in <Step 8> of Synthesis Example 6-1 and 4,4,5,5-tetramethyl-2-(triphenylen-2-yl)-1,3,2-dioxaborolane (17 g) were dissolved in toluene (200 ml), tetrakis(triphenylphosphine)palladium(0) (1.4 g), 2N sodium carbonate (60 ml) and aliquat 336 (1.8 ml) were added thereto, and the reaction mixture was stirred under reflux for 21 hours.

The reaction solution was cooled to room temperature, and an organic layer was collected, washed with water and a saturated sodium chloride solution, dried over anhydrous sodium sulfate and concentrated.

The crude product was purified by column chromatography (n-hexane~n-hexane/dichloromethane=9/1), precipitated with n-hexane and filtered to give a titled compound (11.5 g, yield 48.2%) as a pale yellow solid, represented by the following structure.

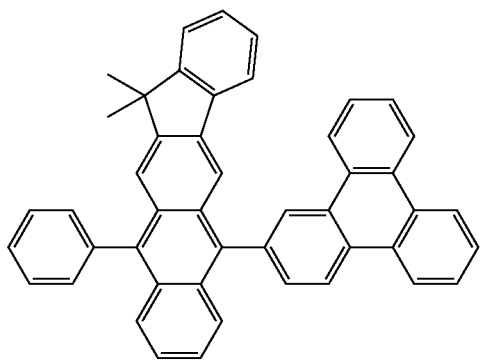 [SMILES: CC1(C)c2ccccc2-c2cc3c(-c4ccc5c6ccccc6c6ccccc6c5c4)c4ccccc4c(-c4ccccc4)c3cc21]

¹H NMR (500 MHz, THF-d8) 9.15 (s, 1H), 8.93 (d, 2H), 8.21 (m, 2H), 8.10 (d, 2H), 8.06 (m, 2H), 7.91 (d, 2H), 7.78 (s, 1H), 7.67 (m, 4H), 7.44 (m, 4H), 7.28 (dd, 2H), 7.24 (m, 3H), 7.18 (t, 1H), 1.27 (s, 3H), 1.14 (s, 3H)

Mass: [M]+ 596

Example 1

Fabrication of Organic Light-Emitting Devices

Organic light-emitting devices (OLEDs) were manufactured as follows.

A glass substrate coated with ITO (Indium tin oxide) (coating thickness: 1500 Å) was ultrasonically washed with distilled water and then with isopropyl alcohol, acetone, methanol etc., and dried. Then, the glass substrate was transported to a plasma cleaner, cleaned with oxygen plasma for five minutes and transported to a vacuum deposition machine. Then, OLEDs were manufactured as presented in Table 1 below.

In detail, DS-HIL (Doosan, Korea) was deposited under thermal vacuum to a thickness of 800 Å on the ITO (anode) thus prepared to form a hole injection layer (HIL), and a hole transport material, a-NPB (N,N-di(naphthalene-1-yl)-N,N-diphenylbenzidine) was deposited under vacuum to a thickness of 150 Å on the hole injection layer to form a hole transport layer (HTL).

Next, Inv 1-1 and DS-Dopant (Doosan, Korea) were deposited under vacuum to a thickness of 300 Å to form a light-emitting layer (EML). Then, an electron transport material, Alq3 was deposited under vacuum to a thickness of 250 Å on the light-emitting layer to form an electron transport layer (ETL). Then, an electron injection material, LiF was deposited to a thickness of 10 Å on the electron transport layer to form an electron injection layer (EIL), and aluminum was deposited under vacuum to a thickness of 2000 Å to form a cathode.

Examples 2~214

Fabrication of OLEDs

OLEDs were manufactured in the same manner as in Example 1 except that Inv 1-2~Inv 1-60, Inv 2-1~Inv 2-48, Inv 3-1~Inv 3-29, Inv 4-1~Inv 4-30, and Inv 5-1~Inv 5-47 were used as light-emitting materials instead of Inv 1-1.

Examples 215~217

Fabrication of OLEDs

OLEDs were manufactured in the same manner as in Example 1 except that Inv 6-1~Inv 6-3 were used as light-emitting materials instead of Inv 1-1 and C-545T was used as a dopant.

Comparative Example 1

Fabrication of OLED

An OLED was manufactured in the same manner as in Example 1 except that Alq3 and C-545T commonly used in a green light-emitting system were used instead of Inv 1-1 and DS-Dopant (Doosan, Korea).

TABLE 1

| | HIL | HTL | EML | ETL | EIL | Cathode |
|---|---|---|---|---|---|---|
| Examples 1-214 | DS-HIL | a-NPB | Inv1-1 ~5-47 + DS-Dopant | Alq3 | LiF | Al |
| Examples 215-217 | DS-HIL | a-NPB | Inv 6-1~6-3 + C-545T | Alq3 | LiF | Al |
| Comparative Example 1 | DS-HIL | a-NPB | Alq3 + C-545T | Alq3 | LiF | Al |

Experimental Examples

Emission efficiencies at current density of 10 mA/cm² were measured for the OLEDs manufactured in Examples 1~217 and Comparative Example 1, and the results are presented in Tables 2 to 7 below.

TABLE 2

| compound | Voltage (V) | Efficiency (cd/A) | compound | Voltage (V) | Efficiency (cd/A) | compound | Voltage (V) | Efficiency (cd/A) |
|---|---|---|---|---|---|---|---|---|
| Inv 1-1 | 6.5 | 23 | Inv 1-2 | 6.2 | 21 | Inv 1-3 | 6.7 | 20 |
| Inv 1-4 | 6.5 | 18 | Inv 1-5 | 6.6 | 13 | Inv 1-6 | 6.7 | 16 |
| Inv 1-7 | 6.9 | 18 | Inv 1-8 | 6.4 | 23 | Inv 1-9 | 6 | 15 |
| Inv 1-10 | 6.2 | 22 | Inv 1-11 | 6 | 20 | Inv 1-12 | 6.4 | 19 |
| Inv 1-13 | 6.3 | 18 | Inv 1-14 | 6.2 | 19 | Inv 1-15 | 6.6 | 22 |
| Inv 1-16 | 6.7 | 20 | Inv 1-17 | 6.5 | 17 | Inv 1-18 | 6.5 | 20 |
| Inv 1-19 | 6.2 | 23 | Inv 1-20 | 6.1 | 16 | Inv 1-21 | 6.8 | 23 |
| Inv 1-22 | 7.1 | 23 | Inv 1-23 | 6.7 | 23 | Inv 1-24 | 6.2 | 21 |
| Inv 1-25 | 6 | 20 | Inv 1-26 | 6.3 | 18 | Inv 1-27 | 6.8 | 13 |
| Inv 1-28 | 6.9 | 16 | Inv 1-29 | 6.3 | 18 | Inv 1-30 | 6.5 | 23 |
| Inv 1-31 | 6.6 | 15 | Inv 1-32 | 6.6 | 22 | Inv 1-33 | 6.8 | 20 |
| Inv 1-34 | 6.4 | 19 | Inv 1-35 | 6.2 | 18 | Inv 1-36 | 6.3 | 19 |
| Inv 1-37 | 6.9 | 22 | Inv 1-38 | 6.1 | 20 | Inv 1-39 | 6.9 | 17 |
| Inv 1-40 | 6 | 20 | Inv 1-41 | 6.3 | 23 | Inv 1-42 | 6.3 | 16 |

TABLE 2-continued

| compound | Voltage (V) | Efficiency (cd/A) | compound | Voltage (V) | Efficiency (cd/A) | compound | Voltage (V) | Efficiency (cd/A) |
|---|---|---|---|---|---|---|---|---|
| Inv 1-43 | 6.5 | 23 | Inv 1-44 | 6.9 | 23 | Inv 1-45 | 7.2 | 23 |
| Inv 1-46 | 7 | 23 | Inv 1-47 | 6.3 | 23 | Inv 1-48 | 6.5 | 21 |
| Inv 1-49 | 6.4 | 20 | Inv 1-50 | 6.8 | 18 | Inv 1-51 | 6.3 | 13 |
| Inv 1-52 | 6.8 | 16 | Inv 1-53 | 6.3 | 18 | Inv 1-54 | 6.9 | 23 |
| Inv 1-55 | 6.4 | 15 | Inv 1-56 | 6.8 | 22 | Inv 1-57 | 6.9 | 20 |
| Inv 1-58 | 6.1 | 19 | Inv 1-59 | 6.2 | 18 | Inv 1-60 | 6.3 | 19 |

TABLE 3

| compound | Voltage (V) | Efficiency (cd/A) | compound | Voltage (V) | Efficiency (cd/A) | compound | Voltage (V) | Efficiency (cd/A) |
|---|---|---|---|---|---|---|---|---|
| Inv 2-1 | 6.8 | 23 | Inv 2-2 | 6.8 | 22 | Inv 2-3 | 6.4 | 23 |
| Inv 2-4 | 6.5 | 23 | Inv 2-5 | 6.6 | 16 | Inv 2-6 | 6.7 | 21 |
| Inv 2-7 | 6.9 | 20 | Inv 2-8 | 6.4 | 18 | Inv 2-9 | 6 | 13 |
| Inv 2-10 | 6.2 | 16 | Inv 2-11 | 6 | 18 | Inv 2-12 | 6.4 | 23 |
| Inv 2-13 | 6.3 | 15 | Inv 2-14 | 6.2 | 22 | Inv 2-15 | 6.6 | 20 |
| Inv 2-16 | 6.7 | 19 | Inv 2-17 | 6.5 | 18 | Inv 2-18 | 6.5 | 19 |
| Inv 2-19 | 6.2 | 22 | Inv 2-20 | 6.1 | 20 | Inv 2-21 | 6.8 | 17 |
| Inv 2-22 | 7.1 | 20 | Inv 2-23 | 6.7 | 23 | Inv 2-24 | 6.2 | 16 |
| Inv 2-25 | 6 | 23 | Inv 2-26 | 6.3 | 23 | Inv 2-27 | 6.8 | 23 |
| Inv 2-28 | 6.9 | 23 | Inv 2-29 | 6.3 | 23 | Inv 2-30 | 6.5 | 21 |
| Inv 2-31 | 6.6 | 20 | Inv 2-32 | 6.6 | 18 | Inv 2-33 | 6.8 | 13 |
| Inv 2-34 | 6.4 | 16 | Inv 2-35 | 6.2 | 18 | Inv 2-36 | 6.3 | 23 |
| Inv 2-37 | 6.9 | 15 | Inv 2-38 | 6.1 | 22 | Inv 2-39 | 6.9 | 20 |
| Inv 2-40 | 6 | 19 | Inv 2-41 | 6.3 | 18 | Inv 2-42 | 6.3 | 19 |
| Inv 2-43 | 6.5 | 22 | Inv 2-44 | 6.9 | 20 | Inv 2-45 | 7.2 | 17 |
| Inv 2-46 | 7 | 20 | Inv 2-47 | 6.3 | 23 | Inv 2-48 | 6.5 | 16 |

TABLE 4

| compound | Voltage (V) | Efficiency (cd/A) | compound | Voltage (V) | Efficiency (cd/A) | compound | Voltage (V) | Efficiency (cd/A) |
|---|---|---|---|---|---|---|---|---|
| Inv 3-1 | 6.5 | 22 | Inv 3-2 | 6.2 | 20 | Inv 3-3 | 6.7 | 19 |
| Inv 3-4 | 6.5 | 18 | Inv 3-5 | 6.6 | 19 | Inv 3-6 | 6.7 | 22 |
| Inv 3-7 | 6.9 | 20 | Inv 3-8 | 6.4 | 17 | Inv 3-9 | 6 | 20 |
| Inv 3-10 | 6.2 | 23 | Inv 3-11 | 6 | 16 | Inv 3-12 | 6.4 | 23 |
| Inv 3-13 | 6.3 | 23 | Inv 3-14 | 6.2 | 23 | Inv 3-15 | 6.6 | 23 |
| Inv 3-16 | 6.7 | 23 | Inv 3-17 | 6.5 | 21 | Inv 3-18 | 6.5 | 20 |
| Inv 3-19 | 6.2 | 18 | Inv 3-20 | 6.1 | 13 | Inv 3-21 | 6.8 | 16 |
| Inv 3-22 | 7.1 | 18 | Inv 3-23 | 6.7 | 23 | Inv 3-24 | 6.2 | 15 |
| Inv 3-25 | 6 | 22 | Inv 3-26 | 6.3 | 20 | Inv 3-27 | 6.8 | 19 |
| Inv 3-28 | 6.9 | 18 | Inv 3-29 | 6.3 | 19 | | | |

TABLE 5

| compound | Voltage (V) | Efficiency (cd/A) | compound | Voltage (V) | Efficiency (cd/A) | compound | Voltage (V) | Efficiency (cd/A) |
|---|---|---|---|---|---|---|---|---|
| Inv 4-1 | 6.5 | 22 | Inv 4-2 | 6.6 | 20 | Inv 4-3 | 6.6 | 17 |
| Inv 4-4 | 6.8 | 20 | Inv 4-5 | 6.4 | 23 | Inv 4-6 | 6.2 | 16 |
| Inv 4-7 | 6.3 | 22 | Inv 4-8 | 6.9 | 20 | Inv 4-9 | 6.1 | 19 |
| Inv 4-10 | 6.9 | 18 | Inv 4-11 | 6 | 19 | Inv 4-12 | 6.3 | 22 |
| Inv 4-13 | 6.3 | 16 | Inv 4-14 | 6.5 | 23 | Inv 4-15 | 6.9 | 23 |
| Inv 4-16 | 7.2 | 23 | Inv 4-17 | 7 | 23 | Inv 4-18 | 6.3 | 23 |
| Inv 4-19 | 6.5 | 21 | Inv 4-20 | 6.4 | 20 | Inv 4-21 | 6.8 | 18 |
| Inv 4-22 | 6.3 | 13 | Inv 4-23 | 6.8 | 16 | Inv 4-24 | 6.3 | 18 |
| Inv 4-25 | 6.9 | 23 | Inv 4-26 | 6.4 | 15 | Inv 4-27 | 6.8 | 22 |
| Inv 4-28 | 6.9 | 20 | Inv 4-29 | 6.1 | 19 | Inv 4-30 | 6.2 | 18 |

TABLE 6

| Compound | Voltage (V) | Efficiency (cd/A) | Compound | Voltage (V) | Efficiency (cd/A) | Compound | Voltage (V) | Efficiency (cd/A) |
|---|---|---|---|---|---|---|---|---|
| Inv5-1 | 6.8 | 20 | Inv5-2 | 6.4 | 18 | Inv5-3 | 6.2 | 13 |
| Inv5-4 | 6.3 | 16 | Inv5-5 | 6.9 | 18 | Inv5-6 | 6.1 | 23 |
| Inv5-7 | 6.9 | 15 | Inv5-8 | 6 | 22 | Inv5-9 | 6.3 | 20 |
| Inv5-10 | 6.3 | 19 | Inv5-11 | 6.5 | 18 | Inv5-12 | 6.9 | 23 |
| Inv5-13 | 7.2 | 15 | Inv5-14 | 7 | 22 | Inv5-15 | 6.3 | 20 |
| Inv5-16 | 6.5 | 20 | Inv5-17 | 6.4 | 18 | Inv5-18 | 6.8 | 13 |
| Inv5-19 | 6.3 | 16 | Inv5-20 | 6.8 | 18 | Inv5-21 | 6.3 | 23 |
| Inv5-22 | 6.9 | 15 | Inv5-23 | 6.4 | 22 | Inv5-24 | 6.8 | 20 |
| Inv5-25 | 6.9 | 19 | Inv5-26 | 6.1 | 18 | Inv5-27 | 6.2 | 19 |
| Inv5-28 | 6.3 | 20 | Inv5-29 | 6.5 | 18 | Inv5-30 | 6.5 | 13 |
| Inv5-31 | 6.2 | 16 | Inv5-32 | 6.7 | 18 | Inv5-33 | 6.5 | 23 |
| Inv5-34 | 6.6 | 15 | Inv5-35 | 6.7 | 22 | Inv5-36 | 6.9 | 20 |
| Inv5-37 | 6.4 | 19 | Inv5-38 | 6 | 18 | Inv5-39 | 6.2 | 19 |
| Inv5-40 | 6 | 20 | Inv5-41 | 6.4 | 18 | Inv5-42 | 6.3 | 13 |
| Inv5-43 | 6.2 | 16 | Inv5-44 | 6.6 | 18 | Inv5-45 | 6.7 | 23 |
| Inv5-46 | 6.5 | 15 | Inv5-47 | 6.5 | 22 | Comparative Example 1 | 4.7 | 11.7 |

As can be seen from the above results, the inventive compounds can provide an about 40% or more increase of efficiency as compared to conventional light-emitting materials. This suggests that an energy transfer from a host to a dopant in the inventive systems is faster than that in the conventional system of Alq3 (host) and C-545T (dopant). Therefore, it is expected that the inventive compounds can significantly enhance the performance of full-color organic EL panels.

TABLE 7

| Compound | Operating voltage (V) | Emission efficiency (cd/A) |
|---|---|---|
| Inv 6-1 | 4.9 | 19.9 |
| Inv 6-2 | 5.1 | 21.2 |
| Inv 6-3 | 5.3 | 22.1 |

As shown in Table 7, OLEDs using the inventive compounds as host materials exhibited significant improvements in voltage and efficiency, in particular lifetime, as compared to conventional OLEDs using Alq3 as a host material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound represented by Formula 1 below:

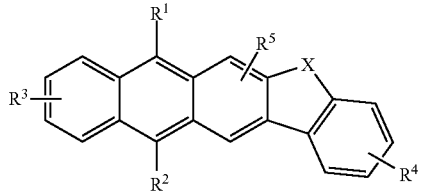

<Formula 1> wherein X is selected from the group consisting of $CR^6R^7$, $NR^6$, O, S, S(=O), S(=O)$_2$ and $SiR^6R^7$;

$R^1$ through $R^7$ are the same or different and each independently selected from the group consisting of hydrogen (H), deuterium (D), an alkyl group of $C_1$~$C_{40}$, an alkenyl group of $C_2$~$C_{40}$, an alkynyl group of $C_2$~$C_{40}$, an aryl group of $C_5$~$C_{40}$, a heteroaryl group of $C_5$~$C_{40}$, an aryloxy group of $C_5$~$C_{40}$, an alkyloxy group of $C_1$~$C_{40}$, an arylamino group of $C_5$~$C_{40}$, a diarylamino group of $C_5$~$C_{40}$, an arylalkyl group of $C_6$~$C_{40}$, a cycloalkyl group of $C_3$~$C_{40}$ and a heterocycloalkyl group of $C_3$~$C_{40}$, or a group binding with an adjacent group to form a fused aliphatic ring, a fused aromatic ring, a fused heteroaliphatic ring or a fused heteroaromatic ring;

in $R^1$ through $R^7$, the alkyl group of $C_1$~$C_{40}$, the alkenyl group of $C_2$~$C_{40}$, the alkynyl group of $C_2$~$C_{40}$, the aryl group of $C_5$~$C_{40}$, the heteroaryl group of $C_5$~$C_{40}$, the aryloxy group of $C_5$~$C_{40}$, the alkyloxy group of $C_1$~$C_{40}$, the arylamino group of $C_5$~$C_{40}$, the diarylamino group of $C_5$~$C_{40}$, the arylalkyl group of $C_6$~$C_{40}$, the cycloalkyl group of $C_3$~$C_{40}$ and the heterocycloalkyl group of $C_3$~$C_{40}$ are each independently unsubstituted or substituted by at least one selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$ and a heteroaryl group of $C_5$~$C_{40}$; and two or more of $R^1$ through $R^4$ are each independently an aryl group of $C_5$~$C_{40}$.

2. The compound of claim 1, wherein two or more of $R^1$ through $R^4$ are each independently an aryl group of $C_5$~$C_{40}$ selected from the group consisting of chemical structures represented in Formula 2 below:

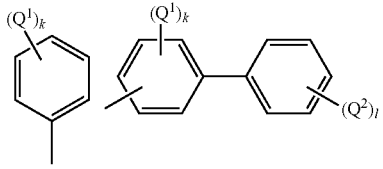
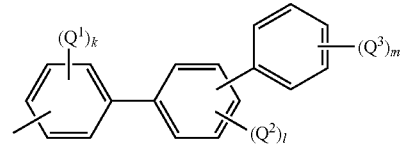

<Formula 2>

-continued

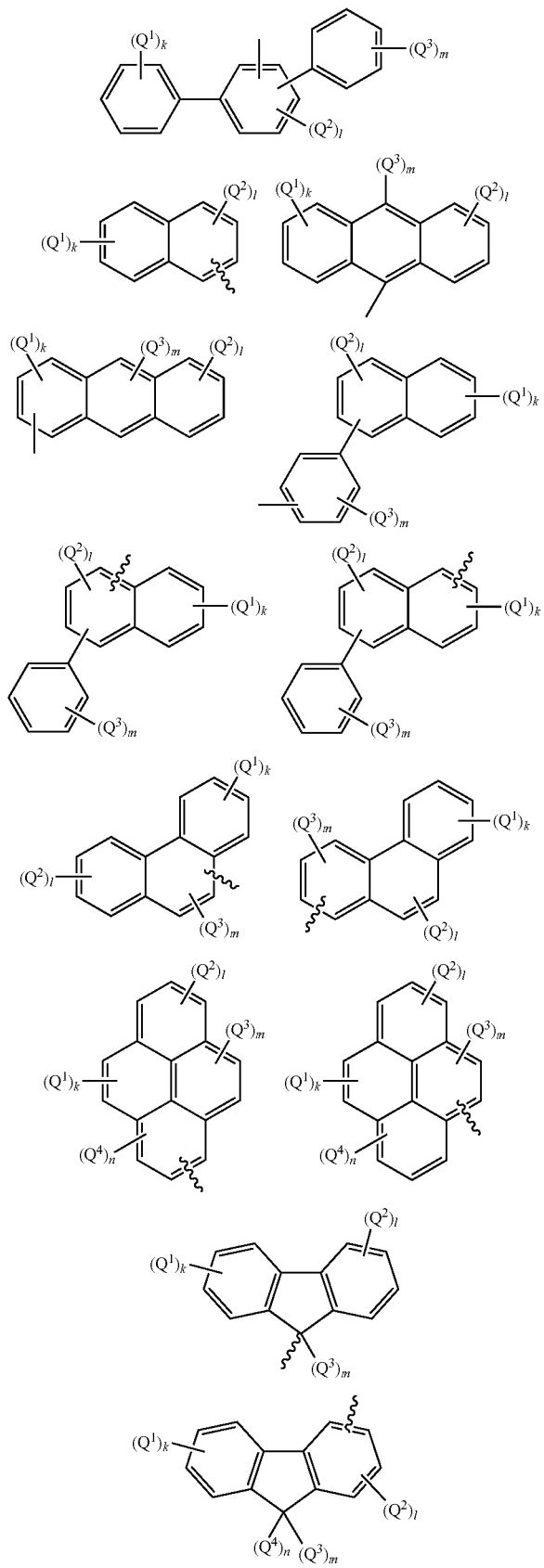
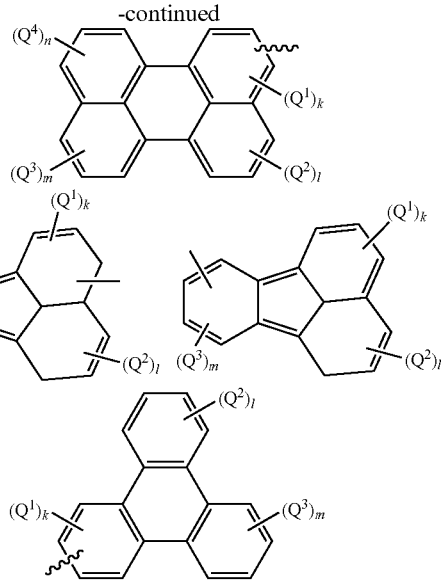

wherein k, l, m and n are each independently an integer ranging from 1 to 5;

$Q^1$s are the same or different, $Q^2$s are the same or different, $Q^3$s are the same or different, and $Q^4$s are the same or different;

$Q^1$ through $Q^4$ are the same or different and each independently selected from the group consisting of hydrogen, deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$ and a heteroaryl group of $C_5$~$C_{40}$; or a group binding with an adjacent group to form a fused aliphatic ring, a fused aromatic ring, a fused heteroaliphatic ring or a fused heteroaromatic ring.

3. The compound of claim 2, wherein among $R^1$ through $R^4$, $R^1$ and $R^2$; or $R^3$ and $R^4$; or $R^1$, $R^2$ and $R^3$; or $R^1$, $R^2$ and $R^4$; or $R^1$, $R^2$, $R^3$ and $R^4$ are each independently an aryl group of $C_5$~$C_{40}$ selected from the group consisting of the chemical structures represented in Formula 2.

4. The compound of claim 1, wherein $R^1$ and $R^2$ are different.

5. The compound of claim 1, wherein among the substituents to be introduced in $R^1$ through $R^7$ at the alkyl group of $C_1$~$C_{40}$, the alkenyl group of $C_2$~$C_{40}$, the alkynyl group of $C_2$~$C_{40}$, the aryl group of $C_5$~$C_{40}$, the heteroaryl group of $C_5$~$C_{40}$, the aryloxy group of $C_5$~$C_{40}$, the alkyloxy group of $C_1$~$C_{40}$, the arylamino group of $C_5$~$C_{40}$, the diarylamino group of $C_5$~$C_{40}$, the arylalkyl group of $C_6$~$C_{40}$, the cycloalkyl group of $C_3$~$C_{40}$ and the heterocycloalkyl group of $C_3$~$C_{40}$, the alkyl group of $C_1$~$C_{40}$, the alkenyl group of $C_2$~$C_{40}$, the alkoxy group of $C_1$~$C_{40}$, the amino group of $C_1$~$C_{40}$, the cycloalkyl group of $C_3$~$C_{40}$, the heterocycloalkyl group of $C_3$~$C_{40}$, the aryl group of $C_6$~$C_{40}$ and the heteroaryl group of $C_5$~$C_{40}$ are each independently substituted by at least one selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$ and a heteroaryl group of $C_5$~$C_{40}$; or bind with an adjacent group to form a fused aliphatic ring, a fused aromatic ring, a fused heteroaliphatic ring, a fused heteroaromatic ring, or a spiro bond.

6. An organic light-emitting device comprising (i) an anode, (ii) a cathode, and (iii) one or more organic material layers interposed between the anode and the cathode, wherein at least one of the organic material layers is an organic material layer comprising the compound of Formula 1 of claim 1.

7. The organic light-emitting device of claim 6, wherein the organic material layer comprising the compound of Formula 1 is a light-emitting layer.

8. An organic light-emitting device comprising (i) an anode, (ii) a cathode, and (iii) one or more organic material layers interposed between the anode and the cathode, wherein at least one of the organic material layers is an organic material layer comprising the compound of claim 2.

9. An organic light-emitting device comprising (i) an anode, (ii) a cathode, and (iii) one or more organic material layers interposed between the anode and the cathode, wherein at least one of the organic material layers is an organic material layer comprising the compound of claim 3.

10. An organic light-emitting device comprising (i) an anode, (ii) a cathode, and (iii) one or more organic material layers interposed between the anode and the cathode, wherein at least one of the organic material layers is an organic material layer comprising the compound of claim 4.

11. An organic light-emitting device comprising (i) an anode, (ii) a cathode, and (iii) one or more organic material layers interposed between the anode and the cathode, wherein at least one of the organic material layers is an organic material layer comprising the compound of claim 5.

* * * * *